(12) United States Patent
Schroeder et al.

(10) Patent No.: US 11,992,557 B2
(45) Date of Patent: May 28, 2024

(54) COLLAGENASE LOADED LIPOSOMES FOR ENHANCING DRUG DELIVERY

(71) Applicant: TECHNION RESEARCH & DEVELOPMENT FOUNDATION LIMITED, Haifa (IL)

(72) Inventors: Avi Schroeder, Binyamina (IL); Assaf Zinger, Haifa (IL)

(73) Assignee: TECHNION RESEARCH & DEVELOPMENT FOUNDATION LIMITED, Haifa (IL)

(*) Notice: Subject to any disclaimer, the term of this patent is extended or adjusted under 35 U.S.C. 154(b) by 403 days.

(21) Appl. No.: 16/963,648

(22) PCT Filed: Jan. 23, 2019

(86) PCT No.: PCT/IL2019/050097
§ 371 (c)(1),
(2) Date: Jul. 21, 2020

(87) PCT Pub. No.: WO2019/145950
PCT Pub. Date: Aug. 1, 2019

(65) Prior Publication Data
US 2021/0059936 A1    Mar. 4, 2021

Related U.S. Application Data

(60) Provisional application No. 62/620,597, filed on Jan. 23, 2018, provisional application No. 62/620,602, filed on Jan. 23, 2018.

(51) Int. Cl.
| | | |
|---|---|---|
| *A61K 9/127* | (2006.01) | |
| *A61K 31/337* | (2006.01) | |
| *A61K 38/48* | (2006.01) | |
| *A61P 35/00* | (2006.01) | |

(52) U.S. Cl.
CPC ............ *A61K 9/127* (2013.01); *A61K 9/1277* (2013.01); *A61K 31/337* (2013.01); *A61K 38/4886* (2013.01); *A61P 35/00* (2018.01); *C12Y 304/24007* (2013.01)

(58) Field of Classification Search
None
See application file for complete search history.

(56) References Cited

U.S. PATENT DOCUMENTS

| | | | |
|---|---|---|---|
| 4,732,758 A * | 3/1988 | Hurion | C12N 9/52 424/94.2 |
| 5,858,397 A | 1/1999 | Lim et al. | |
| 6,428,785 B1 | 8/2002 | Gokcen | |
| 8,062,663 B2 | 11/2011 | Wang et al. | |
| 2004/0013720 A1* | 1/2004 | Ellens | A61P 35/00 424/450 |
| 2017/0209551 A1* | 7/2017 | Schroeder | A61K 9/0063 |

FOREIGN PATENT DOCUMENTS

| | | | |
|---|---|---|---|
| EP | 0356339 B1 | 3/1995 | |
| JP | 2015071645 A | 4/2015 | |
| WO | 2015140802 A2 | 9/2015 | |
| WO | WO-2015140802 A2 * | 9/2015 | ........... A61C 19/063 |

OTHER PUBLICATIONS

Sigma Aldrich (https://www.sigmaaldrich.com/deepweb/assets/sigmaaldrich/product/documents/420/044/c9891dat.pdf) (Year: 2008).*
Molecular Probes (2001) (Year: 2001).*
Assaf Zinger et al., "Proteolytic Nanoparticles Replace a Surgical Blade by Controllably Remodeling the Oral Connective Tissue", ACS nano Issue 12 vol. 2 pp. 1482-1490, Jan. 2018. Retrieved Nov. 22, 2021; https://doi.org/10.1021/acsnano.7b07983.
Joanna E. Adrian et al., "Addressing Liver Fibrosis with Liposomes Targeted to Hepatic Stellate Cells", Journal of Liposome Research, vol. 17 pp. 205-218, 2007. Retrieved Nov. 22, 2021; DOI: 10.1080/08982100701528047.
Aaron Dolor et al., "Digesting a Path Forward: The Utility of Collagenase Tumor Treatment for Improved Drug Delivery", Mol Pharm., vol. 15 Issue 6 pp. 2069-2083, Jun. 2018. Retrieved Nov. 22, 2021; DOI: 10.1021/acs.molpharmaceut.8b00319.
Yiping Li et al., "Inhibition of liver fibrosis using vitamin A-coupled liposomes to deliver matrix metalloproteinase-2 siRNA in vitro", Moleculare Medical Reports, vol. 12 pp. 3453-3461, 2015. Retrieved Nov. 22, 2021; DOI: 10.3892/mmr.2015.3842.
Kohli, A. G.; Kivimae, S.; Tiffany, M. R.; Szoka, F. C., Improving the distribution of Doxil® in the tumor matrix by depletion of tumor hyaluronan. Journal of Controlled Release 2014, 191, 105-114. Retrieved Nov. 22, 2021; http://dx.doi.org/10.1016/j.jconrel.2014.05.019.
Evangelopoulos M, Tasciotti E. Bioinspired approaches for cancer nanotheranostics. Nanomedicine (Lond). Jan. 2017;12(1):5-7. doi: 10.2217/nnm-2016-0374. Epub Nov. 23, 2016. Retrieved Nov. 22, 2021; PMID: 27876435.6.
Patra, C. R.; Bhattacharya, R.; Mukhopadhyay, D.; Mukherjee, P., Fabrication of gold nanoparticles for targeted therapy in pancreatic cancer. Advanced drug delivery reviews 2010, 62 (3), 346-361. Retrieved Nov. 22, 2021; doi: 10.1016/j.addr.2009.11.007.
Yang et al., Liposome based delivery systems in pancreatic cancer treatment: from bench to bedside. Cancer treatment reviews 2011, 37 (8), 633-642. Retrieved Nov. 22, 2021 from: http://dx.doi.org/10.1016/j.ctrv.2011.01.006.
Yu, M. K. et al., Drug-loaded superparamagnetic iron oxide nanoparticles for combined cancer imaging and therapy in vivo. Angewandte Chemie 2008, 120 (29), 5442-5445. Retrieved Nov. 22, 2021; DOI: 10.1002/anie.200800857.
Schroeder, A. et al., Treating metastatic cancer with nanotechnology. Nature Rev. Cancer 2011, 12 (1), 39-50. Retrieved Nov. 22, 2021; DOI: 10.1038/nrc3180.
Kieler-Ferguson, H. M. et al., Encapsulation, controlled release, and antitumor efficacy of cisplatin delivered in liposomes composed of sterol-modified phospholipids. European Journal of Pharmaceutical Sciences 2017, 103, 85-93. Retrieved Nov. 22, 2021; doi: 10.1016/j.ejps.2017.03.003.

(Continued)

*Primary Examiner* — Celeste A Roney
(74) *Attorney, Agent, or Firm* — The Roy Gross Law Firm, LLC; Roy Gross

(57) ABSTRACT

Pharmaceutical compositions comprising at least one lipid-based particle encapsulating a proteolytic enzyme and a pharmaceutically acceptable carrier, wherein the proteolytic enzyme comprises at least 75% proteolytically active enzyme are provided. Methods of using same and producing same are also provided.

20 Claims, 63 Drawing Sheets
(30 of 63 Drawing Sheet(s) Filed in Color)

(56) References Cited

OTHER PUBLICATIONS

He, Z. et al., A high capacity polymeric micelle of paclitaxel: Implication of high dose drug therapy to safety and in vivo anti-cancer activity. Biomaterials 2016, 101, 296-309. Retrieved Nov. 22, 2021 from: http://dx.doi.org/10.1016/j.biomaterials.2016.06.002.

Goodman, T. T., Olive, P. L. & Pun, S. H., Increased nanoparticle penetration in collagenase-treated multicellular spheroids. Int. J. Nanomed. 2007, 2 (2), 265. Retrieved Nov. 22, 2021; PMID: 17722554.

Murty, S. et al., Nanoparticles functionalized with collagenase exhibit improved tumor accumulation in a murine kenograft model. Particle & Particle Systems Characterization 2014, 31 (12), 1307-1312. Retrieved Nov. 22, 2021; DOI: 10.1002/ppsc.201400169.

Woessner, J. F., Matrix metalloproteinases and their inhibitors in connective tissue remodeling. The FASEB Journal 1991, 5 (8), 2145-2154. PMID: 1850705.

Bonnans, C.; Chou, J.; Werb, Z., Remodelling the extracellular matrix in development and disease. Nature reviews. Molecular cell biology 2014, 15 (12), 786-801. Retrieved Nov. 22, 2021; doi: 10.1038/nrm3904.

Iredale, J. P.; Thompson, A.; Henderson, N. C., Extracellular matrix degradation in liver fibrosis: Biochemistry and regulation. Biochimica et Biophysica Acta (BBA)—Molecular Basis of Disease 2013, 1832 (7), 876-883. Retrieved Nov. 22, 2021; http://dx.doi.org/10.1016/j.bbadis.2012.11.002.

Luxenhofer, R.; Schulz, A.; Roques, C.; Li, S.; Bronich, T. K.; Batrakova, E. V.; Jordan, R.; Kabanov, A. V., Doubly amphiphilic poly(2-oxazoline)s as high-capacity delivery systems for hydrophobic drugs. Biomaterials 2010, 31 (18), 1972-4979. Retrieved Nov. 22, 2021; doi: 10.1016/j.biomaterials.2010.02.057.

Richa Jain et al., "Production and partial characterization of collagenase of Streptomyces exfoliatus CFS 1068 using poultry feather", Indian Journal of Experimental Biology, vol. 48 pp. 174-178, Feb. 2010. Retrieved Nov. 22, 2021; PMID: 20455327.

Zheng, X. et al.,. Ultrasound-guided intratumoral administration of collagenase-2 improved liposome drug accumulation In solid tumor xenografts. Cancer Chemother Pharmacol. Jan. 2011;67(1):173-82. doi: 10.1007/s00280-010-1305-1. Epub Mar. 21, 2010. PMID: 20306263. DOI 10.1007/s00280-010-1305-1.

D'Souza, G. G. M. (Ed.). (2017). Liposomes. Methods in Molecular Biology. doi: 10.1007/978-1-4939-6591-5.

Al-Rubaie, M. S., & Abdullah, T. S. (2014). Multi lamellar vesicles (Mlvs) liposomes preparation by thin film hydration technique. Engineering and Tech. J, 32, 550-560. Retrieved Nov. 22, 2021; https://www.iasj.net/iasj/download/3dc699d9c21c29a8.

Ramana LN, Sharma S, Sethuraman S, Ranga U, Krishnan UM. Investigation on the stability of saquinavir loaded liposomes: implication on stealth, release characteristics and cytotoxicity. Int J Pharm. Jul. 15, 2012;431(1-2):120-9. Retrieved Nov. 22, 2021; doi: 10.1016/j.ijpharm.2012.04.054. Epub Apr. 28, 2012. PMID: 22569226.

Protocol for Liposome Preparation Through Thin-film Hydration. (n.d.). Institute for Advancing Translational Medicine in Bone & Joint Diseases (TMBJ). Retrieved Nov. 16, 2021, from https://tmbj.hkbu.edu.hk/images/20130629/13724927885156.pdf.

PCT International Search Report for International Application No. PCT/IL2019/050097, dated May 22, 2019. 4pp.

PCT Written Opinion for International Application No. PCT/IL2019/050097, dated May 22, 2019. 8pp.

PCT International Preliminary Report on Patentability for International Application No. PCT/IL2019/050097, dated Jul. 28, 2020, 9pp.

* cited by examiner 2 min     10 min     25 min

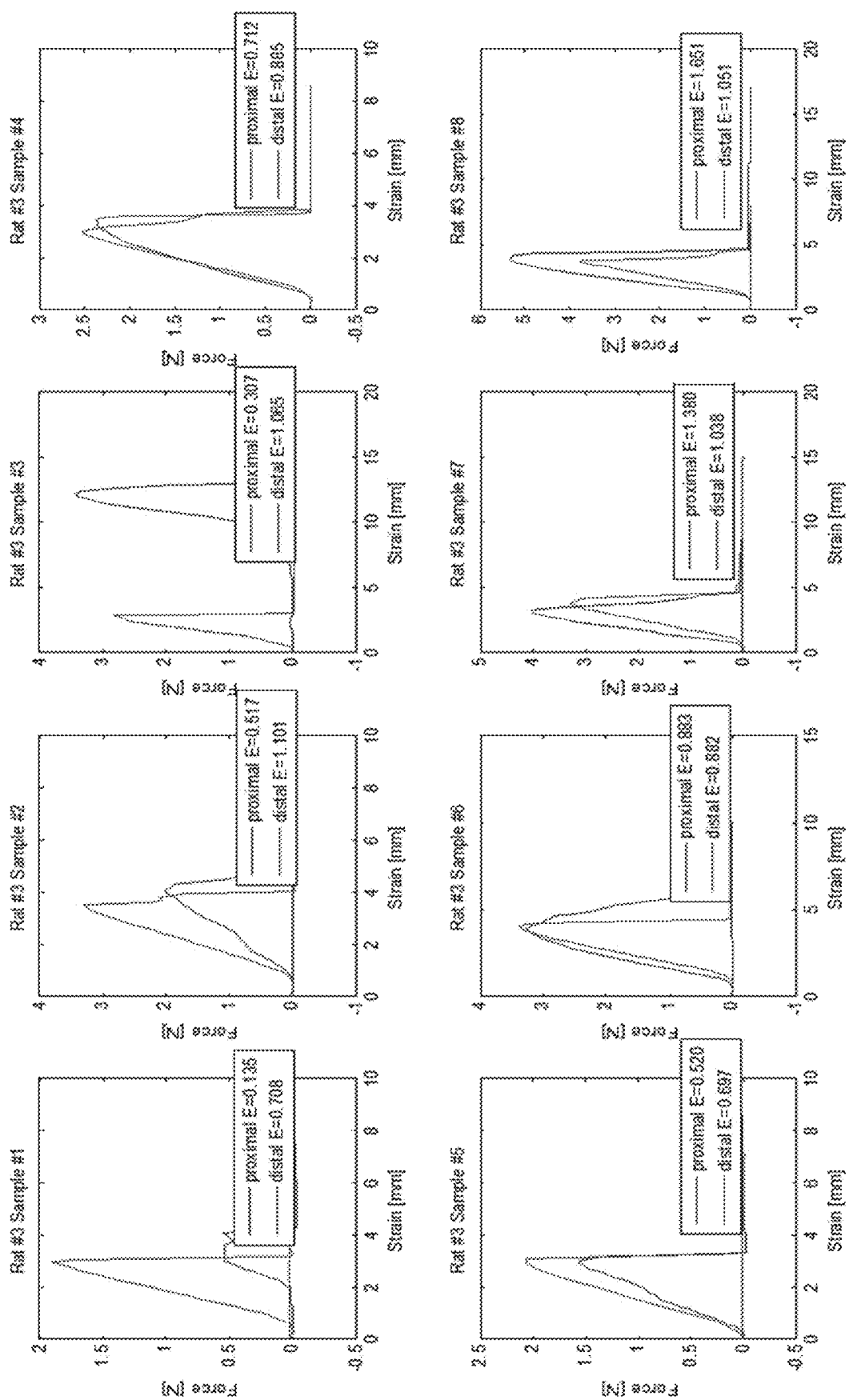
Figure 7H continued_1

Cell growth in the Y-dimension (μm)

Cell growth in the Y-dimension (μm)

Cell growth in the Y-dimension (μm)

| | Total Gd [µg] | SD | Gd/organ [µg/gr] | SD | injected dose [%] | SD |
|---|---|---|---|---|---|---|
| Injected dose | 171.60 | 6.24 | | | 100.00 | |
| Gingival tissue | 0.10 | 0.04 | 15.35 | 7.66 | 0.06 | 0.02 |
| Skin | 0.03 | 0.01 | 0.05 | 0.02 | 0.03 | 0.02 |
| Lungs | 0.15 | 0.04 | 0.07 | 0.02 | 0.08 | 0.03 |
| Brain | 0.03 | 0.01 | 0.02 | 0.01 | 0.02 | 0.01 |
| Spleen | 0.08 | 0.01 | 0.08 | 0.01 | 0.03 | 0.01 |
| Urinary bladder | 0.01 | 0.01 | 0.10 | 0.08 | 0.01 | 0.01 |
| Kidneys | 0.05 | 0.00 | 0.01 | 0.00 | 0.03 | 0.00 |
| Tongue | 0.00 | 0.00 | 0.00 | 0.00 | 0.03 | 0.03 |
| Liver | 0.15 | 0.02 | 0.01 | 0.01 | 0.09 | 0.01 |
| Stomach | 0.00 | 0.05 | 0.00 | 0.00 | 0.02 | 0.01 |
| Digestive System | 0.09 | 0.07 | | | 0.04 | 0.04 |

Figure 9P

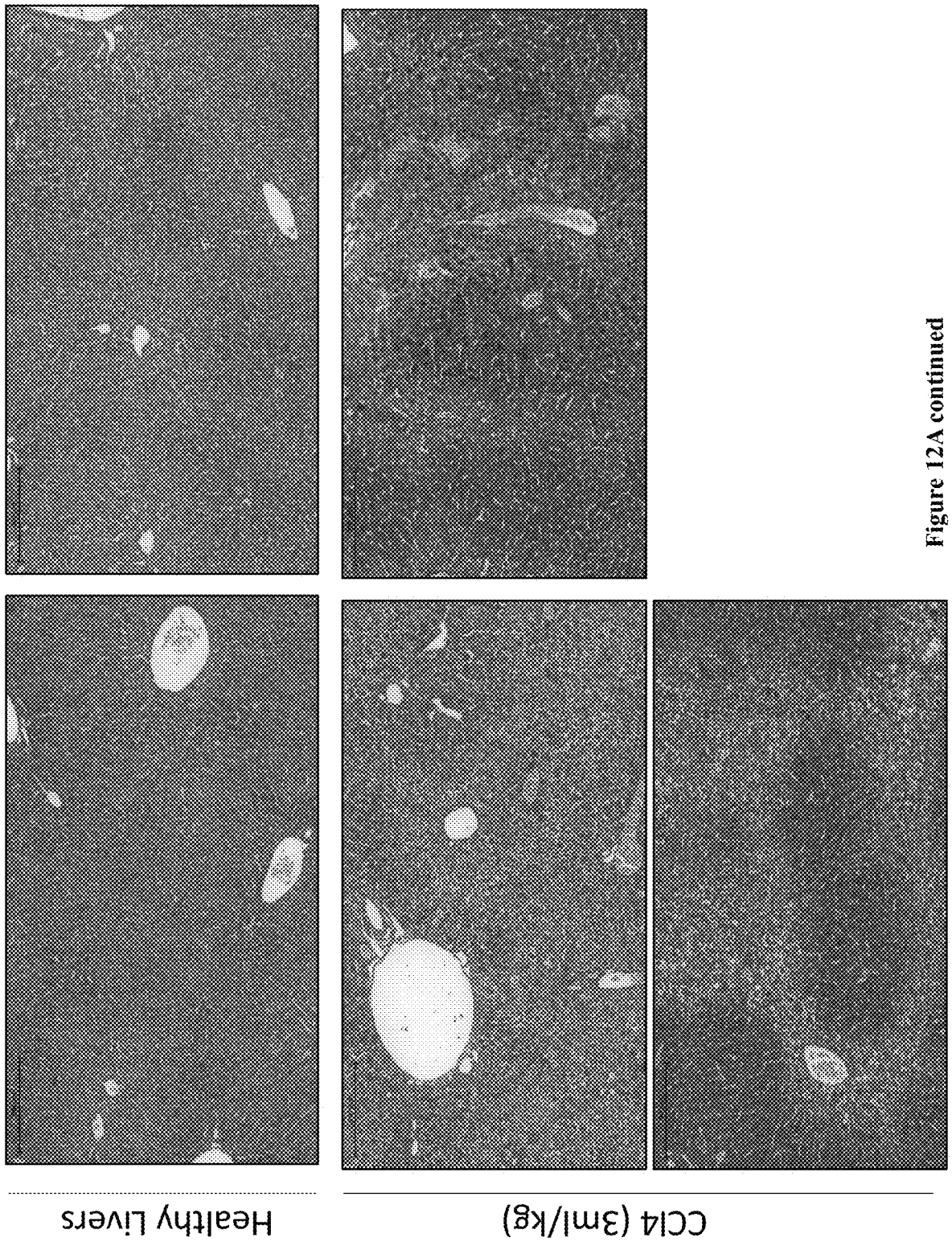

COLLAGENASE LOADED LIPOSOMES FOR ENHANCING DRUG DELIVERY

CROSS-REFERENCE TO RELATED APPLICATIONS

This application is a National Phase of PCT Patent Application No. PCT/IL2019/050097 having International Filing date of Jan. 23, 2019, which claims the benefit of priority of U.S. Provisional Patent Application Nos. 62/620,597 filed on Jan. 23, 2018, entitled "COLLAGENASE NANOPARTICLES ENHANCE THE PENETRATION OF DRUGS INTO PANCREATIC TUMORS" and 62/620,602 filed on Jan. 23, 2018, entitled "PROTEOLYTIC NANOPARTICLES REPLACE A SURGICAL BLADE BY CONTROLLABLY REMODELING THE ORAL CONNECTIVE TISSUE". The contents of the above applications are all incorporated by reference as if fully set forth herein in their entirety.

FIELD OF INVENTION

The present invention is in the field of nanoparticle drug delivery.

BACKGROUND OF THE INVENTION

There are 28 types of collagens in the human body that are tuned for the mechanoelastic function of each organ. Collagenase is a matrix metalloproteinase which is naturally in control of biodegrading collagen in the extracellular matrix and a key player in tissue remodeling processes. Collagenase is clinically-approved for digesting abnormal thickening of the skin and tissues of the palms in patients suffering from Dupuytren's contracture. In order to prevent damage to collagen-containing tissues that surround the treatment site, the enzyme concentration and spatial biodistribution must be carefully controlled.

With less than an 8% five-year survival rate, pancreatic ductal adenocarcinoma (PDAC) remains one of the deadliest cancers with insufficient treatment modalities. One primary reason for this poor prognosis is the excess growth of a fibrotic extracellular matrix (ECM) that surrounds the cancerous cells, limiting the penetration of drugs into the tumor. Such fibrotic ECM is found in numerous cancers. Collagen, a triple-helix protein, is the main structural component in the PDAC's ECM. Collagen's viscoelastic properties play a major role in constructing healthy tissues, but pathologic excess production of collagen can contribute to tumor chemoresi stance.

The ECM of pancreatic tumors generates high interstitial fluid pressures that result in vascular collapse, further limiting drug uptake from circulation. Recent studies have suggested that manipulating the ECM can decrease tumors' drug resistance and improve the outcome of chemotherapy treatments in pancreatic cancer. For example, inhibiting Hedgehog signaling pathways, which are associated with ECM construction, increased the penetration of chemotherapy into the tumor. In another study, a combination therapy of the anti-fibrotic agent pirfenidone, with chemotherapy, also suppressed tumor growth by reducing collagen synthesis through pancreatic stellate cell regulation.

Nanotechnologies promise to revolutionize medical care by improving accuracy and targeting therapeutics to the disease site. To date, more than 80 nanotechnologies have been approved for clinical use. Liposomes, nanoscale vesicles with an inner aqueous core that is surrounded by a lipid bilayer membrane, are clinical drug delivery systems. Tailoring the liposome size and composition modulates biodistribution and controls the drug release profile at the target site. For example, Abraxane, an FDA-approved paclitaxel-loaded 110-nm particle, is used for treating PDAC patients in combination with gemcitabine. Gold nanoparticles, polymeric micelles and liposomes have also been suggested as nanoscale drug delivery systems for treating PDAC. However, the delivery of enzymes, which are frequently less stable and prone to denaturation and deactivation, from liposomes remains a challenge.

Collagenase type-I (Enzyme Commission (EC) number 3.4.24.3) is a water-soluble matrix metalloprotease with specificity towards collagen fibers. Once activated by its natural co-factors, $Ca^{+2}$ and $Zn^{+2}$, the half-life of collagenase varies from tissue to tissue, declining to single minutes when injected into systemic circulation. As such, most therapeutic applications require a formulation to protect the enzyme from early deactivation before reaching the target site. Though numerous formulation methods for protecting small molecule drugs are known, methods of protecting enzymes are less well established. Protocols for producing liposomes are well known, however, the extent to which the act of encapsulation harms the enzyme has never been examined. Methods of producing liposomes that encapsulate enzymes, but do not harm and/or denature the enzyme in the process are greatly needed.

Thus, drug delivery system that disassemble the collagen component of the PDAC ECM, and improved drug uptake, are needed for treating pancreatic tumors and other forms of conditions with difficult to access locations for drugging. More generally, lipid compositions that can protect a therapeutic enzyme and keep that enzyme active for longer periods of time are also needed.

SUMMARY OF THE INVENTION

The present invention provides, in some embodiments, pharmaceutical composition comprising at least one lipid-based particle encapsulating at least one proteolytic enzyme and a pharmaceutically acceptable carrier, wherein at least 75% of the proteolytic enzyme is proteolytically active. Methods of using same and producing same are also provided. Methods of decreasing fibrosis in a subject and of producing liposomes encapsulating enzymes are also provided.

According to a first aspect, there is provided a pharmaceutical composition comprising at least one lipid-based particle encapsulating at least one proteolytic enzyme and a pharmaceutically acceptable carrier, wherein at least 75% of the proteolytic enzyme is proteolytically active.

According to another aspect, there is provided a method of decreasing fibrosis in a subject in need thereof, the method comprising administering to the subject the pharmaceutical composition of the invention, thereby decreasing fibrosis in the subject in need thereof.

According to some embodiments, the carrier is devoid or substantially devoid of ions that activate the proteolytic enzyme.

According to some embodiments, the lipid-based particle is a liposome. According to some embodiments, the liposome comprises 1,2-dimyristoyl-sn-glycero-3-phosphocholine (DMPC). According to some embodiments, the liposome comprises about 40% by molar weight cholesterol. According to some embodiments, the liposome further comprises poly-ethylene glycol (PEG). According to some embodiments, the liposome comprises between 50 and 60%

DMPC, 35 and 45% cholesterol and 3 and 7% 1,2-distearoyl-sn-glycero-3-phosphoethanolamine-N-methoxy-PEG (PEG-DSPE).

According to some embodiments, the pharmaceutical composition comprises at least $1\times10^{10}$ lipid-based particles.

According to some embodiments, the proteolytic enzyme is dissolved in an aqueous solution devoid of ions that activate the proteolytic enzyme.

According to some embodiments, the solution comprises a pH of 8 or above.

According to some embodiments, the proteolytic enzyme is active against collagen. According to some embodiments, the proteolytic enzyme is selected from collagenase, papain and bromelain. According to some embodiments, the proteolytic enzyme is collagenase. According to some embodiments, the collagenase is collagenase I, collagenase II or both.

According to some embodiments, the lipid-based particle comprises a positive charge.

According to some embodiments, the lipid-based particle comprises 1,2-dioleoyl-3-trimethylammoniopropane (Dotap).

According to some embodiments, the lipid-based particle comprises a maximum cross-sectional area of less than 70 square microns.

According to another aspect, there is provided a method of increasing penetrance of a drug into a tumor in a subject in need thereof, the method comprising:
 a. administering to the subject a pharmaceutical composition comprising at least one lipid-based particle encapsulating at least one proteolytic enzyme and a pharmaceutically acceptable carrier; and
 b. administering the drug to the subject,
 thereby increasing the penetrance of the drug into the tumor.

According to some embodiments, the administering the drug occurs at a time after administering the pharmaceutical composition sufficient for degradation of extra cellular matrix (ECM) around the tumor. According to some embodiments, the time after administering the pharmaceutical composition is at least 24 hours. According to some embodiments, administering the pharmaceutical composition comprises administering 2 doses at least 24 hours apart.

According to some embodiments, the drug is encapsulated within a lipid-based particle.

According to some embodiments, administering the pharmaceutical composition does not increase the number of circulating tumor cells in the subject.

According to some embodiments, the tumor is a pancreatic tumor. According to some embodiments, the administering comprises intrapancreatic injection.

According to some embodiments, the drug is a chemotherapeutic. According to some embodiments, the chemotherapeutic is paclitaxel.

According to some embodiments, the increase is at least a doubling in penetrance. According to some embodiments, the increase in penetrance comprises a decrease in tumor size.

According to some embodiments, the fibrosis is selected from the group consisting of: pancreatic fibrosis, lung fibrosis, liver fibrosis and pterygium. According to some embodiments, the decrease in fibrosis is at least a 20% decrease.

According to another aspect, there is provided a method of producing a pharmaceutical composition comprising a liposome encapsulating at least one enzyme, the method comprising:
 a. providing a thin lipid film; and
 b. rehydrating the thin lipid film with a solution comprising the enzyme, wherein the rehydrating produces liposomes encapsulating the enzyme and wherein the solution comprising the enzyme is
  i. devoid of organic solvents;
  ii. devoid of ions that activate the enzyme; and
  iii. is at a temperature below a transition temperature of a lipid in the thin lipid film;
 thereby producing liposomes encapsulating at least one enzyme.

According to some embodiments, the thin lipid film is produced by evaporating a lipid solution dissolved in an organic solvent and wherein the evaporating is performed at a temperature not higher than 37 degrees Celsius.

According to some embodiments, the enzyme is a proteolytic enzyme. According to some embodiments, the proteolytic enzyme is collagenase and the ion that activates the proteolytic enzyme is selected from calcium, zinc and both.

According to some embodiments, the solution comprising the enzyme is below the lowest transition temperature of a lipid in thin lipid film. According to some embodiments, the solution comprising the enzyme is at or below 15 degrees Celsius.

According to some embodiments, the rehydrating does not comprise vortexing, a temperature above 15 degrees Celsius or both.

According to some embodiments, the method further comprises downsizing the liposomes produced in (b) with an extruder, wherein the downsizing is performed at a temperature of not more than 20 degrees Celsius and at a maximal working pressure of not more than 10 bar. According to some embodiments, the downsizing with an extruder comprises passing the liposomes through each of a 400, 200 and 100 nanometer membrane.

According to some embodiments, the method further comprises removing non-encapsulated enzyme by dialysis.

According to some embodiments, at least 75% of the encapsulated enzyme is enzymatically active. According to some embodiments, the method further comprises testing the enzymatic activity of the encapsulated enzyme to ensure that at least 75% of the encapsulated enzyme is enzymatically active.

According to some embodiments, the method is performed at a temperature of not more than 20 degrees Celsius.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
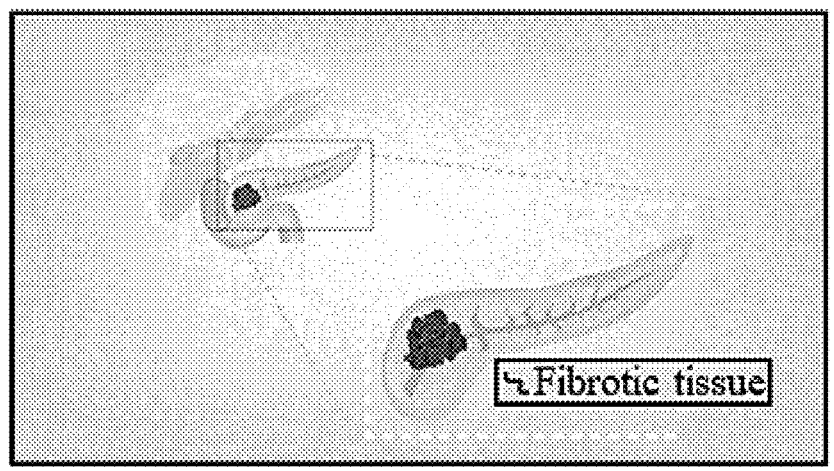
FIGS. 1A-H: Collagenase nanoparticles for treating pancreatic cancer. (1A-D) Schematic outline of the study. (1A) Pancreatic ductal adenocarcinoma (PDAC) is characterized by the overexpression of extracellular matrix (ECM). (1B) The dense ECM contributes to tumor drug resistance. (1C) Proteolytic enzymes, housed within nanoparticles were used to disassemble the collagen component of the tumor ECM. (1D) Collagenase encapsulated liposomes pretreatment increased tumor' drug uptake, allowing more effective treatment. (1E) A bar chart comparing enzyme activity inside the particles and in plasma (E), (n=3). (1F) A line graph showing the effect of varied cholesterol content in liposomes composed of DMPC:cholesterol:DSPE-PEG2000 on prolonging the collagenase release rate at 37° C. (F), (n=3). (1G-H) DSC thermogram (1G) and dynamic light scattering (DLS) size measurements (1H) of DMPC liposomes containing 0, 15 and 39 mol % cholesterol, suspended in PBS pH 7.4. While a sharp transition temperature can be seen 25.5° C. for the 0 mol % cholesterol formulation, no transition temperature is noticed in the 39 mol % formulation. Insignificant size differences were observed between the three liposome formulations. *indicates p-value<0.05, indicates p-value<0.01, and **indicates p-value<0.0001 according to a student's t-test with a two-tailed distribution with unequal variance.
Figure 1B:
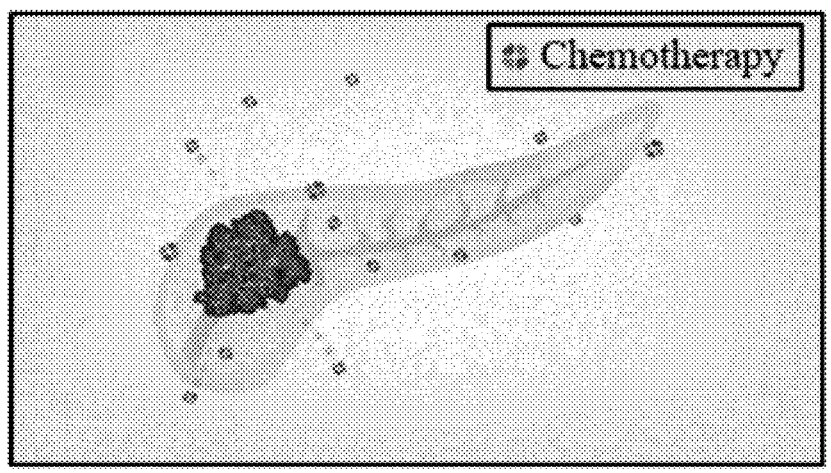
Figure 1C:
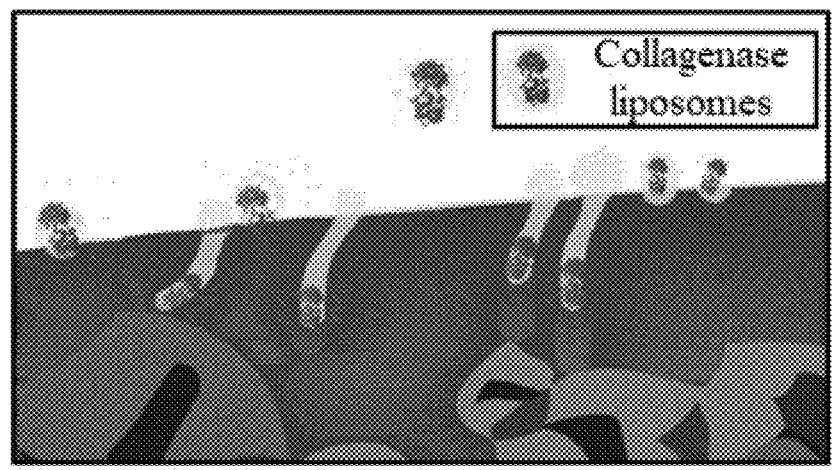
Figure 1D:
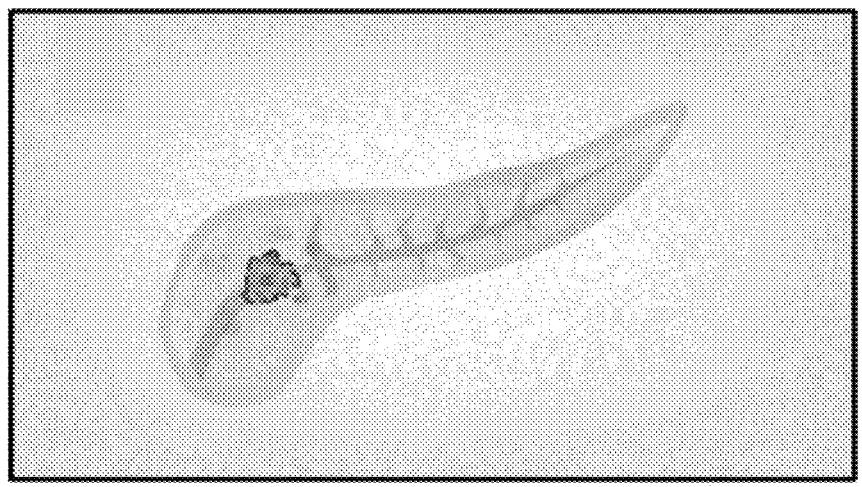

The present invention provides pharmaceutical composition comprising at least one lipid-based particle encapsulating at least one proteolytic enzyme and a pharmaceutically acceptable carrier, wherein at least 75% of the proteolytic enzyme is proteolytically active. Methods of using same and producing same are also provided. Methods of decreasing fibrosis in a subject and of producing liposomes encapsulating enzymes are also provided.

The invention is based on the surprising finding that the known methods of producing lipid-based particles for therapeutic delivery result in severe deactivation/denaturation of an enzyme that is being integrated. Lipid encapsulation of small molecules is well known in the art; however, most small molecules are more stable than enzymes and less susceptible to damage induced by heat and solvents. Further, small molecules do not get deactivated by cofactors, or have the short functional half-lives that enzymes do. Even many simple proteins that might be delivered in lipid-based vesicles do not present the difficulties that enzymes do. It was determined that in order to keep the vast majority of the enzyme functional upon integration into a lipid-based vesicle, the conditions during creation of the vesicle must be closely monitored. The result is a lipid-based vesicle with an extremely high proportion of functional enzyme which makes it a far more effective and efficient delivery system for the enzyme.

Pharmaceutical Compositions

By a first aspect, there is provided a pharmaceutical composition comprising at least one lipid-based particle encapsulating at least one enzyme and a pharmaceutically acceptable carrier, wherein at least 50% of the enzyme is enzymatically active.

In some embodiments, at least 50, 55, 60, 65, 70, 75, 80, 85, 90, 95, 97, 99, or 100% of the enzyme is enzymatically active. Each possibility represents a separate embodiment of the invention. In some embodiments, at least 75% of the enzyme is enzymatically active. In some embodiments, at least 80% of the enzyme is enzymatically active. In some embodiments, at least 85% of the enzyme is enzymatically active. In some embodiments, at least 90% of the enzyme is enzymatically active. In some embodiments, at least 95% of the enzyme is enzymatically active. In some embodiments, at least 97% of the enzyme is enzymatically active. In some embodiments, at least 99% of the enzyme is enzymatically active. In some embodiments, enzymatically active enzyme is functional enzyme. In some embodiments, enzymatically active enzyme is active in at least one enzymatic function of the enzyme. In some embodiments, enzymatically active enzyme is active in all enzymatic functions of the enzyme. In some embodiments, enzymatically active enzyme is non-denatured enzyme. In some embodiments, enzymatically active enzyme has not been deactivated. In some embodiments, enzymatically active enzyme has not contacted an activating cofactor. In some embodiments, the activating cofactor is an ion that activates the enzyme. In some embodiments, an enzymatically active enzyme is capable of enzymatic function upon release from the particle. In some embodiments, an enzymatically active enzyme is capable of enzymatic function upon reaching a target site in a subject.

Assaying for enzymatic activity is well known in the art and the particular assay used will depend on the nature of the enzyme. Such assays can be coupled with standard assays for measuring total protein. Thus, to assess the % functional/active a skilled artisan can take equal total amounts of free enzyme and the encapsulated enzyme and then run a quantitative functional assay. The functionality relative to the free enzyme would be equivalent to the % functional/active protein since the total protein amount is the same. For proteolytic enzymes, for example, equal amounts of the free enzyme and the encapsulated enzyme can be incubated with a target substrate and the percent cleaved substrate produced can be measured. Since equal amount of enzyme were added the ratio of percent cleaved by the encapsulated enzyme over the percent cleaved by the free enzyme will provide the percentage of functional enzyme. Another option is to use a functional assay that gives a readout of amount of functional protein. For a collagen cleaving enzyme, the fluorescamine assay provides amounts of functional enzyme. Similarly, for other enzymes spectrophotometric, fluorometric, calorimetric, chemiluminescent, light scattering and microscale thermophoresis assays can be used to perform quantitative measurements of enzymatic activity. In some embodiments, ELISA assay is used to measure the activity. In some embodiments, an assay selected from a spectrophotometric, fluorometric, calorimetric, chemiluminescent, light scattering and microscale thermophoresis assay is used to measure the activity. In some embodiments, a fluorescamine assay is used to measure collagenase activity. Continuous and/or discontinuous assays may be used. Indeed, any assay that determines for a given amount of enzyme the percentage of functional enzyme present may be used.

Assays and kits for measuring enzyme activity are commercially available and include, but are not limited to, acetylcholinesterase activity kit (Sigma), alcohol dehydrogenase activity kit (Sigma), amylase activity kit (Sigma, Thermo), ATPase/GTPase activity kit (Sigma), beta-secretase activity kit (Sigma, Thermo), collagenase activity kit (Sigma), creatine kinase activity kit (Sigma), DPP4 activity kit (Sigma), GAPDH activity kit (Sigma, Thermo), glucose-6-phosphate dehydrogenase activity kit (Sigma), granzyme B activity kit (Sigma), IDH activity kit (Sigma), lipase activity kit (Sigma), MTP activity kit (Sigma), NADP/NADPH assay kit (Sigma), MMP-3 activity kit (Sigma), MMP-1 activity kit (Sigma), Neutrophil elastase activity kit (Sigma), phospholipase D activity kit (Sigma), pyruvate kinase activity kit (Sigma), ribonuclease A activity kit (Sigma), trypsin activity kit (Sigma), cytochrome P450 activity kit (Thermo), reverse transcriptase activity kit (Thermo), and paraoxonase activity kit (Thermo), to name but a few.

Percent enzymatically active protein should not be confused with total enzymatic activity. Total enzymatic activity can be increased in two ways but having more enzyme and by having more functional enzyme. Thus, a method of producing liposomes can results in greater total enzymatic activity merely by encapsulation more protein. Indeed, a method could increase encapsulation, but at the same time decrease the amount of functional enzyme and thus have no effect on, or even decrease, total enzymatic function. The invention is drawn to lipid-based particles with a high percentage of functional enzyme regardless of the total amount of enzyme encapsulated. This is achieved by producing the liposomes without any organic solvent present, at very low temperatures (even during mixing and extruding), extruding at very low force, and making sure all components are devoid of ions that would prematurely activate the enzyme. These components performed together results in very low amounts of enzyme becoming denatured or deactivated, and thus the percentage of encapsulated protein that is active is very high.

In some embodiments, the enzyme is a proteolytic enzyme. In some embodiments, the proteolytic enzyme is active against collagen. In some embodiments, the proteolytic enzyme is specific to collagen. In some embodiments, the proteolytic enzyme is specific collagen type I. In some embodiments, the proteolytic enzyme is specific to collagen type II. In some embodiments, the proteolytic enzyme is selected from collagenase, papain and bromelain. In some embodiments, the proteolytic enzyme is collagenase. In some embodiments, the proteolytic enzyme is collagenase I. In some embodiments, the proteolytic enzyme is collagenase II. In some embodiments, the proteolytic enzyme is collagenase I, collagenase II or both.

In some embodiments, the collagenase has absolute specificity to Type I collagen, wherein it has neglectable or no detectable catalytic activity to any other fibers. In some embodiments, the collagenase does not have reduced specificity. In some embodiments, the collagenase has not been modified to alter its specificity. In some embodiments, the collagenase has increased potency. In some embodiments, the collagenase has increased potency against extra cellular matrix (ECM) collagen.

In some embodiments, the collagenase at least catalyzes the proteolytic cleavage of Type I collagen. In some embodiments the collagenase is a collagenase Type II. In some embodiments the collagenase is a collagenase Type III. In some embodiments the collagenase is a collagenase Type IV.

In some embodiments, the collagenase targets any collagen. In some embodiments, the collagenase is specific for collagen type I. In some embodiments, the collagenase has absolute specificity for collagen type I. In some embodiments, the collagenase is a mix of collagenases. In some embodiments, the collagenase is not acylated collagenase. In some embodiments, the collagenase is devoid of acylated collagenase. In some embodiments, the lipid particle is devoid of acylated collagenase.

In some embodiments, the pharmaceutical composition comprises a carrier, excipient or adjuvant and is devoid of calcium or zinc. In some embodiments, the pharmaceutical carrier is devoid of an ion that activates the enzyme. In some embodiments, the enzyme is collagenase and the carrier is devoid of calcium, zinc or both.

As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein. In some embodiments, the carrier is substantially devoid of ions that activate collagenase. In some embodiments, the carrier is devoid of ions that activate collagenase. In some embodiments, the ions that activate collagenase are selected from calcium and zinc. In some embodiments, the zinc and/or calcium are zinc and/or calcium ions. In some embodiments, the carrier is devoid of calcium, zinc or both. In some embodiments, the carrier is devoid of calcium. In some embodiments, the carrier is devoid of zinc. In some embodiments, the carrier is devoid of molecules that inhibit collagenase. Many inhibitors of collagenase are known in the art, such as EDTA, known EDTA-like inhibitors and thiols, to name but a few.

In some embodiments, the lipid-based particle is selected from a virosome, an emulsion, an H-II phase particle, a liposome and a micelle. In some embodiments, the lipid-based particle is selected from a liposome and a micelle. In some embodiments, the lipid-based particle is a liposome. In some embodiments, the particle is a nanoparticle. In some embodiments, the lipid is a phospholipid. In some embodiments, the lipid is a glycerophospholipid. In some embodiments, the lipid is a bilayer forming lipid.

In some embodiments, the liposome composition is a composition derived from the composition in International Patent Application WO2015140802, incorporated herein by reference in its entirety. In some embodiments, the method of producing the liposome composition is derived from the method described in WO2015140802. In some embodiments, the lipid composition of the liposomes of the invention is the lipid composition described in WO2015140802, but the enzymatic activity of the enzyme encapsulated is greater than the enzymatic activity of the encapsulated enzyme in WO2015140802. In some embodiments, the liposome is pegylated. In some embodiments, the liposome is not pegylated. In some embodiments, the liposome comprises 1,2-dimyristoyl-sn-glycero-3-phosphocholine (DMPC). In some embodiments, the liposome comprises between 30-80%, 30-70%, 30-65%, 30-60%, 30-55%, 40-80%, 40-70%, 40-65%, 40-60%, 40-55%, 45-80%, 45-70%, 45-65%, 45-60%, 45-55%, 50-80%, 50-70%, 50-65%, 50-60%, 50-55%, 55-80%, 55-70%, 55-65%, or 55-60% DMPC. Each possibility represents a separate embodiment of the invention. In some embodiments, the liposome comprises between 50 and 60% DMPC. In some embodiments, the liposome comprises cholesterol. In some embodiments, the liposome does not comprise cholesterol. In some embodiments, the liposome comprises at least 1, 5, 10, 20, 25, 30, 35, 40, 45, 50, 55, or 60% cholesterol. Each possibility represents a separate embodiment of the invention. In some embodiments, the liposome comprises not more than 1, 5, 10, 20, 30, 40, 50, 60, 70, 80% cholesterol. Each possibility represents a separate embodiment of the invention. In some embodiments, the liposome comprises between 1-20, 1-25, 1-30, 1-40, 1-45, 1-50, 5-20, 5-25, 5-30, 5-40, 5-45, 5-50, 5-60, 10-20, 10-25, 10-30, 10-40, 10-45, 10-50, 10-60, 10-70, 20-25, 20-30, 20-40, 20-45, 20-50, 20-60, 20-70, 20-80, 30-40, 30-45, 30-50, 30-60, 30-70, 30-80%, 35-40, 35-45, 35-50, 35-60, 35-70, or 35-80% cholesterol. Each possibility represents a separate embodiment of the invention. In some embodiments, the liposome comprises between 35 and 45% cholesterol. In some embodiments, the liposome comprises about 40% cholesterol. In some embodiments, the liposome comprises 39% cholesterol. In some embodiments, the percentage of cholesterol is determined by molar weight. In some embodiments, the liposome comprises poly-ethylene glycol (PEG). In some embodiments, the liposome comprises 1,2-distearoyl-sn-glycero-3-phosphoethanolamine-N-methoxy-PEG (PEG-DSPE). In some embodiments, the liposome comprises between 1-10, 1-9, 1-8, 1-7, 1-6, 1-5, 2-10, 2-9, 2-8, 2-7, 2-6, 2-5, 3-10, 3-9, 3-8, 3-7, 3-6, 3-5, 4-10, 4-9, 4-8, 4-7, 4-6, 4-5, 5-10, 5-9, 5-8, 5-7, or 5-6% PEG-DSPE. Each possibility represents a separate embodiment of the invention. In some embodiments, the liposome comprises between 3 and 7% PEG-DSPE. In some embodiments, the liposome comprises about 56% DMPC, 39% cholesterol and 5% PEG-DSPE. In some embodiments, the liposome comprises 56% DMPC, 39% cholesterol and 5% PEG-DSPE. In some embodiments, the liposome comprises between 50 and 60% DMPC, between 35 and 45% cholesterol and between 3 and 7% PEG-DSPE. In some embodiments, the percentage is determined by molar weight.

In some embodiments, the enzyme is dissolved in a solution. In some embodiments, the solution is an aqueous solution. In some embodiments, the aqueous solution is PBS. In some embodiments, the solution is devoid or substantially devoid of an ion that activates the enzyme. In some embodiments, the solution that is added to the enzyme is devoid or substantially devoid of an ion that activates the enzyme. In some embodiments, the aqueous solution hydrates a dehydrated and/or lyophilized powder of the enzyme. In some embodiments, the dehydrated and/or lyophilized powder is devoid of or substantially devoid of an ion that activates the enzyme. In some embodiments, substantially devoid comprises less than 10, 5, 1, 0.5, 0.1, 0.01, 0.001, 0.0001, 0.0001 or 0.00001 parts per million of the ion. Each possibly represents a separate embodiment of the invention. In some embodiments, substantially devoid comprises a contaminate being less than 10, 5, 1, 0.5, 0.1, 0.01, 0.001, 0.0001, 0.0001 or 0.00001% of the composition, solution or lyophilized powder. Each possibly represents a separate embodiment of the invention.

In some embodiments, the solution is cold when added to the enzyme. In some embodiments, cold is at or below 20, 15, 14, 13, 12, 11, 10, 9, 8, 7, 6, 5 or 4 degrees Celsius. Each possibility represents a separate embodiment of the invention. In some embodiments, cold is at or below 10 degrees Celsius. In some embodiments, cold is at or below 4 degrees Celsius. In some embodiments, the solution is basic. In some embodiments, solution comprises a pH at or above 7.2, 7.4, 7.5, 7.6, 7.8, 8, 8.2, 8.5, 8.7, 9, 9.5, or 10. Each possibility represents a separate embodiment of the invention. In some embodiments, solution comprises a pH at or above 8. In some embodiments, solution comprises a pH at or above 10.

In some embodiments, the concentration of enzyme encapsulated within the particle is at least 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, or 2.0 mg/ml. Each possibility represents a separate embodiment of the invention. In some embodiments, the concentration of enzyme added to be encapsulated within the particle is at least 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.6, 0.7, 0.75, 0.8, 0.9, 1.0, 1.1, 1.2, 1.25, 1.3, 1.4, 1.5, 1.6, 1.7, 1.75, 1.8, 1.9, 2.0, 2.5, 3.0, 3.5, 4.0, 4.5, 5.0, 5.5, 6.0, 7.0, 8.0, 9.0, or 10 mg/ml. Each possibility represents a separate embodiment of the invention. In some embodiments, the concentration of collagenase encapsulated by liposomes is sufficient to degrade collagen at ECM of a tumor. In some embodiments, the concentration of collagenase encapsulated by liposomes is sufficient to degrade fibrotic tissue. In some embodiments, the concentration of collagenase encapsulated by liposomes is sufficient to counter balance collagen synthesis by a tumor. In some embodiments, the concentration of collagenase encapsulated by liposomes is sufficient to reduce collagen in the tumor ECM at a rate greater than collagen is synthesized in the tumor ECM. In some embodiments, the amount of encapsulated enzyme is about 0.5, 1, 1.5, 2, 2.5, 3, 3.5, or 4 mg. Each possibility represents a separate embodiment of the invention. In some embodiments, the amount of encapsulated enzyme is less than 0.5, 1, 1.5, 2, 2.5, 3, 3.5, or 4 mg. Each possibility represents a separate embodiment of the invention.

In some embodiments, the composition comprises at least $10^7$, $0.5*10^8$, $10^8$, $0.5*10^9$, $10^9$, $0.5*10^{10}$, $10^{10}$, $0.5*10^{11}$, $10^{11}$ $0.5*10^{12}$, or $10^{12}$ lipid-based particles. Each possibility represents a separate embodiment of the invention. In some embodiments, the composition comprises a sufficient number of particles to degrade collagen at ECM of a tumor. In some embodiments, the composition comprises a sufficient number of particles to degrade collagen at a fibrotic tissue. In some embodiments, the composition comprises a sufficient number of liposomes to counter balance collagen synthesis by a tumor. In some embodiments, the composition comprises a sufficient number of liposomes to reduce collagen in the tumor ECM at a rate greater than collagen is synthesized in the tumor ECM.

In some embodiments, the lipid-based particle comprises a targeting moiety. In some embodiments, the moiety is an ECM-targeting moiety. In some embodiments, the moiety is a pancreas targeting moiety. In some embodiments, the moiety is a tumor targeting moiety. In some embodiments, the moiety targets to a tissue that comprises a tumor. In some embodiments, the moiety is a collagen targeting moiety. The term "moiety", as used herein, relates to a part of a molecule that may include either whole functional groups or parts of functional groups as substructures. The term "moiety" further means part of a molecule that exhibits a particular set of chemical and/or pharmacologic characteristics which are similar to the corresponding molecule.

In some embodiments, the targeting moiety is a protein. In some embodiments, the targeting moiety is a fragment of a protein. In some embodiments, the targeting moiety is an antibody or fragment thereof. In some embodiments, the targeting moiety is an antigen binding fragment. In some embodiments, the targeting moiety is a nano-antibody. In some embodiments, the antibody, antigen binding fragment or nano-antibody is anti-collagen. In some embodiments, the antibody, antigen binding fragment or nano-antibody binds collagen. In some embodiments, the protein is a collagen receptor or fragment thereof. In some embodiments, the protein is the extracellular domain of a collagen receptor. In some embodiments, the protein is the collagen binding region of a collagen receptor. In some embodiments, the protein is von Willebrand factor (VWF). In some embodiments, the fragment is the collagen binding domain of VWF. In some embodiments, the protein is a leucine-rich repeat (LRR) domain-containing protein. In some embodiments, the fragment is the LRR domain. In some embodiments, the fragment is a collagen-binding fragment of the LRR domain. In some embodiments, the LLR domain-containing protein is decorin (DCN). In some embodiments, the fragment comprises repeats 4 to 5 in the LRR domain of DCN. In some embodiments, the protein is a tumor-specific receptor. In some embodiments, the protein is receptor upregulated in a tumor. In some embodiments, the protein is a tumor specific or tumor upregulated surface protein.

In some embodiments, the targeting moiety is anchored in a lipid bilayer. In some embodiments, the targeting moiety is anchored to the outside of a lipid bilayer. In some embodiments, the targeting moiety is part of a chimeric protein that passes through the lipid bilayer. In some embodiments, the targeting moiety is in the extravesical domain of the chimeric protein. In some embodiments, the chimeric protein comprises a transmembrane domain. In some embodiments, the chimeric protein comprises a glycosylphosphatidylinositol (GPI) anchor. In some embodiments, the targeting moiety is coupled to a transmembrane domain or a GPI anchor. Methods of integrating proteins and protein fragments into a lipid bilayer and specifically a liposome are well known in the art. Any such method may be employed. The targeting moiety, or chimeric protein may be integrated into the liposome as it is created.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen.

An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass.

In some embodiments, the lipid-based particle comprises an average diameter that decreases penetration into a cell. In some embodiments, the liposome comprises an average diameter that decreases penetration into an organ. In some embodiments, the liposome comprises an average diameter that decreases penetration through a lipid bilayer. In some embodiments, the average diameter is at least 50, 100, 110, 120, 130, 140, 150, 160, 170, 180, 190, 200, 210, 220, 230, 240, 250, 260, 270, 280, 290, or 300 nanometers (nm). Each possibility represents a separate embodiment of the invention. The upper limit of the liposome diameter would be determined by what is safe for administration into a subject. In some embodiments, the average diameter is not more than 400, 450, 500, 550, 600, 650, 700 or 750 nm. Each possibility represents a separate embodiment of the invention. In some embodiments, the average diameter is between 50-700, 50-650, 50-600, 50-550, 50-500, 50-450, 50-400, 100-700, 100-650, 100-600, 100-550, 100-500, 100-450, 100-400, 150-700, 150-650, 150-600, 150-550, 150-500, 150-450, 150-400, 200-700, 200-650, 200-600, 200-550, 200-500, 200-450, 200-400, 250-700, 250-650, 250-600, 250-550, 250-500, 250-450, or 250-400 nm. Each possibility represents a separate embodiment of the invention. In some embodiments, the average diameter is between 150 and 500 nm. In some embodiments, the average diameter is between 50 and 500 nm. In some embodiments, the average diameter targets, or increases targeting, to a tumor and/or the ECM.

In some embodiments, the lipid-based particle comprises a size that promotes entrance into pterygium. In some embodiments, the-lipid based particle comprises a size that decreases entrance into healthy conjunctiva. In some embodiments, a size that promotes entrance into pterygium is a size that allow the particle to enter a hole with an area of 70 square microns. In some embodiments, a size that promotes entrance into pterygium is a cross-sectional area of less than 70, 69, 68, 67, 66, 65, 64, 63, 62, 61, 60, 59, 58, 57, 56 or 55 square microns. Each possibility represents a separate embodiment of the invention. In some embodiments, a size that promotes entrance into pterygium is an average cross-sectional area of less than 70, 69, 68, 67, 66, 65, 64, 63, 62, 61, 60, 59, 58, 57, 56 or 55 square microns. Each possibility represents a separate embodiment of the invention. Each possibility represents a separate embodiment of the invention. In some embodiments, a size that promotes entrance into pterygium is a maximal cross-sectional area of less than 70, 69, 68, 67, 66, 65, 64, 63, 62, 61, 60, 59, 58, 57, 56 or 55 square microns. Each possibility represents a separate embodiment of the invention. In some embodiments, a size that promotes entrance into pterygium is a cross sectional area of less than 70 square microns. In some embodiments, a size that promotes entrance into pterygium is an average circumference of less than 70 square microns. In some embodiments, a size that promotes entrance into pterygium is a maximal circumference of less than 70 square microns.

In some embodiments, the particle comprises a longitudinal, or rod-like, aspect ratio. In some embodiments, the particle is rod-like. In some embodiments, the particle is ovular. In some embodiments, the particle is longer in one dimension than at least one of the other two dimensions. In some embodiments, the particle is at least 10, 20, 30, 40, 50, 60, 70, 80, 90, 100, 125, 150, 175, 200, 250, or 300% longer. Each possibility represents a separate embodiment of the invention. In some embodiments, the particle is between 10-300, 10-250, 10-200, 10-150, 10-100, 20-300, 20-250, 20-200, 20-150, 20-100, 30-300, 30-250, 30-200, 30-150, 30-100, 40-300, 40-250, 40-200, 40-150, 40-100, 50-300, 50-250, 50-200, 50-150, or 50-100% longer. Each possibility represents a separate embodiment of the invention. In some embodiments, this shape of the particle decreases cellular uptake. In some embodiments, this shape of the particle increases targeting to a tumor and/or the ECM. In some embodiments, an ovular particle comprises a shorter dimension that produces a cross sectional area that is of a size that promotes entrance into pterygium.

In some embodiments, the lipid-based particle comprises a positive charge. In some embodiments, the lipid-based particle comprises a negative charge. In some embodiments, the lipid-based particle comprises no charge. In some embodiments, a positively charged particle comprises 1,2-dioleoyl-3-trimethylammoniopropane (Dotap). In some embodiments, the particle comprises Dotap. In some embodiments, Dotap is added to the lipid composition during production of the lipid-based particle.

In some embodiments, the charge of the liposome targets, or increases targeting to a tumor and/or the ECM. In some embodiments, the charge is positive. In some embodiments, the charge is negative. In some embodiments, the charge is neutral. In some embodiments, the charge is positive or neutral. In some embodiments, the charge is negative or neutral. In some embodiments, the positive charge increases binding to or complex with negatively charged collagenase protein.

In some embodiments, the liposome comprises at least a portion of lipids with an increased chemical affinity to collagen. A skilled artisan will appreciate that the lipids that make up the liposome can be chemically altered by the addition of side groups or head groups and that these groups may have an increased affinity or ability to bind collagen. In some embodiments, a portion is 1, 5, 10, 20, 30, 40, 50, 60, 70, 80, 90, 95, 97 or 100% of the lipids in the liposome. Each possibility represents a separate embodiment of the invention. In some embodiments, the chemical alteration is addition of an aldehyde group. In some embodiments, the chemical alteration is addition of an amine. In some embodiments, the chemical alteration is addition of a carboxylic acid or derivative thereof. In some embodiments, the at least a portion comprises an aldehyde group, amine or carboxylic acid. In some embodiments, the added group is added to the outside of the lipid bilayer. In some embodiments, the added group is added to the head group of a lipid. Other groups, moieties, or reactive species that increase the affinity of a lipid to collagen may be used.

In some embodiments, the lipid-based particle comprises at least one proteolytic enzyme. In some embodiments, the lipid-based particle comprises only one enzyme. In some embodiments, the lipid-based particle comprises only one proteolytic enzyme. In some embodiments, the lipid-based particle further comprises at least one other enzyme. In some embodiments, the lipid-based particle encapsulates the at least one other proteolytic enzyme. In some embodiments, the lipid-based particle further comprises a molecule that inhibits ECM formation. In some embodiments, the lipid-based particle further comprises a molecule that degrades ECM. In some embodiments, the other proteolytic enzyme is a matrix degrading metalloproteinase (MMP). In some embodiments, the other proteolytic enzyme degrades collagen. In some embodiments, the MMP is a hyaluronidase. In some embodiments, the MMP is a gelatinase. In some embodiments, the MMP is a stromelysin. Examples of other proteolytic enzymes that degrade ECM include, but are not limited to hyaluronidase, papain, pepsidase, and gelatinase.

Methods of Use

By another aspect, there is provided a method of increasing penetrance of a drug into a tumor in a subject in need thereof, the method comprising: administering to the subject a pharmaceutical composition comprising at least one lipid-based particle encapsulating at least one proteolytic enzyme and a pharmaceutically acceptable carrier, thereby increasing the penetrance of the drug into the tumor.

By another aspect, there is provided a method for treating a tumor in a subject in need thereof the method comprising administering to the subject a pharmaceutical composition comprising at least one lipid-based particle encapsulating at least one proteolytic enzyme and a pharmaceutically acceptable carrier, and administering a drug to the subject, thereby treating the tumor.

By another aspect, there is provided a method of treating pterygium in a subject in need thereof, the method comprising administering to the subject a pharmaceutical composition comprising at least one lipid-based particle encapsulating at least one proteolytic enzyme and a pharmaceutically acceptable carrier, thereby treating pterygium in the subject in need thereof.

By another aspect, there is provided a method of decreasing fibrosis in a subject in need thereof, the method comprising administering to the subject a pharmaceutical composition of the invention, thereby decreasing fibrosis in the subject in need thereof.

By another aspect, there is provided use of a pharmaceutical composition comprising at least one lipid-based particle encapsulating at least one proteolytic enzyme and a pharmaceutically acceptable carrier for at least one of:
 a. decreasing fibrosis in a subject in need thereof;
 b. increasing penetrance of a drug into a tumor in a subject in need thereof;
 c. treating pterygium in a subject in need thereof; and
 d. treating a tumor comprising tumor associated fibrosis in a subject in need thereof.

In some embodiments, the method is for use in increasing penetrance of a drug into a tumor in the subject in need thereof, and the method comprises after administering the pharmaceutical composition further administering the drug to the subject, thereby increasing the penetrance of the drug into the tumor. In some embodiments, the method further comprises administering the drug to the subject.

In some embodiments, the pharmaceutical composition comprising at least one lipid-based particle encapsulating at least one proteolytic enzyme and a pharmaceutically acceptable carrier is a pharmaceutical composition of the invention.

In some embodiments, the subject is a mammal. In some embodiments, the subject is a human. In some embodiments, the subject is a veterinary animal. In some embodiments, the subject suffers from cancer. In some embodiments, the subject has a tumor. In some embodiments, the tumor is a pancreatic tumor. In some embodiments, the cancer is pancreatic cancer. In some embodiments, the tumor comprises tumor associated fibrosis. In some embodiments, the tumor is characterized by tumor associated fibrosis. In some embodiments, the subject suffers from a condition characterized by fibrosis. In some embodiments, the subject suffers from a fibrotic condition. In some embodiments, the fibrosis or fibrotic condition is selected from the group consisting of: pancreatic fibrosis, lung fibrosis, liver fibrosis, cancer associated fibrosis and pterygium. In some embodiments, the fibrosis is pancreatic fibrosis. In some embodiments, the fibrosis is pterygium. In some embodiments, the fibrosis is cancer associated fibrosis.

As used herein, the term "pterygium" refers to a growth of the conjunctiva or mucous membrane that covers the white part of the eye. In some embodiments, the growth in a pathological growth. In some embodiments, the growth is over the cornea. In some embodiments, the growth obscures the iris. In some embodiments, pterygium comprises collagen. In some embodiments, pterygium comprises collagen I. In some embodiments, pterygium comprises collagen II. In some embodiments, pterygium comprises collagen I and II. In some embodiments, the pharmaceutical composition used for treating pterygium comprises a lipid-based particle comprising a maximum cross-sectional area of less than 70 square microns. In some embodiments, the pharmaceutical composition used for treating pterygium comprises lipid-based particles with an average cross-sectional area of less than 70 square microns.

As used herein, the terms "cancer associated fibrosis" and "tumor associated fibrosis" are used synonymously and interchangeably and refer to fibrotic growth in and/or around a solid cancer or tumor. In some embodiments, cancer associated fibrosis is characterized by pro-fibrotic signaling. In some embodiments, cancer associated fibrosis comprises increased ECM around a tumor. In some embodiments, cancer associated fibrosis occurs in the tumor microenvironment (TME). In some embodiments, tumor associated fibrosis decreases drug penetrance into the tumor. In some embodiments, the tumor comprises tumor associated fibrosis.

As used herein, the terms "administering," "administration," and like terms refer to any method which, in sound medical practice, delivers a composition containing an active agent to a subject in such a manner as to provide a therapeutic effect. One aspect of the present subject matter provides for intravenous administration of a therapeutically effective amount of a composition of the present subject matter to a patient in need thereof. Other suitable routes of administration can include parenteral, subcutaneous, oral, intramuscular, or intraperitoneal.

The dosage administered may be dependent upon the age, health, and weight of the recipient, kind of concurrent treatment, if any, frequency of treatment, and the nature of the effect desired.

In some embodiments, the administering is systemic administration. In some embodiments, the administering is intertumoral injection. In some embodiments, the administering is intrapancreatic injection. In some embodiments, the administering is to the ECM of the tumor. In some embodiments, the administering is to the TME of the tumor.

In some embodiments, administering the pharmaceutical composition comprises administering at least 1, 2, 3, 4, 5, 6, or 7 doses. Each possibility represents a separate embodiment of the invention. In some embodiments, the administration is administering at least 2 doses. In some embodiments, the 2 doses are at least 6, 12, 18, 24, 36 or 48 hours apart. Each possibility represents a separate embodiment of the invention. In some embodiments, the administering is administering 2 doses about 24 hours apart. In some embodiments, the administering is administering 2 doses about 48 hours apart. In some embodiments, the administering is administering 2 doses about 24-48 hours apart. In some embodiments, administering the pharmaceutical composition does not increase or substantially increase the number of circulating tumor cell in the subject.

In some embodiments, the administering the drug occurs at a time after administering the pharmaceutical composition sufficient for degradation of ECM around the tumor. In some embodiments, the administering the drug occurs at a time after administering the pharmaceutical composition sufficient for degradation of fibrosis around the tumor. In some embodiments, the administering the drug occurs at a time after administering the pharmaceutical composition sufficient for degradation of collagen around the tumor. In some embodiments, the time after administering said pharmaceutical composition is at least 12, 18, 24, 30, 36, 40, 48, 50, 56, 60, 66, 70 or 72 hours. Each possibility represents a separate embodiment of the invention. In some embodiments, the time after administering said pharmaceutical composition is at least 24 hours. In some embodiments, the time after administering said pharmaceutical composition is at least 48 hours.

In some embodiments, the increase penetrance comprises at least a 5, 10, 15, 20, 25, 30, 35, 40, 45, 50, 55, 60, 65, 70, 75, 80, 85, 90, 95, 100, 120, 140, 150, 160, 180, 200, 250, 300, 350, 400, 450, or 500% increase in penetrance. Each possibility represents a separate embodiment of the invention. In some embodiments, the increase is at least a doubling in penetrance. In some embodiments, the increase in penetrance comprises a decrease in tumor size. In some embodiments, the decrease is at least a 5, 10, 15, 20, 25, 30, 35, 40, 45, 50, 55, 60, 65, 70, 75, 80, 85, 90, 95, 97, 99 or 100% decrease in size. Each possibility represents a separate embodiment of the invention.

In some embodiments, the method further comprises administering the drug to the subject. As used herein, a drug refers to any reagent that can affect a positive outcome for the subject. A drug can be for non-limiting example, a small molecule, an antibody a protein or even a cell. Cell based therapies are also considered herein drugs. In some embodiments, the drug is an anti-tumor drug. In some embodiments, the drug is a chemotherapeutic drug. In some embodiments, the chemotherapeutic is paclitaxel. In some embodiments, the anti-tumor drug is an antibiotic. Anti-tumor drugs are well known in the art and include, but are not limited to chemotherapeutics, antibiotics, immune checkpoint drugs, antibody therapies, CAR-T and CAR-NK cells and cytotoxic molecules. Any and all of anti-tumor drugs and therapeutics such as are known in the art may be used. In some embodiments, the drug is encapsulated in a lipid-based particle. In some embodiments, the drug is encapsulated in a nanoparticle. In some embodiments, the drug is encapsulated in a micelle. In some embodiments, the drug is encapsulated in a liposome. In some embodiments, the lipid-based particles are lipid-based particles such as are described hereinabove.

In some embodiments, administering the drug occurs after administering the pharmaceutical composition. In some embodiments, the drug and pharmaceutical composition are administered together. In some embodiments, the drug is administered at a time after administering the pharmaceutical composition sufficient for degradation of ECM around the tumor. In some embodiments, at least 1, 2, 3, 5, 10, 15, 20, 25, 30, 35, 40, 45 or 50% of the ECM around the tumor is degraded. Each possibility represents a separate embodiment of the invention. In some embodiments, the time after administering the pharmaceutical composition is at least 6, 12, 18, 24, 36 or 48 hours. Each possibility represents a separate embodiment of the invention. In some embodiments, the time after administering the pharmaceutical composition is about 24 hours.

As used herein, the terms "treatment" or "treating" of a disease, disorder, or condition" encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life. In some embodiments, treating comprises reducing the size of a tumor. In some embodiments, treating does not comprise increasing the number of circulating tumor cells in the subject.

Methods of Production

By another aspect, there is provided a method of producing a pharmaceutical composition comprising a liposome encapsulating at least one enzyme, the method comprising:
 a. providing a lipid solution dissolved in an organic solvent;
 b. evaporating the solvent to form a thin lipid film; and
 c. rehydrating the thin lipid film with a solution comprising the enzyme, wherein the rehydrating produces liposomes encapsulating the enzyme and wherein the solution comprising the enzyme is
   i. devoid of organic solvents;
   ii. devoid of ions that activate the enzyme; and
   iii. comprises a temperature below a transition temperature of a lipid in the lipid solution;
thereby producing liposomes encapsulating at least one enzyme.

By another aspect, there is provided a method of producing a pharmaceutical composition comprising a liposome encapsulating at least one enzyme, the method comprising:
 a. providing a thin lipid film; and
 b. rehydrating said thin lipid film with a solution comprising said enzyme, wherein said rehydrating produces liposomes encapsulating said enzyme
thereby producing liposomes encapsulating at least one enzyme.

In some embodiments, the pharmaceutical composition is a pharmaceutical composition of the invention.

In some embodiments, the thin lipid film is produced by evaporating a lipid solution dissolved in an organic solvent.

In some embodiments, the solvent is chloroform. In some embodiments, the organic solvent is not an alcohol. In some embodiments, the organic solvent is not ethanol, methanol or both. In some embodiments, the evaporating is performed at a temperature not higher than 37 degrees Celsius. In some embodiments, the thin lipid film is chilled to 4 degrees Celsius before step b.

Thin lipid films are well known in the art and can be produced by applying a lipid solution to a solid surface and evaporating away any liquid so that a thin film forms. The thickness of the film can be modified by the amount of lipids added or by the area on which they are allowed to adhere. In some embodiments, the lipid solution and/or lipid film comprises 1,2-dimyristoyl-sn-glycero-3-phosphocholine (DMPC). In some embodiments, the lipid solution and/or lipid film comprises between 30-80%, 30-70%, 30-65%, 30-60%, 30-55%, 40-80%, 40-70%, 40-65%, 40-60%, 40-55%, 45-80%, 45-70%, 45-65%, 45-60%, 45-55%, 50-80%, 50-70%, 50-65%, 50-60%, 50-55%, 55-80%, 55-70%, 55-65%, or 55-60% DMPC. Each possibility represents a separate embodiment of the invention. In some embodiments, the lipid solution and/or lipid film comprises between 50 and 60% DMPC. In some embodiments, the lipid solution and/or lipid film comprises cholesterol. In some embodiments, the lipid solution and/or lipid film does not comprise cholesterol. In some embodiments, the lipid solution and/or lipid film comprises at least 1, 5, 10, 20, 25, 30, 35, 40, 45, 50, 55, or 60% cholesterol. Each possibility represents a separate embodiment of the invention. In some embodiments, the lipid solution and/or lipid film comprises not more than 1, 5, 10, 20, 30, 40, 50, 60, 70, 80% cholesterol. Each possibility represents a separate embodiment of the invention. In some embodiments, the lipid solution and/or lipid film comprises between 1-20, 1-25, 1-30, 1-40, 1-45, 1-50, 5-20, 5-25, 5-30, 5-40, 5-45, 5-50, 5-60, 10-20, 10-25, 10-30, 10-40, 10-45, 10-50, 10-60, 10-70, 20-25, 20-30, 20-40, 20-45, 20-50, 20-60, 20-70, 20-80, 30-40, 30-45, 30-50, 30-60, 30-70, 30-80%, 35-40, 35-45, 35-50, 35-60, 35-70, or 35-80% cholesterol. Each possibility represents a separate embodiment of the invention. In some embodiments, the lipid solution and/or lipid film comprises between 35 and 45% cholesterol. In some embodiments, the lipid solution and/or lipid film comprises about 40% cholesterol. In some embodiments, the lipid solution and/or lipid film comprises 39% cholesterol. In some embodiments, the percentage of cholesterol is determined by molar weight. In some embodiments, the lipid solution and/or lipid film comprises poly-ethylene glycol (PEG). In some embodiments, the lipid solution and/or lipid film comprises 1,2-distearoyl-sn-glycero-3-phosphoethanolamine-N-methoxy-PEG (PEG-DSPE). In some embodiments, the lipid solution and/or lipid film comprises between 1-10, 1-9, 1-8, 1-7, 1-6, 1-5, 2-10, 2-9, 2-8, 2-7, 2-6, 2-5, 3-10, 3-9, 3-8, 3-7, 3-6, 3-5, 4-10, 4-9, 4-8, 4-7, 4-6, 4-5, 5-10, 5-9, 5-8, 5-7, or 5-6% PEG-DSPE. Each possibility represents a separate embodiment of the invention. In some embodiments, the lipid solution and/or lipid film comprises between 3 and 7% PEG-DSPE. In some embodiments, the lipid solution and/or lipid film comprises about 56% DMPC, 39% cholesterol and 5% PEG-DSPE. In some embodiments, the lipid solution and/or lipid film comprises 56% DMPC, 39% cholesterol and 5% PEG-DSPE. In some embodiments, the lipid solution and/or lipid film comprises between 50 and 60% DMPC, between 35 and 45% cholesterol and between 3 and 7% PEG-DSPE. In some embodiments, the percentage is determined by molar weight. In some embodiments, the lipid solution and/or lipid film is a 50 mM lipid mixture. In some embodiments, the lipid solution and/or lipid film is a 100 mM lipid mixture. In some embodiments, the lipid solution and/or lipid film comprises 50 mM DMPC. In some embodiments, the lipid solution and/or lipid film comprises 100 mM DMPC.

Evaporation can be performed with a speed vac, a rotary evaporator or the equivalent. In some embodiments, a rotary evaporator is used. In some embodiments, the pressure for evaporating is at or below 120 mbar. In some embodiments, evaporating produces a lipid film devoid of organic solvent. In some embodiments, evaporating produces a lipid film substantially devoid of organic solvent.

In some embodiments, the enzyme is a proteolytic enzyme. In some embodiments, the enzyme is collagenase. In some embodiments, the enzyme is collagenase and the ion that activates the proteolytic enzyme is selected from calcium, zinc and both. In some embodiments, the enzyme is collagenase and the ion that activates the proteolytic enzyme is calcium. In some embodiments, the enzyme is collagenase and the ion that activates the proteolytic enzyme is zinc. In some embodiments, the enzyme is collagenase and the ion that activates the proteolytic enzyme is calcium and zinc. Many enzymes require an ionic cofactor in order to be enzymatically active. Each enzyme has its own cofactor and the solution can be made to be devoid or substantially devoid of that cofactor. In some embodiments, the ion is selected from calcium, zinc and both. In some embodiments, the ion is calcium. In some embodiments, the ion is zinc. In some embodiments, the ion is calcium and zinc. In some embodiments, calcium is Ca2+. In some embodiments, zinc is Zn2+.

In some embodiments, the rehydrating produces liposomes encapsulating the enzyme. In some embodiments, the liposomes form naturally during rehydration. In some embodiments, the rehydrating does not comprise vortexing. In some embodiments, the rehydrating comprises suspension of the thin lipid film in the solution comprising the enzyme. In some embodiments, the rehydrating comprises spinning. In some embodiments, the rehydrating is performed with a rotary evaporator. In some embodiments, the evaporation is not turned on. In some embodiments, the rehydration is performed at or below 15 degrees Celsius. In some embodiments, the rehydration is performed for about 30 minutes. In some embodiments, the rehydration is performed for between 20 and 40 minutes. In some embodiments, the rehydration is performed for at least 30 minutes. In some embodiments, the rehydrating does not comprise vortexing, a temperature above 15 degrees Celsius or both.

In some embodiments, the solution comprising the enzyme is devoid or substantially devoid of organic solvents. In some embodiments, the solution comprising the enzyme is devoid of organic solvents. In some embodiments, the solution comprising the enzyme is substantially devoid of organic solvents. In some embodiments, the solution comprising the enzyme is devoid of ions that activate the enzyme. In some embodiments, the solution comprising the enzyme is substantially devoid of ions that activate the enzyme. In some embodiments, the solution comprising the enzyme is devoid or substantially devoid of ions that activate the enzyme. In some embodiments, the solution comprising the enzyme comprises a temperature below a transition temperature (Tm) of a lipid in the thin lipid film. In some embodiments, the solution comprising the enzyme comprises a temperature below the lowest Tm of a lipid in the thin lipid film. In some embodiments, the comprises a temperature below a Tm of a lipid in the thin lipid film is below 25, 20, 15, 10, 5 or 4 degrees Celsius. Each possibility represents a separate embodiment of the invention. In some embodiments, a temperature below a Tm of a lipid in the thin lipid film is below 15 degrees Celsius. In some embodiments, the solution comprising the enzyme is at or below 25, 20, 15, 10, 5 or 4 degrees Celsius. Each possibility represents a separate embodiment of the invention. In some embodiments, the solution comprising the enzyme is at or below 15 degrees Celsius. In some embodiments, the solution comprising the enzyme is at least one of:

i. devoid of organic solvents;
ii. devoid of ions that activate said enzyme;
iii. comprising a temperature below a transition temperature of a lipid in said thin lipid film; and
iv. i, ii and iii.

As used herein, the term "transition temperature" refers to the temperature at which a lipid transitions from a solid to a liquid or liquid to a solid. It is a well-defined physical characteristic of a lipid and well known to one skilled in the art. In some embodiments, the solid phase is an ordered gel phase. In some embodiments, the liquid phase is a disordered liquid crystalline phase. Transition temperatures of lipids and in particular phospholipids can be found on many websites, including for example avantilipids.com/tech-support/physical-properties/phase-transition-temps/.

In some embodiments, the method further comprises downsizing the liposomes produced. In some embodiments, the method further comprises downsizing the liposomes produced in with an extruder. In some embodiments, the downsizing is performed at a temperature of not more than 20 degrees Celsius. In some embodiments, the downsizing is performed at a temperature of not more than 25, 20, 15, 10, 5, or 4 degrees Celsius. Each possibility represents a separate embodiment of the invention. In some embodiments, the downsizing is performed at a maximal working pressure of 10 bar. In some embodiments, the downsizing is performed at a maximal working pressure of 15, 10, 7, 5, 3 or 1 bar. Each possibility represents a separate embodiment of the invention.

In some embodiments, downsizing with an extruder comprises passing the liposomes through each of a 400, 200 and 100 nanometer membrane. In some embodiments, downsizing with an extruder comprises passing the liposomes through a 100-nanometer membrane. In some embodiments, downsizing with an extruder comprises passing the liposomes through a 200-nanometer membrane. In some embodiments, downsizing with an extruder comprises passing the liposomes through a 400-nanometer membrane. In some embodiments, downsizing with an extruder comprises passing the liposomes through at least one of a 400, 200 and 100 nanometer membrane.

In some embodiments, the method further comprises removing non-encapsulated enzyme. In some embodiments, the method further comprises removing non-encapsulated enzyme by dialysis. In some embodiments, the dialysis is performed with the solution in which the enzyme was dissolved. In some embodiments, the solution used for dialysis is cold. In some embodiments, the dialysis is repeated at least 2 or 3 times. In some embodiments, the carrier is exchanges at least 1, 2 or 3 times. Each possibility represents a separate embodiment of the invention. In some embodiments, each subsequent exchange occurs after 24 hours. In some embodiments, all exchanges are with cold solution.

In some embodiments, at least 50, 55, 60, 65, 70, 75, 80, 85, 90, 95, 97, 99, or 100% of the encapsulated enzyme is enzymatically active. Each possibility represents a separate embodiment of the invention. In some embodiments, at least 75% of the encapsulated enzyme is enzymatically active. In some embodiments, at least 80% of the encapsulated enzyme is enzymatically active.

In some embodiments, the method further comprises testing the enzymatic activity of the encapsulated enzyme to ensure that at least the desired percentage of the encapsulated enzyme is enzymatically active. In some embodiments, the method further comprises testing the enzymatic activity of the encapsulated enzyme to ensure that at least 75% of the encapsulated enzyme is enzymatically active. In some embodiments, the method further comprises testing the enzymatic activity of the encapsulated enzyme to ensure that at least 80% of the encapsulated enzyme is enzymatically active. Tests for measuring the percentage of enzymatically active enzyme are described hereinabove.

In some embodiments, the entire method is performed at cold temperature. In some embodiments, the method is performed at or below 20 degrees Celsius.

The definitions of certain terms as used in this specification are provided herein. Unless defined otherwise, all technical and scientific terms used herein generally have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

As used in this specification and the appended claims, the singular forms "a", "an" and "the" include plural referents unless the content clearly dictates otherwise. For example, reference to "a nucleic acid" includes a combination of two or more nucleic acids, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods
Collagenase Liposomes, Ethanol Method

Collagenase type-I (Sigma-Aldrich, St. Louis, Mo., USA) was encapsulated in 100-nm liposomes. A lipid mixture of 1,2-dimyristoyl-sn-glycero-3-phosphocholine (DMPC; Avanti Polar Lipids, Alabaster, Ala., USA), cholesterol (Sigma-Aldrich) and 1,2-di stearoyl-sn-glycero-3-phosphoethanolamine-N-methoxy-polyethylene glycol 2000 (PEG-DSPE; Avanti), at three different molar ratios of: 95:0:5, 80:15:0 and 56:39:5, respectively, were dissolved in absolute ethanol. The lipid solution was added to calcium free Dulbecco's Phosphate Buffer Saline (PBS; Sigma-Aldrich) solution containing 2 mg/ml or 4 mg/ml collagenase to reach a lipid concentration of 50 mM, at 50° C. The liposomes were downsized using a Lipex extruder (Northern Lipids, Vancouver, Canada) five times through each 400, 200 and 100-nm polycarbonate etched membrane (Whatman, Newton, Mass., USA) at 40° C. with a maximal working pressure of 10 bar. The non-encapsulated protein was removed by dialysis using a 1000 kDa cutoff membrane (Spectrum Labs, Calif., USA) against PBS solution (1:1000 vol ratio); the external PBS was replaced after 1, 3 and 24 hours, at 4° C. Liposomes were sized using a Zetasizer NanoZSP (Malvern Instruments, Worcestershire, UK) using disposable polystyrene cuvettes after diluting the samples 1:100 in PBS.

Collagenase Liposomes, Cold Thin-Film Method

Collagenase type-I (Sigma-Aldrich, St. Louis, USA) was encapsulated in 100-nm liposomes using the cold thin film method. A 50 mM lipid mixture of 1,2-dimyristoyl-sn-glycero-3-phosphocholine (DMPC; (Avanti Polar Lipids, Alabaster, Ala., USA), cholesterol (Sigma-Aldrich) and 1,2-distearoyl-sn-glycero-3-phosphoethanolamine-N-methoxy-polyethylene glycol 2000 (PEG-DSPE; Avanti), at molar ratio of 56:39:5 was dissolved in chloroform. The solvent was evaporated using Buchi rotary evaporator (Switzerland) at 37° C. The pressure was lowered to 120 mbar and the process continued until all the solvent was evaporated and thin film was formed. The film was rehydrated with ice cold collagenase solution in calcium free Dulbecco's Phosphate Buffer Saline (PBS; Sigma-Aldrich) using rotary evaporator at 15° C. for 30 min. The liposomes were downsized using a Lipex extruder (Northern Lipids, Vancouver, Canada) five times through each 400, 200 and 100-nm polycarbonate etched membrane (Whatman, Newton, Mass., USA) at 20° C. with a maximal working pressure of 10 bar. The non-encapsulated protein was removed by dialysis using a 1000 kDa cutoff membrane (Spectrum, CA, USA) against cooled PBS solution (1:1000 v/v); the external PBS was replaced after 1, 3 and 24 hours, at 4° C. Liposomes were sized using a Zetasizer NanoZSP (Malvern Instruments, Worcestershire, UK) using disposable polystyrene cuvettes after diluting the samples 1:100 in PBS.

Figure 10:
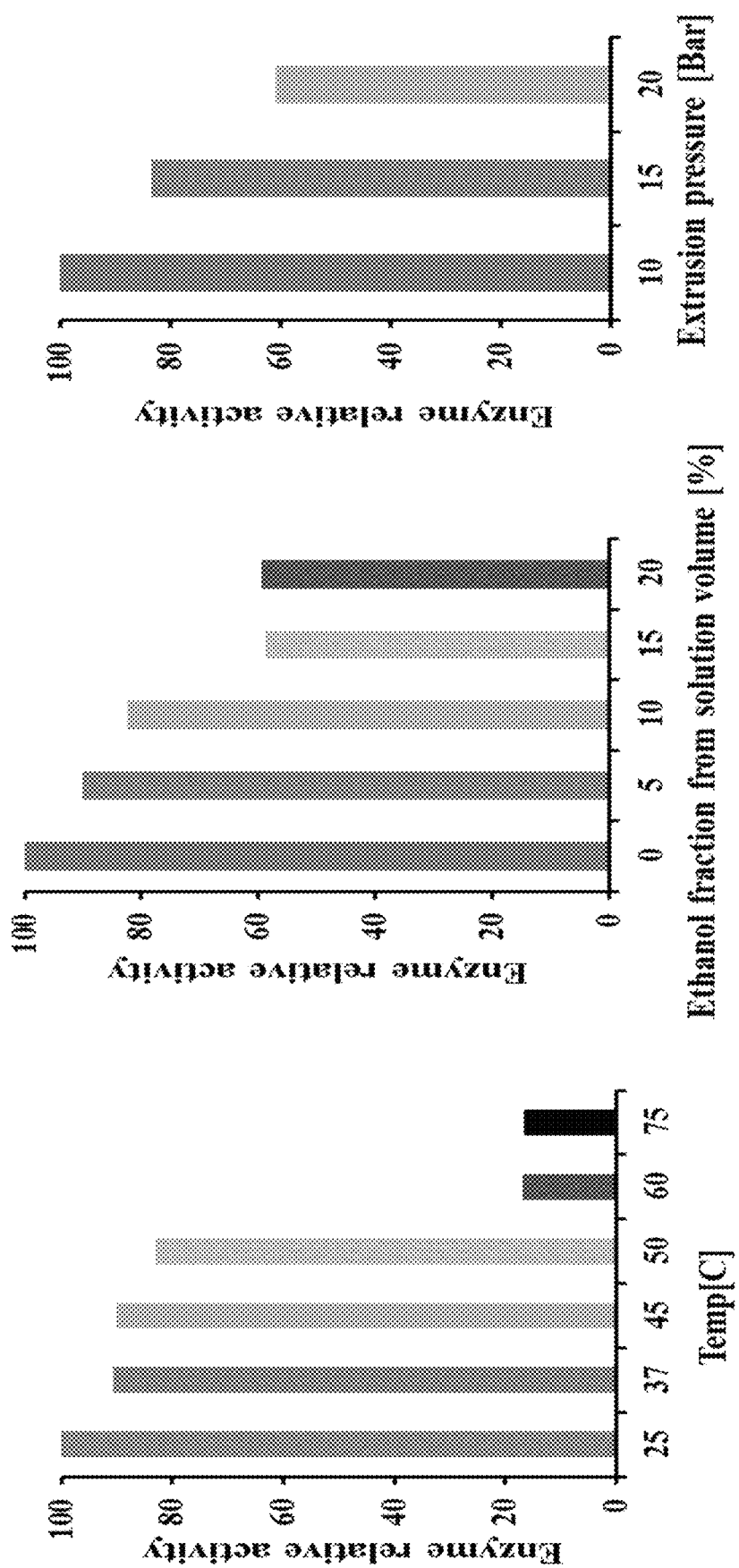
FIG. 10: Collagenase activity test assists in collagenase encapsulation characterization. Bar charts showing activity of the enzyme under different liposome preparation conditions: temperature, ethanol concertation, and extrusion pressure.

Collagenase encapsulation measurement. Collagenase-encapsulated liposomes were dissociated using 1% triton-x 100 in PBS. The mixture was placed in an Eppendorf shaker at 55° C. at 300 rpm for one hour to dissociate the liposomes. The mixture was centrifuged for 10 minutes at 12,000 rpm at 4° C. The liposome-free supernatant was collected and centrifuged again for 10 minutes at 12,000 rpm at 4° C. The protein concentration was determined one of two ways, either using a MicroBCA Protein Assay Kit (ThermoFisher Scientific, MA, USA) or by fluorescamine assay. For the MicroBCA Assay, protein concentration was measured by absorbance at 562 nm using the Infinite 200PRO multimode reader (TECAN, Mannedorf, Switzerland). For the fluorescamine assay, protein concentration was measured on a NanoDrop fluorospectrometer. Encapsulation efficiency reached 10% which is equivalent to collagenase concentration of 0.2 mg/ml inside the liposomes. To load the enzyme without compromising its activity, a maximal working temperature of 50° C., extrusion pressure of 10 bar, and ethanol content below 10% v/v was used (FIG. 10).

Collagenase activity assay. Collagenase type-I activity was determined using gelatin with fluorescein conjugate as a substrate (ThermoFisher). Collagenase (100 µl) was mixed with 80 µl of reaction buffer (0.05M Tris-HCl, 0.15M NaCl, 5 mM CaCl2, 0.2 mM sodium azide at pH 7.6) and 20 µl of 0.125 mg/ml gelatin diluted in PBS. The fluorescent intensity was measured every 15 seconds over a period of 3 minutes at 485 nm and 530 nm (excitation/emission) using an Infinite 200PRO. Collagenase activity was measured at 37° C., where plasma or PBS served as control.

Collagenase release profile. Collagenase release from the liposomes was measured using dialysis tubes 1000 kDa molecular cutoff (SpectraPor) against PBS (1:15 vol ratio) at 37° C. with 100 rpm shaking. Triplicates vials were used for each liposome formulation. The released protein concentration was determined using MicroBCA Protein Assay Kit (ThermoFisher).

Alternatively, Collagenase release was assessed using a Micro BCA Protein Assay Kit (Thermo Fisher Scientific, MA, USA). To separate between the encapsulated and released collagenase, the liposomal solutions for the different experimental time points (1-50 hours) were ultra-centrifuged for 45 minutes with the following parameters: 4° C., 45,000 RPM. After the centrifugation the supernatants were incubated with Triton X-100 diluted to 1% for 1.5 hour at room temperature. Another 13,000 RPM centrifuge was done before the Micro BCA assay.

To test the collagenase activity, liposomal collagenase after dialysis or free collagenase in phosphate buffered saline at a concentration of 5 ug/ml, were incubated at 37° C. Every hour, a collagenase sample was assessed for its capacity to cleave a fluorescein conjugated gelatin substrate (Thermo Fisher). Activity of the released collagenase was determined in accordance to the change in fluorescence over 3 minutes, relative to the fluorescence at t=0.

Gd-rhodamine liposomes. Gadolinium diethylenetriaminepentaacetate (Gd; Sigma-Aldrich) was incorporated into 100-nm liposomes. A lipid mixture of hydrogenated soybean phosphatidylcholine (HSPC; Avanti) cholesterol (Sigma-Aldrich), 1,2-dipalmitoyl-sn-glycero-3-phosphoethanolamine-N-(lissamine rhodamine B sulfonyl (Rhod-DSPE; Avanti) and PEG-DSPE (Avanti) at a molar ratio of 55.94:39:0.06:5 respectively were dissolved in absolute ethanol at 70° C. The dissolved lipids were quickly injected into a PBS solution containing 270 mg/ml of Gd, at 70° C., to reach a lipid concentration of 50 mM. The liposomes were extruded five times through 100-nm polycarbonate membranes (Whatman) at 70° C. The free Gd was removed by dialysis in a 12-14 kDa membrane (Spectrum Laboratories) against PBS solution at 4° C. for 24 hours. Liposomes were sized using a Zetasizer NanoZSP (Malvern).

Gd release profile. Gd release profile from the liposomes was measured by dialysis using 14 kDa cutoff membrane (SpectraPor) loaded with the Gd-liposomes against PBS at a 1:15 vol ratio at 37° C. and 100 rpm shaking. Released Gd was measured using the elemental analysis 5110 ICP-OES (Agilent, CA, USA) at wavelengths of 335.048 and 342.246 nm.

Gd Liposome concertation measurements. Gd-liposome' concentration (liposomes/mL) was measured using a NanoSight NS300 (Malvern, Worcestershire, UK) equipped with a sCMOS camera. Slider shutter and gain were set to 1206 units and 366 respectively, total number of 749 frames were captured with 25 frames per seconds rate. The temperature was set to 24.4° C.

Gd-rhodamine liposome biodistribution. Mice bearing PDAC, 6 weeks after the initiation of the tumor model were administered, via tail vein injection, 400 µl of 1.2 mg/ml Gd-liposomes. Mice were sacrificed at different time intervals: 1, 8, 14 and 24 hours post administration and their organs were collected. Tissues were combusted for 5 hours at 550° C. and then dissolved in 1% vol nitric acid. Gadolinium in each organ was quantified using ICP-EOS (Agilent) at wavelengths of 335.048 and 342.246 nm.

Alternatively, five male Wistar rats were applied 50 µl of the Gd-liposomes in the rat's periodontal pocket. The rats were sacrificed 24-hours after the liposomes placement and the gingival tissue, skin, lungs, brain, spleen, urinary balder, kidneys, tongue, liver, stomach and digestive system were collected. Tissues were combusted for 5 hours at 550° C. and then dissolved in 1% vol nitric acid. Gadolinium in each organ was quantified using ICP-EOS at wavelengths of 335.048 and 342.246 nm (FIG. 9L-P).

Differential Scanning Calorimetry. DSC measurements were performed using a NanoDSC (TA Instruments, New Castle, Del., USA). Liposome suspensions were measured at temperatures ranging from 10 to 65° C. with intervals of 0.5° C./min. PBS was used as a reference buffer.

Tissue culture. KPC cells were established in the laboratory of Surinder K. Batra and derived from pancreatic adenocarcinoma tumors of KrasG12D;Trp53R172H;Pdx1-Cre (KPC) transgenic mice. Cells were cultured in Dubalco Modified Eagle's medium (DMEM; Sigma-Aldrich) supplemented with 10% fetal bovine serum (FBS, Biological Industries, CT, USA), 100 IU ml-1 Penicillin, 100 μg ml-1 Streptomycin and 2 mM L-glutamine (Biological Industries) and grown at 37° C.; 5% $CO_2$. KPC cells expressing the fluorescent protein mCherry were developed by the Satchi-Fainaro Laboratory at the Tel Aviv University, and cultured in DMEM medium, supplemented with 10% fetal bovine serum 1% 2 mM L-glutamine and 1% 100 U penicillin with 0.1 mg/ml streptomycin or 10 μg/ml of puromycin at 37° C. and 5% CO2. All cells tested negative for mycoplasma (EZ-PCR, Mycoplasma test kit, Biological industries).

PDAC model. All the animal studies were approved by, and complied with, the institutional and ethical committee at the Technion. Animal' well-being was monitored daily by certified veterinarians at the Technion facility.

Several mouse models have been developed to study pancreatic cancer, each with its similarities and differences to the disease manifestations in humans. Here, we chose to test our approach on C57BL/6 mice bearing KPC (KrasLSL.G12D/+; p53R172H/+; PdxCretg/+) tumors implanted orthotopically in the pancreas. Specifically, these tumors resemble human pancreatic adenocarcinoma in their excess expression of extracellular collagen.

Ten-week-old C57BL/6 mice (Harlan Laboratories, Jerusalem, Israel) were anesthetized using Ketamine/Xylazine (100 mg/kg and 10 mg/kg-body-weight, respectively) injected intraperitoneally. A subcutaneous injection of 0.05 mg/kg buprenorphine was performed before the surgery. The mice were placed on 37° C. warmed pads. The lateral, abdominal left side of the mice was shaved, and a 1-cm longitudinal cut was performed above the pancreas in the skin. While observing the spleen and the pancreas 1-cm cut was done in the peritoneum. The pancreas was then secured using forceps. 250,000 KPC-mCherry cells were suspended in 0.01 ml at 4° C. PBS and were injected using 5 μl Hamilton syringe with 30 G at 30 degrees using a point style 4 needle (Hamilton, Nev., USA) to the pancreas. Cuts were sutured using 5-0 degradable sutures (Vicryl, AR, USA).

Collagen analysis after the collagenase treatment. Pancreatic tumors were harvested from tumor bearing mice, six weeks after the initiation of the tumor model. Each tumor was sliced horizontally to 1 cm thick slices. All the extracted slices were mixed and randomly chosen for different treatments groups. Treatments included incubation in DMEM medium (Sigma-Aldrich) with collagenase type-I (Sigma-Aldrich) at increasing concentrations: 0.05, 0.1 or 0.2 mg/ml for either 8 or 24 hours. Following the enzymatic treatment, the tumor slices were sectioned, fixated in 10% formalin (Sigma-Aldrich) and stained with Masson's trichrome. Computerized morphometry was utilized to quantitate the fraction of the fibrotic area out of the total area of the tumor in each sample. Computerized morphometry of the collagen was used to determine fibrosis fraction within each sample. Masson's trichrome staining was performed to identify the pancreatic fibrosis. Then, stained slides were entirely scanned at magnification of X20 using the Panoramic MIDI automatic digital slide scanner (3DHistech, Budapest, Hungary). The whole slide was analyzed in Image Pro Premier 9.2 software (Media Cybernetics, MD, USA). Fibrosis area was calculated according to the blue staining within the tissue, and the tissue area was calculated by choosing the whole tissue with the machine 'color picker tool'.

The effect of the collagenase treatment on pancreatic uptake of Gd-liposomes. Mice were treated with two injections of collagenase-liposomes, 24 hours apart (n=4 mice). Control groups included injections of empty liposomes (n=10 mice), free collagenase (n=5 mice) or no injection at all (n=3 mice) instead of collagenase encapsulating liposomes. Twenty-four hours after the second treatment, 400 μl of Gd-liposomes were injected intravenously to the tail vein. 24 hours later, the animals were euthanized, and their organs were harvested. The amount of Gadolinium in each organ was analyzed using elemental analysis (ICP-EOS, Agilent) at wavelengths of 335.048 and 342.246 nm. The organs were harvested, weighed and then burnt at 550° C. overnight. The burnt organs were dissolved in 5 ml of 1% nitric-acid and filtered using 22 μm filters (Millipore Millex-GV, Merck, Darmstadt, Germany). The Gd concentration in the organs was measured using an ICP-EOS elemental analysis.

In-Vivo Imaging

Intra-vital microscopy. Mice were anesthetized using ketamine/xylazine. 300 μl of Gd-rhodamine liposomes were injected intravenously to the tail vein. One-hour after the injection, a 1-cm incision was performed above the pancreas. An SZX16 microscope equipped with a CY3 filter and SDF PLAPO 0.5× PF lens (Olympus, Pa., USA) was used at an exposure time of 365 ms; the threshold was determined by the auto-fluorescence of the healthy pancreas. Image editing of +20% brightness and contrast was performed.

MRI hardware and animal monitoring. Magnetic resonance imaging (MRI) was performed using a 9.4T bore scanner (Bruker Biospec, Ettlingen, Germany), equipped with a Transmit/Receive cylindrical volume coil (72 mm inner diameter). Animals were anesthetized using 0.5-1.5% isoflurane, supplemented with oxygen (0.7 l/min). Respiration was monitored during imaging (Small Animal Instruments, Stony Brook, N.Y., USA) and body temperature was maintained using thermostat-regulated circulating hot water. T2-weighted images were first obtained to identify the pancreas location using a RARE sequence with respiratory gating (0.6 mm thickness, 25 slices, FOV=6×3 cm, matrix dimension=256×128, TR/TE=600/16.2 ms, 3 averages). Gd-liposomes were imaged using T1-weighted RARE sequence with respiratory gating (0.6 mm thickness, 13 slices, FOV=6×3 cm, matrix dimension=256×128, TR/TE=1200/16.2 ms, 3 averages), sequences were acquired every 2 min over 25 min. Image analysis was performed using MRI-Tool—an in-house Matlab based analysis software developed by the Biomedical Core Facility (BCF), The Bruce Rappaport Faculty of Medicine, Technion, Israel Institute of Technology. The MRI figures in the paper were +20% contrast and brightness adjusted.

Micro-CT scan. Mice were imaged using an IVIS Spectrum CT Pre-clinical in-vivo imaging system (PerkinElmer, MA, USA) with the following parameters: CT was set to 50 ms, total projections were 720, voltage was set to 50 kV while the current to 1 mA the binning was determined to 2 and the X-ray filter was set to 440 A1. Hounsfield calibration was performed in air-0.004168 and water-0.5513. Two groups of tumors bearing mice (n=5 each) were divided to control and test group. The mice were weighed weekly and tumor progression was monitored by weekly IVIS scans (PerkinElmer). Epi-fluoresce scans were acquired under the following parameters: excitation 570 nm, emission 620 nm, at 3 seconds exposure. Therapeutic treatment began four weeks after the initial tumor cells injection. The test group received 300 µl dose of collagenase encapsulated liposomes for two consecutive days, while the control group remained untreated. On the third day, both groups received a single dose of 10 mg/kg micellar paclitaxel. Tumor dimensions were assessed using the ROI tool in the IVIS imaging software (Living Image, PerkinElmer).

Rats from the braces only group and from the braces plus nano-surgery group were sacrificed and the head and jaw were scanned using a Skyscan 1176 Micro-CT (Bruker, UK) equipped with an NRecon 1.6.9.8. at a 32-micron resolution under a 70 kV 355 uA source voltage, 90 msec exposure and 0.8 deg rotation step.

PDACs' ECM SEM scanning. For SEM images, the pancreas samples were divided into three groups: treated, cancerous and non-cancerous. Then, each pancreas was cut into small pieces and decellularized by 2-24 hours rounds agitation in a 1% sodium dodecyl sulfate (Sigma-Aldrich) and 0.1% Penicillin/Streptomycin (Biological Industries) in PBS. Subsequently, the samples were washed in distilled water, lyophilized and sputter-coated with gold in a Polaron E5100 coating apparatus (Quorum technologies, Lewis, UK) and observed under JSM-840A SEM (JEOL, Tokyo, Japan).

Paclitaxel micelles. All substances used for polymerization, specifically methyl trifluoromethylsulfonate (MeOTf), 2-n-buty-2-oxazoline (BuOx) and benzonitrile (PhCN) were refluxed over $CaH_2$ and distilled and stored under argon. The polymerization and work-up procedures were carried out as has described in the art. Briefly, 1.91 g (11.6 mmol; 1 eq) MeOTf was added to a dried and nitrogen flushed flask and dissolved in 250 mL PhCN. 34.6 g (407 mol; 35 eq) of 2-methyl-2-oxazoline (MeOx) was added and the reaction mixture was heated to 100° C. for 4 hours. Reaction progress was controlled by FTIR- and 1H-NMR-spectroscopy. After complete consumption of MeOx, the mixture was cooled to RT and 29.4 g (232 mol; 20 eq) 2-n-butyl-2-oxazoline (BuOx) was added. The reaction mixture was heated to 100° C. overnight. The procedure was repeated with 34.6 g (407 mol; 35 eq) MeOx and termination was carried out with 3.0 g (35.2 mmol; 3 eq) piperidine (Pip) at 50° C. for 4 hours. Subsequently, 1.92 g (13.9 mmol; 1 eq) of $K_2CO_3$ was added and the mixture was stirred at 50° C. for 4 hours. Precipitates were removed by centrifugation and the solvent removed under reduced pressure. The supernatant was transferred into a dialysis bag (MWCO 1 kDa, cellulose acetate) and dialyzed against Millipore water overnight. The solution was recovered from the bag and lyophilized. Drug loaded polymer micelles were prepared using the thin film method. Ethanolic polymer (50 g/L) and paclitaxel (20 g/L) stock solutions were mixed in desired ratio. After complete removal of the solvent at 55° C., the films were dried further in vacuo (≤0.2 mbar) overnight. Subsequently, preheated (37° C.) $H_2O$ (Millipore) was added to obtain final polymer and drug concentrations of P2/PTX=50/40 g/L. Complete solubilization was facilitated by shaking the solutions at 55° C. for 30 min. Non-solubilized drug (if any) was removed by centrifugation for 5 min at 10.000 rpm with a Universal 320 R centrifuge, Hettich (Tuttlingen, Germany).

Detection of circulating tumor cells (CTCs) from mouse blood by Flow Cytometry. Blood was sampled from the facial vein of mice from 3 different groups: (i) normal, (ii) mCherry-labeled tumor-bearing mice and (iii) mCherry-labeled tumor-bearing mice treated with liposomes (n=4 mice per group). Blood (20 µl) was collected into an anticoagulant (EDTA)-containing tube, diluted 1:5 with PBS (Sigma-Aldrich) and incubated with anti-mouse CD326 (EpCAM) APC eFlour 780 (cat #47-5791-80, eBioscinces, 0.125 µg per sample) and anti-mouse CD45 FITC (cat #11-0451-82, eBioscinces, 0.5 µg per sample) for 1 hour at room temperature protected from light. Blood samples were diluted with PBS 1:10 (vol ratio) and DAPI 5 µg/ml was added. CTCs in diluted blood samples were detected using flow cytometry (Attune NxT, Life Technologies, ThermoFisher) and analyzed with Kaluza (Beckman Coulter, Ind., USA) software. Briefly, mCherry signal and monoclonal antibodies were used to detect mCherry-labeled CTCs population with the following phenotype: mCherry+/EpCAM+/CD45−. DAPI was used to distinguish apoptotic and dead cells from viable cells. After acquisition of at least 300,000 cells per sample (whole sample was run) analyses were done on singlet cells. Percentages of live cells with the phenotype mCherry+/EpCAM+/CD45− is shown. Positive staining was defined as being greater than non-specific background staining and was verified on blood sample that was spiked-in with mCherry-labeled cells.

Metastasis Detection. Mice were sacrificed, and the brain, lungs, liver and spleen were extracted and held in culture media (Roswell Park Memorial Institute medium; Sigma-Aldrich) at 4° C. until initiating the organ's dissociation. Subsequently, the organs were enzymatically and physically dissociated using a GentleMacs machine (Miltenyi Biotec, Bergisch Gladbach, Germany) and tumor mouse dissociation kit (Miltenyi Biotec) following the machine dissociation protocols. Single cell suspension was obtained by passing the suspension in 70 µm cell strainer (BD Biosciences, CA, USA). After dissociating the organs into a single-cell suspension, the mCherry KPC cells were detected in the mCherry channel, after acquisition of at least 100,000 cells per sample using a flow activated cell sorter (FACS; FACSARIA III, BD Biosciences) and analyzed with Diva (BD Biosciences) software. Proper gates of single cells and positive populations were obtained prior to the analysis.

Blood panels Tumor-bearing mice (n=4 mice per group) were divided to control not treated and test groups. The test groups were treated with two consecutive, day after day, collagenase encapsulated liposomes 300 µl intravenous injections. 24 hours after the second collagenase liposomes injection blood was collected from the groups, 65 µl from each mouse, and the samples were kept in 1 ml lithium heparin and 0.5 ml k3EDTA tubes. Analysis was performed using: VetscanVs2 (Abaxis, CA, USA), i-STAT portable clinical analyzer (Abaxis) and ProCyte Dx* Hematology Analyzer (IDEXX, Maine, USA).

Histology Mice were euthanized at the sampling day. Tumors were extracted and kept in 10% natural buffer formalin (Sigma-Aldrich) at 4° C. for 24 hours before they were paraffin embedded. The slides were deparaffinized and soaked in xylene for 3 minutes, xylene:ethanol 1:1 (vol ratio) for 3 minutes, absolute ethanol for 3 minutes, 95% ethanol for 3 minutes, 70% ethanol for 3 minutes, 50% ethanol for 3 minutes and then rinsed with tap water. Nuclei blue fluorescent staining was performed using NucBlue Fixed Cell ready probes (ThermoFisher) that was added for 10 minutes followed by rinsing with tap water. Hematoxylin and eosin (H&E) and Masson's trichrome (MTC) staining for collagen evaluation was performed.

Alternatively, after sacrificing the rats, the entire maxilla was extracted and kept in 10% Natural Buffer Formalin (NBF) at room temperature. Paraffin-embedded tumor blocks from the rat maxillas were prepared and sectioned in 4 μm-thick slides and stained with hematoxylin-eosin (H&E). Axial and sagittal cuts from the upper jaw were observed.

Fluorescent histology. The stained slides were scanned and analyzed using a 3D Histech Panoramic MIDI scanner (3D Histech, Budapest, Hungary) using an X20 objective magnification, exposure times of 100 msec for the DAPI channel, and 350 msec for the CY3 channel. Images were analyzed using a FIJI Image Analysis software program to evaluate the levels of rhodamine in the tissue. Image editing of +40% brightness and contrast was done.

Statistics. Statistical analysis was performed using F-test for variances to test if the different populations have the same variance. Differences between experimental groups were evaluated using an unpaired, two-tailed distribution Student's t-test. Differences were considered significant at a $p<0.05$. Bar graphs and average values present data as means±standard deviations of the mean.

Cryo-TEM. Cryogenic-temperature transmission electron microscopy (cryo-TEM) was used to image the liposomes, as described by Talmon. We used an FEI Talos 200C, field emission gun (FEG)-equipped with high-resolution TEM. The samples were mounted on Gatan 626 cryo-holders to maintain cryo-preservation in the TEM at -180° C. Images were recorded with a FEI Falcon III camera, the contrast was enhanced using a Volta Phase Plate.

Particle' biodistribution: Liposome biodistribution studies were performed on male Wistar rats using a whole animal Maestro in-vivo imaging machine (Cambridge Research & Instrumentation, MA, USA) excitation: 671-705 nm, emission: 800 nm long pass, exposure time 5000 ms.

ICG (indocyanin green) was encapsulated in multi-lamellar liposomes by dissolving 1,2-dimyristoyl-sn-glycero-3-phosphocholine (DMPC, Avanti Polar Lipids, Alabaster, Alabama) cholesterol (Sigma-Aldrich, St. Louis, USA) and DSPE-PEG (2000) (Avanti), 56:39:5 mole ratio in absolute ethanol. The lipid mixture was hydrated in phosphate buffered saline containing 1.8 mg/ml ICG, to form multi-lamellar liposomes. To produce unilamellar liposomes the liposomes were extruded at 45° C. using a high-pressure Lipex extruder (Northern Lipids, Vancouver, Canada) and sequential passaging through Nuclepore polycarbonate membrane membranes (Whatman, Newton, Mass., USA) with a pore diameter of 800, 400, 200, and 100-nm. Five extrusion steps were applied per filter type. Non-encapsulated ICG was removed using a $1\times10^6$ MWCO dialysis bag (SpectraPor) against PBS at 4° C. for 24 hours. The florescent liposomes were applied to 5 male Wistar rats on each side of the 1st upper molar, 50 μl to each side, and the animals were images before and 1, 4, 8, 12, 24-hours post application. For each measurement, the rats were sacrificed, dissected, and the organs were imaged separately. Fluorescent intensity values were normalized to the highest signal in all organs and background was removed.

Thin Layer Chromatography (TLC). Liposomes, with or without collagenase, were dissolved in methanol, spot-loaded onto silica-gel 60-F254 TLC plates (Merck) and placed in a TLC chamber with chloroform-methanol-water solution (75:20:5) as the mobile phase. The plate was held until the mobile phase reached a critical height, versus all 4 of their components separately: collagenase, cholesterol, PEG-2000 and DMPC.

Collagenase activity assay. Collagenase activity was assessed using fluorescein conjugated gelatin (ThermoFisher) as a substrate. The enzyme solution was added to the substrate solution together with a reaction buffer (0.5 M Tris-HCl, 1.5 M NaCl, 50 mM $CaCl_2$, 2 mM sodium azide, pH 7.6). Fluorescence intensity for every sample was measured every 15 seconds for 3 minutes with excitation set at 485 nm and emission at 530 nm using the Infinite 200 PRO multimode reader (TECAN, Mannedorf, Switzerland). A linear incline was determined, and collagenase concentration was calculated using a calibration curve generated by collagenase samples of known concentrations.

Stress/strength profile of collagen fibers exposed to collagenase: Collagen type-I bundles, sourced from the tails of Wistar rats, were suspended using a LLOYD LF-Plus Digital Material Tester force machine. The bundles were suspended inside a bath loaded with a buffer that simulates the composition of the oral fluid: an isotonic solution, pH 6.7 at 37° C. complemented with electrolytes including sodium, potassium, calcium, magnesium, bicarbonate, and phosphates. The bundles, 0.8-1.2 mm in diameter, were cut into two equal 4-cm sections, acting as an internal control. Collagenase type-I from *Clostridium histolyticum* (Sigma-Aldrich) was added at different concentrations and the stress/strength profile of the collagen fibers was recorded as a function of the collagenase treatment. The Ultimate Tensile Strength (UTS) of the collagen bundle was determined for each collagenase concentration.

Fibroblast adherence to collagen fibers. The fibroblast morphological change was recorded using The LSM 710-laser scanning confocal microscope (Zeiss) over a period of 90 minutes. The fibroblasts nuclei were stained using Hoechst 33342 (Thermo Fisher Scientific, MA, USA). The Hoechast 16.23 mM stock solution was diluted 1:2000 in Dulbecco's Phosphate Buffer Saline (DPBS, Sigma-Aldrich, St. Louis, USA) and the collagen fiber buffer was removed. 3 ul of the diluted solution was added, followed by 10 minutes light protected incubation. The staining solution was removed, and the fiber was washed 3 times in PBS.

Collagen regeneration SEM. Collagen bundles were mounted on carbon tape and imaged using a Zeiss UltraPlus high-resolution scanning electron microscope (HR-SEM) equipped with an Everhart-Thornley secondary electron detector. Each bundle was then cut in half. The untreated half acted as an internal control for each treated bundle. All data points are the mean of 14-20 experimental points. Collagen fibers were exposed to 0.05 mg/ml collagenase for 8 hours. Ethylenediaminetetraacetic acid (EDTA; ST. Louis, USA), 3 mM along with two drops of $NH_4Cl$ 1M buffer, were added for 30 minutes in order to retard the enzyme's activity. Subsequently, the media was removed, and the treated bundles were washed two times with new growth media to allow bundle regeneration.

Collagen fibers regain their initial mechanical strength post nano-surgery. Collagen fibers were sourced from tails of Wistar rats. Each bundle was cut in half. The untreated half acted as an internal control for each treated bundle. All presented data points are the mean of 14-20 experimental points. Collagen fibers were exposed to collagenase at concentration of 0.05 mg/ml for 8 hours in order to weaken the bundles. After 8 hours a concentration of 0.02M ethylene diamine-tetra-acetic acid (EDTA; ST. Louis, USA) was added for 15 minutes in order to inhibit the enzyme activity hence allowing the bundle regeneration. Subsequently, the media was removed, and the treated bundles were washed twice with new growth media.

RNA extraction, PCR and RT-PCR. mRNA was extracted from the rats' gingival tissue using a TRIzol reagent (Thermo Fisher Scientific, MA, USA). The mRNA sequences were first reverse-transcribed to complementary DNA (cDNA) with reverse transcriptase using a thermocycler (LabCycler SensoQuest PCR, SensoQuest, Germany). To quantify the genes real time-PCR was employed (BioRad CFX96, Bio-Rad Laboratories Ltd., Israel). Each gene was independently amplified using specific probe and primers. Cycling times: 5 min at 95° C., (15 sec at 95° C., 45 sec at 63° C.) X40 cycles.

Tooth displacement model. All animal trials followed the Technion Institutional Ethical Committee's guidance. All rats were anesthetized in two stages. In the first stage the rats were anesthetized with isoflurane. In the second stage each rat was injected a mixture of Ketamine and Xylazine intraperitoneally. After each procedure, the rats were transferred and kept in an incubator, with constant oxygen flow, until they reached full recovery.

An ordinary orthodontic Ni—Ti closed coil spring (9 mm closed coil spring nickel and titanium alloy that has 2 eyelets with an inner radius of 0.76 mm) was used to connect the 1st molar in the upper pallet to the front upper incisors of the rat. The Ni—Ti coil spring was glued to the tooth (3M UNI-TEK), which generates constant force of 200 grams (1.96 N) when extended between 12-24 mm. The force applied in the oral cavity was the same on all the rats that participated in the experiment. This type of coil has been used and studied in orthodontics for years and has proven to be effective in orthodontic procedures. The procedure of installing the Ni—Ti coil closed spring was performed using human orthodontics equipment and materials. The 1st upper molar and the upper incisors were dried and cleaned using cotton swabs to remove any debris that accumulates. The teeth were conditioned using Transbond Plus etching primer conditioning agent by 3M UNITEK for 5-10 seconds creating a rugged surface to allow for stronger bonding. Following the conditioning, a small amount of composite Transbond LR light-cure adhesive (3M UNITEK) was spread over the molar. The eyelet ring of the Ni—Ti closed coil spring was placed in parallel with the tooth and light cured using LEDEX dental curing light for 10-15 seconds. Once again, a small amount of bonding agent was spread over the ring and light cured for at least 40 seconds. The binding of the incisors was performed in a similar manner. Cleaning, drying and conditioning of the incisors were initially done. Subsequently, a stainless ligature was placed through the second eyelet ring of the Ni—Ti closed coil spring and we were able to achieve strong binding by braiding it around the incisors.

Collagenase-liposomes (see above Liposome Preparation), or a similar concentration of free collagenase, were applied directly to the sulcus. To apply the formulations a 30 G needle was inserted carefully into the sulcus pocket, in a downward motion that was parallel to the tooth to a depth of ~1-2 mm, and a 50 ul volume was deposited to the buccal and lingual side of the tooth. The total duration of the studies was 60 days: 15 days of braces with the different treatments and an additional 45 days of recovery (after the braces removal). During the 15 days of treatment tooth displacement measurements were taken every 3 days using a digital caliper with an instrument error of 0.02 mm and microCT scans were performed on day 15 and day 60. The distance between the eyelet of the Ni—Ti closed coil on the first molar and the back of the upper incisors was measured and recorded using the digital caliper. Before each tooth displacement measurement, the rats were weighed and then anesthetized using isoflurane. This kind of anesthesia allowed fast measurements and short recovery time for the rats.

Example 1

Collagenase Nanoparticles

The progression of pancreatic ductal adenocarcinoma (PDAC) is accompanied by the development of a dense extracellular matrix (ECM) that acts as a physical barrier, preventing drugs from penetrating the tumor. Collagen, a primary structural protein that is involved in healthy and pathologic tissue remodeling, is a major component of the PDAC's ECM. In this study we evaluated a nanoscale drug delivery system that targets the collagen component of the ECM, by the localized delivery of a proteolytic enzyme—collagenase type-I (FIG. 1A-D). For this, we developed a nanoparticle that protected the enzyme from bio-deactivation and prolonged its release rate. Then, we demonstrate the barrier function of the PDAC ECM. Subsequently, we tested whether collagenase nanoparticles can successfully degrade collagen in PDAC tumor tissue. And finally, we measured the therapeutic efficacy of pretreating the tumor with nanoparticulate collagenase followed by a drug.

Figure 1E:
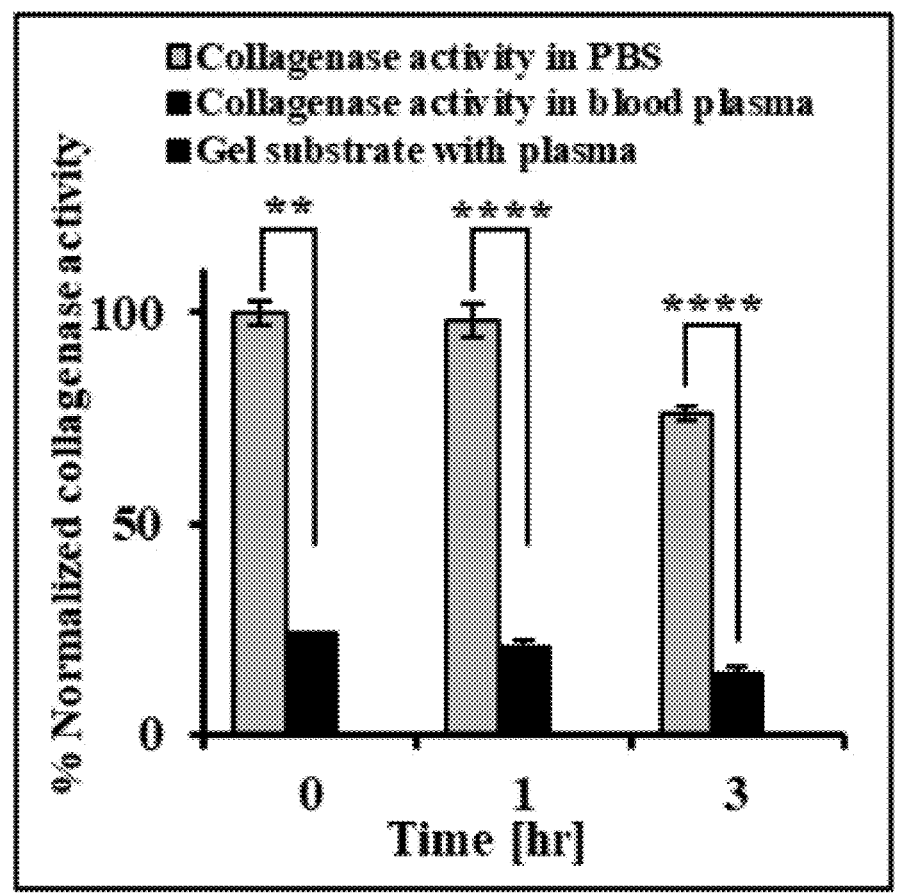
Figure 1F:
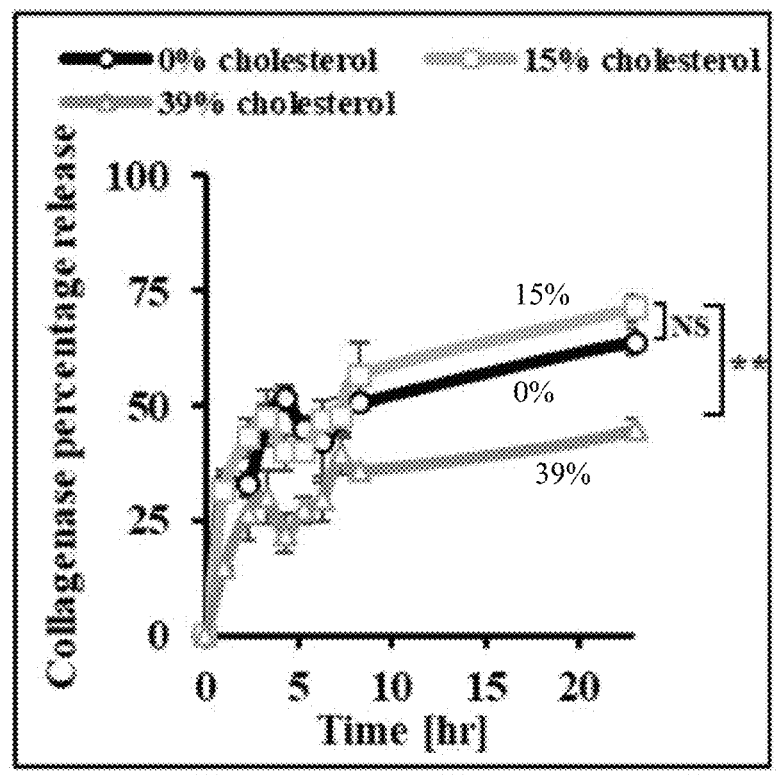
Figure 1G:
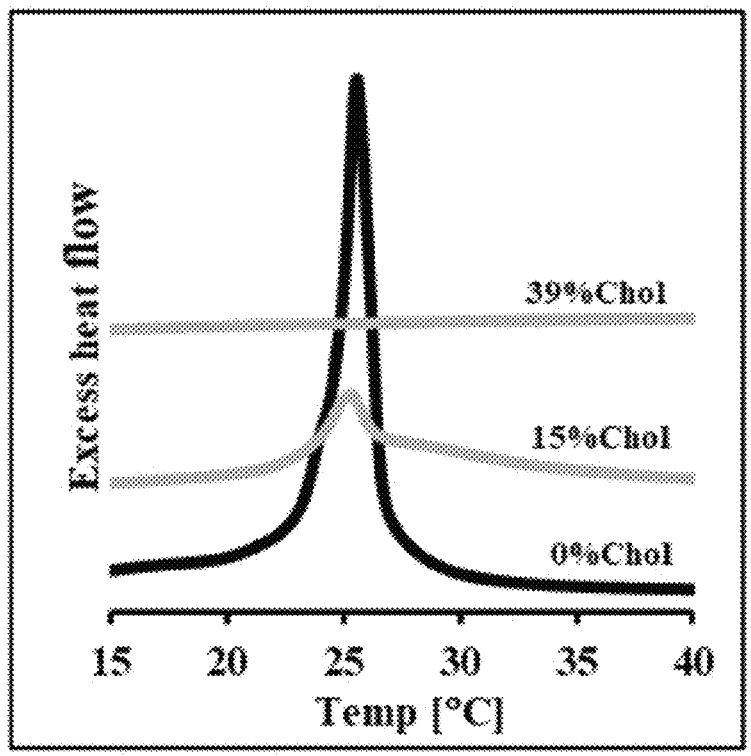
Figure 1H:
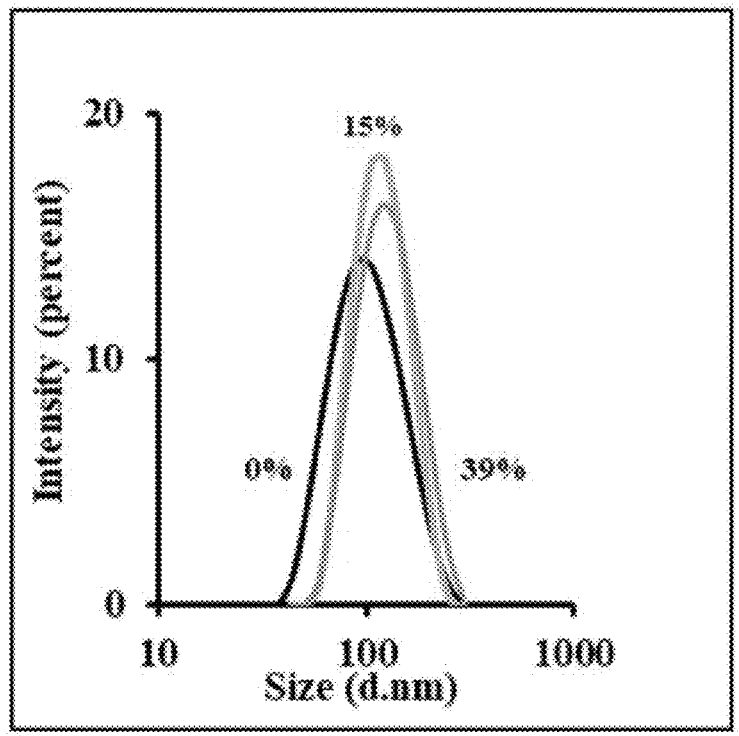

Encapsulating proteins in nanoparticles must overcome several challenges, including possible denaturing of the protein during the loading process and maintaining a therapeutic release rate at the target site. Because the half-life of collagenase in circulation is extremely short, we loaded collagenase into liposomes, which protected it from early deactivation in the plasma and prolonged the enzyme's activity (FIG. 1E). The primary phospholipid used to construct the liposomes was 1,2-dimyristoyl-sn-glycero-3-phosphocholine (DMPC), comprised of two 14:0 hydrocarbon chains conjugated to the phosphocholine head group. DMPC's phase transition temperature (Tm) is 23° C., which is favorable for loading collagenase without compromising the enzyme's activity during the formulation. To modulate the collagenase release kinetics from the liposomes, we varied the cholesterol content in the phospholipid bilayer. Specifically, we tested the effect of three different cholesterol concentrations (0, 15 and 39 mole %) on the release kinetics. Our results show that the higher the cholesterol content, the slower collagenase releases from the liposomes (FIG. 1F). At 39 mole % cholesterol, a prolonged enzyme release profile was achieved—less than 40% of the encapsulated collagenase was released over 24 hours. No significant difference in the enzyme release profile was observed between the formulations consisting of either 0 or 15 mole % cholesterol, releasing approximately 60% of the enzyme over 24 hours. This is explained by the effect cholesterol has on the physicochemical stability of the lipid bilayer. Differential scanning calorimetry (DSC) analysis of the lipid bilayers showed that DMPC has a sharp phase transition at 25.5° C. (FIG. 1G). Increasing the cholesterol content in the liposome membrane decreases the intensity of the thermogram. At 39 mole % of cholesterol no phase transition is recorded as the membrane enters a low-permeability liquid-ordered phase, which explains the prolonged release. Based on these results, we decided to proceed with our study using 100-nm DMPC liposomes enriched with 39 mole % cholesterol and PEG-DSPE for extending the liposome's circulation time (FIG. 1H).

Example 2

Fibrotic Extracellular Matrix Functions as a Mass Transport Barrier in PDAC

Figure 2A:
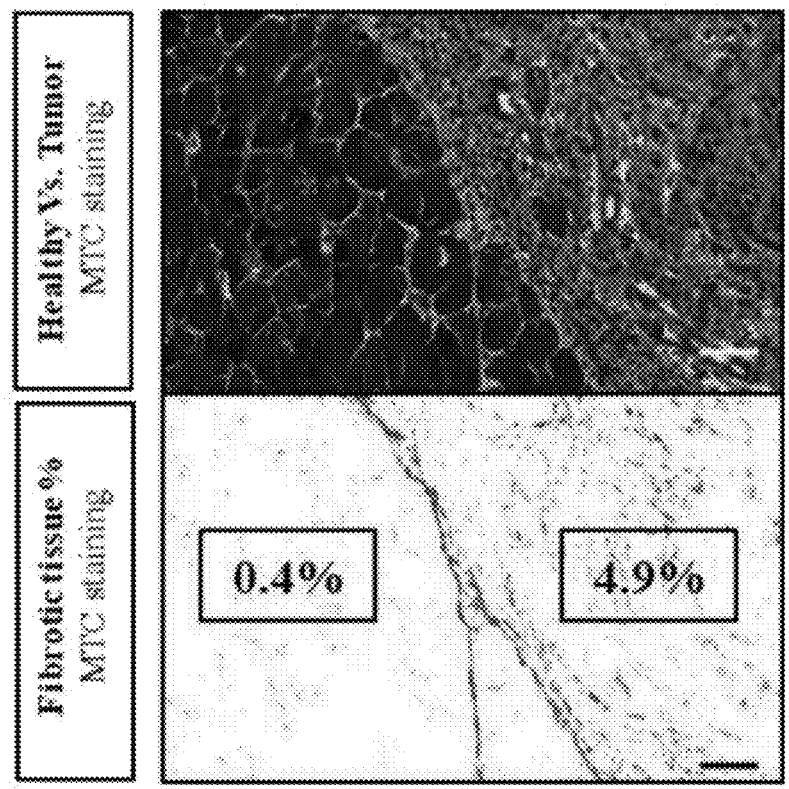
FIGS. 2A-K: PDAC fibrotic collagen matrix acts as a mass transport barrier. (2A) Micrographs showing the tumor's ECM tissue has an increased collagen component. Collagen was stained with Masson's trichrome in healthy and diseased pancreatic tissue. Scale bar=50 μm. (2B) Line graph showing poor nanoparticle pancreatic uptake over 24 hours in PDAC-bearing mice. (2C-D) The quantity of Gd-liposomes that reached the pancreas of PDAC mice at different time intervals after an intravenous administration was quantified using elemental analysis (n=3). The majority of Gd-liposomes reach the healthy region in the diseased pancreas. Fluorescent liposomes were imaged in the pancreas using intra-vital microscopy (2C-bright field, 2D-fluorescent; scale bar=1 mm, fluorescent liposomes are labeled red). (2E-G) (2E) Histological H&E-staining analysis of the pancreas enabled differentiating between the healthy (sections I and II) and diseased segments of the pancreas (sections III-V). (2F) Fluorescent histology of the corresponding sections indicated that (2G) as quantified by relative fluorescence the vast majority of the nanoparticles are concentrated in the healthy regions of the diseased pancreas. (Scale bar=2 mm; fluorescent sections: liposomes-red, nuclei-blue, n=3). (2H-J) Gd liposomes were injected to the tail vein and the mice were flash-scanned using 9.4 Tesla Mill. The Gd signal was imaged and measured in the bladder (2H) and pancreas (2I). The majority of the nanoparticles are secreted within 25 minutes after intravenous injection (2J). (2K) Line graph of Gd release from liposomes over a 24-hour period. *indicates p-value<0.05, **indicates p-value<0.01, according to a student's t-test with a two-tailed distribution with unequal variance.
Figure 2B:
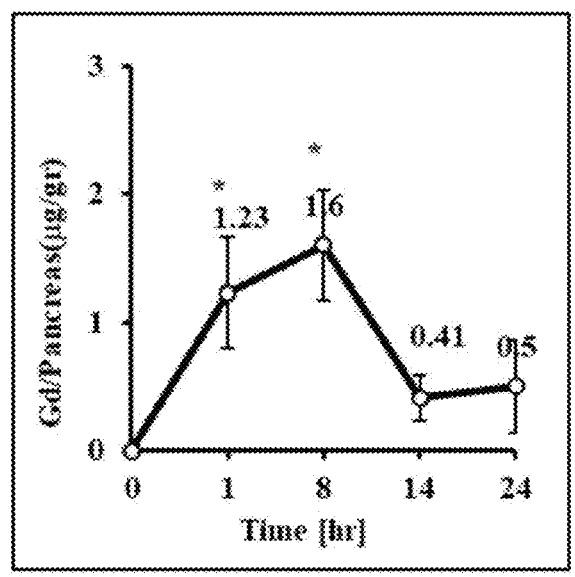
Figure 2C:
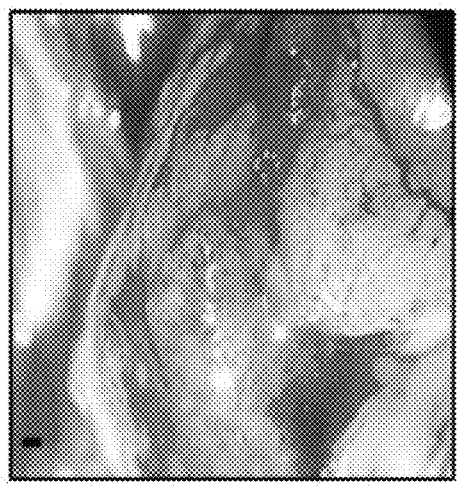
Figure 2D:
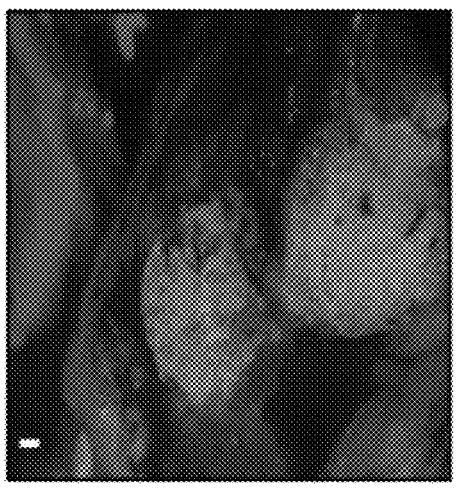
Figure 2E:
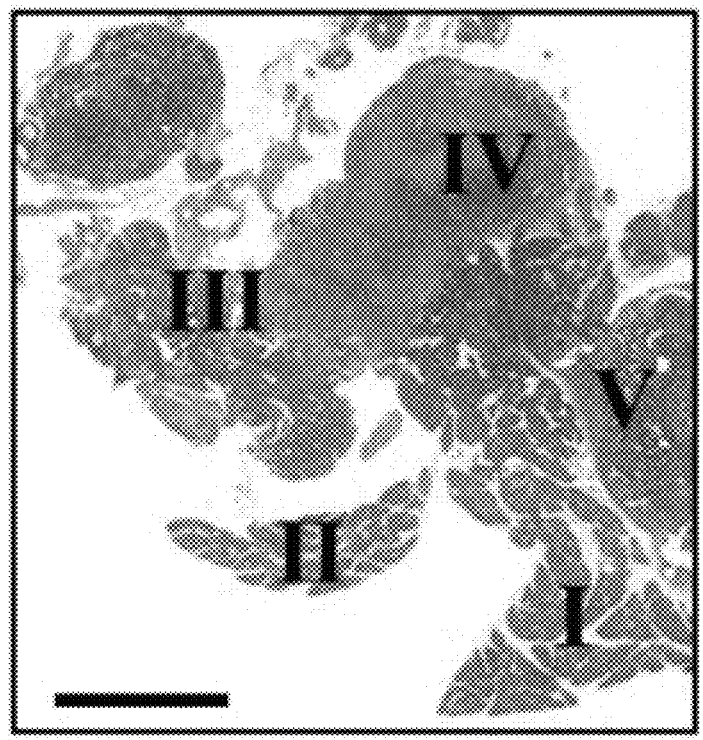
Figure 2F:
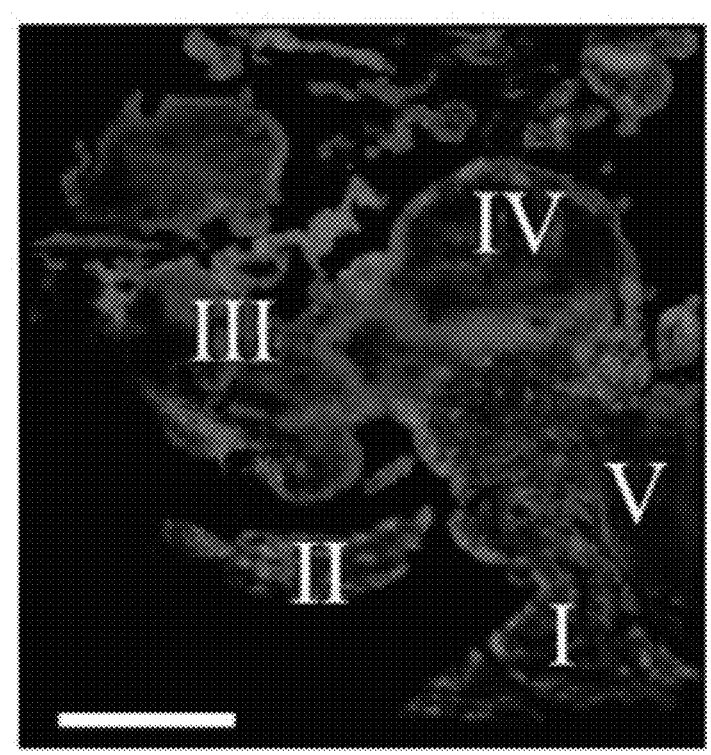
Figure 2G:
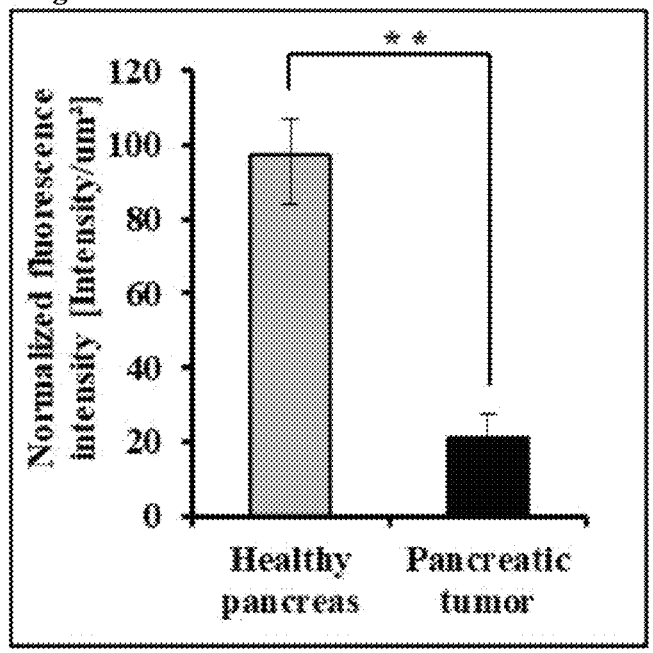
Figure 2H:
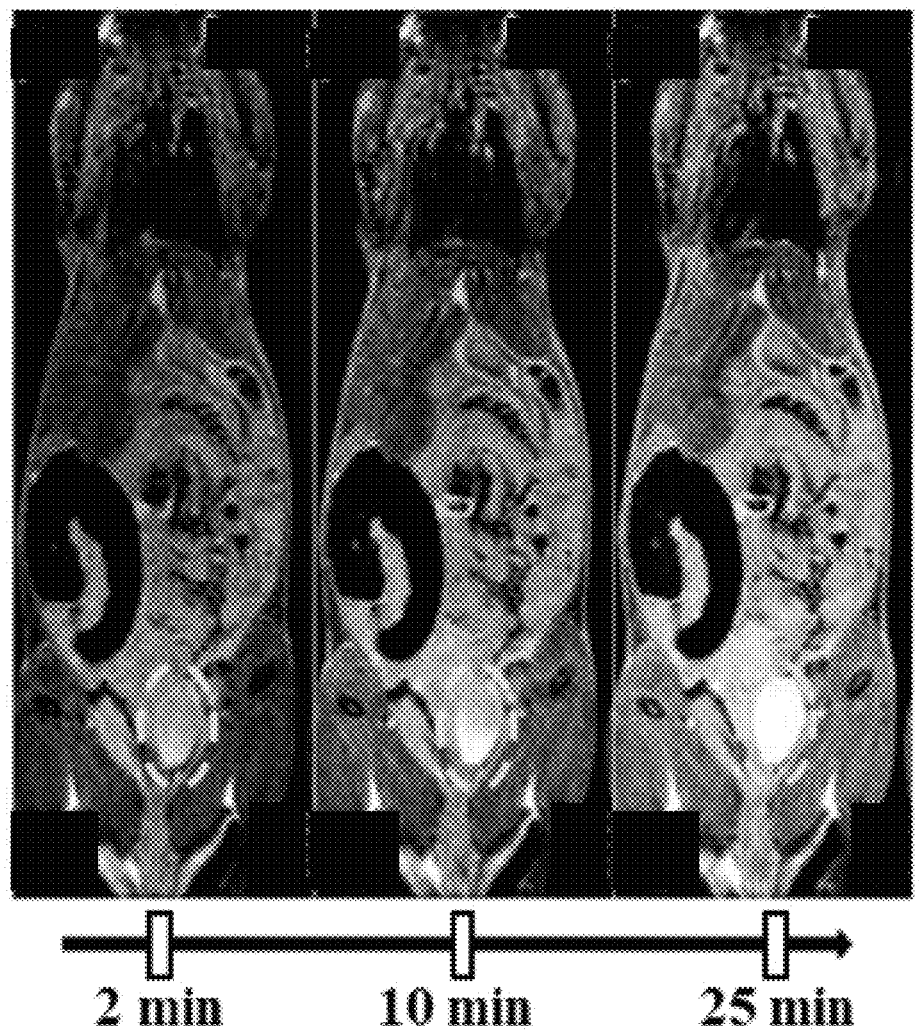
Figure 2I:
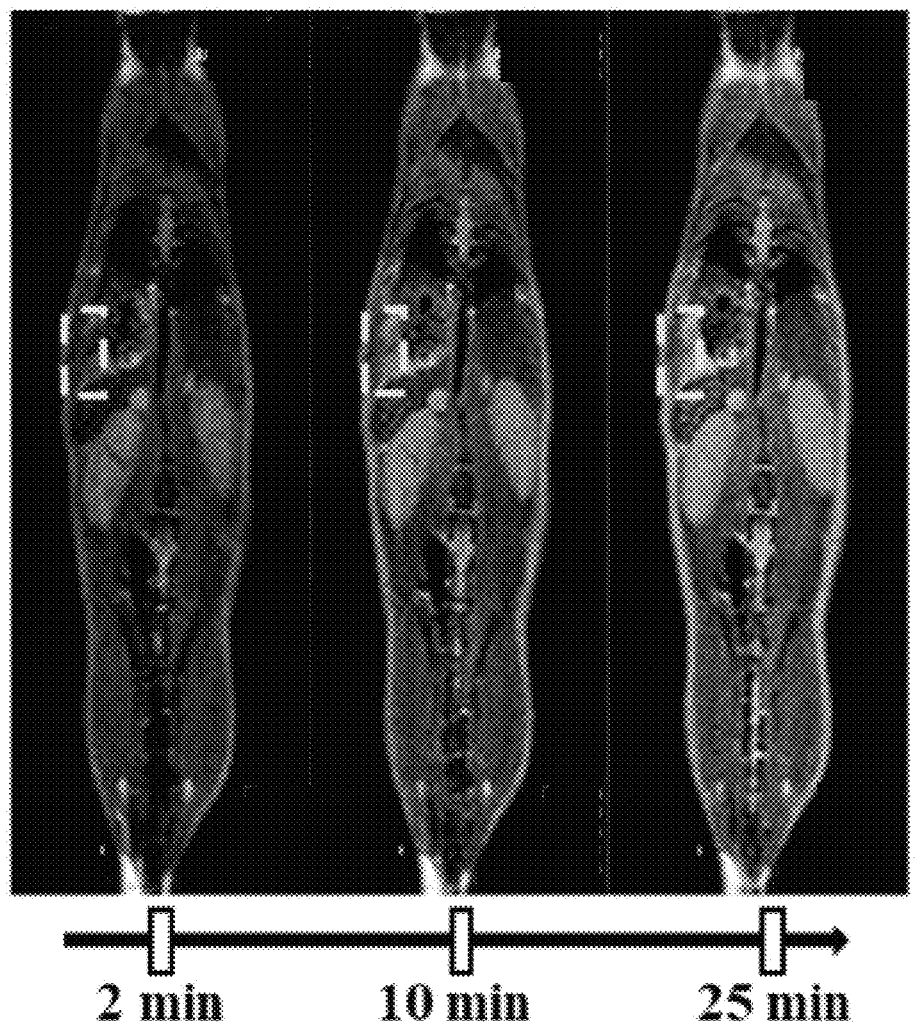
Figure 2J:
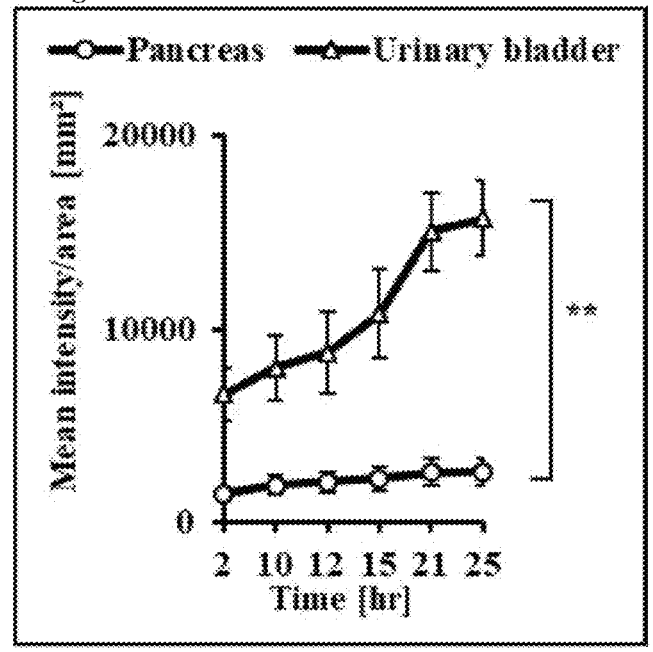
Figure 2K:
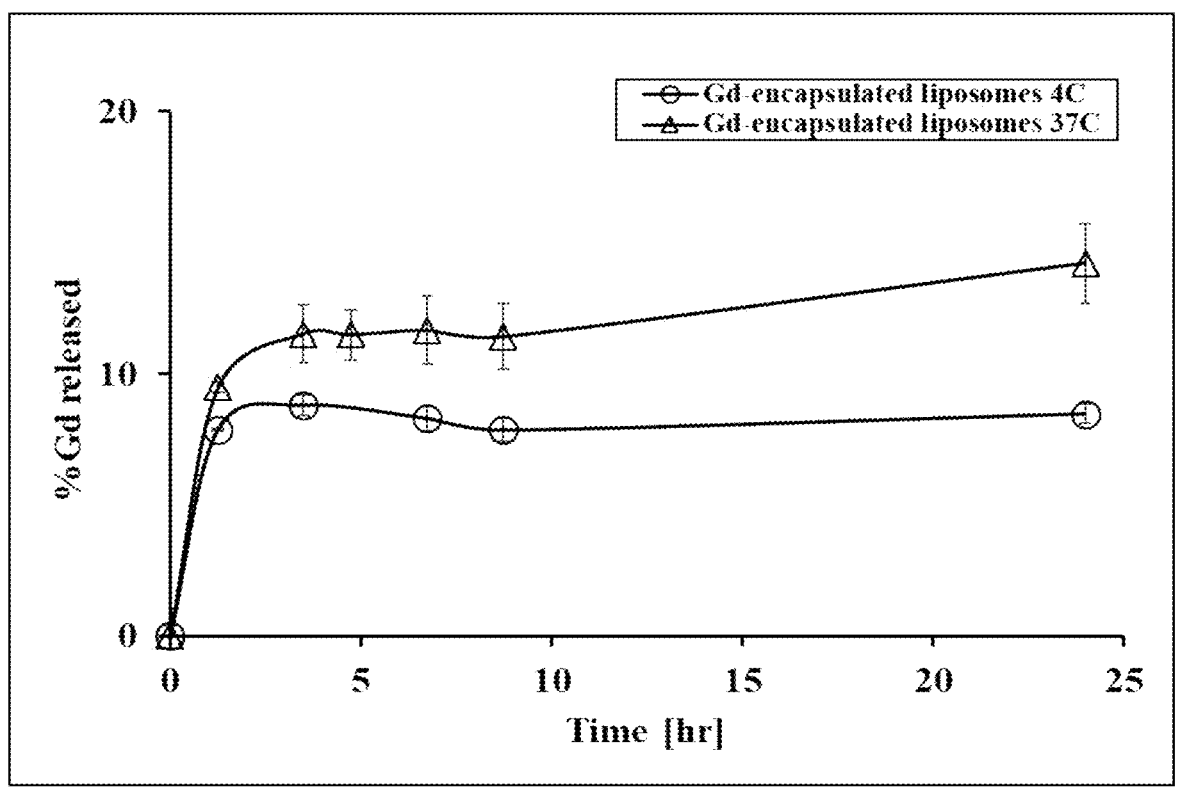

We characterized the collagen content in healthy and diseased regions of the pancreas. Masson's trichrome staining demonstrated that the collagen content in pancreatic tumors was 12.25-fold greater than the collagen content in the healthy pancreas (FIG. 2A). To assess the biodistribution of nanoparticles in healthy and diseased pancreases, mice bearing PDAC were injected with 100-nm liposomes loaded with an MRI contrast agent gadolinium (Gd) and co-labeled with a fluorescent dye (rhodamine) in the lipid bilayer. Release of Gd from the liposomes was gradual with less than 20% released in 24 hours (FIG. 2K). Eight hours post intravenous administration maximal pancreatic accumulation was recorded by elemental analysis, reaching 2.65 µg-Gd/g-pancreas whereas after 14 hours the concertation decreased to 0.83 µg-Gd/g-pancreas (n=3; FIG. 2B). In total, the level of nanoparticles that accumulated in the pancreas corresponds to 1% of the injected dose. Using non-invasive intra-vital microscopy (FIG. 2C-D) and qualitative and quantitative histological analyses (FIG. 2E-F) we imaged the liposomal biodistribution within the diseased pancreas after intravenous injection. Interestingly, we noticed that the collagen fibrotic barrier inhibited the penetration of the liposomes into the diseased regions of the pancreas. Specifically, 97.2±1% of the liposomes that reached the pancreas accumulated in the non-neoplastic regions of the pancreas (FIG. 2F, sections I-II), while the remainder accumulated in the cancerous tissue (FIG. 2F, sections III-V; FIG. 2G). In total, out of approximately $1.3 \times 10^{15}$ liposomes that were injected intravenously, only $1.3 \times 10^{13}$ liposomes reached the pancreas, of which only $3.9 \times 10^{11}$ liposomes reached the PDAC cancerous tissue corresponding to 29.8 ng-Gd/g-pancreatic-tumor. MRI imaging (9.4T) of the liposomal biodistribution confirmed that majority of the Gd was cleared by the urinary system during the first half-hour post injection (FIG. 2H). However, a gradual increase in the pancreatic liposomal content was measured alongside the bladder clearance (FIG. 2I-J). Taken together, these data emphasize the barrier the ECM poses to uptake into the diseased pancreas.

Example 3

Enzymatic Degradation of Collagen in PDAC

Figure 3A:
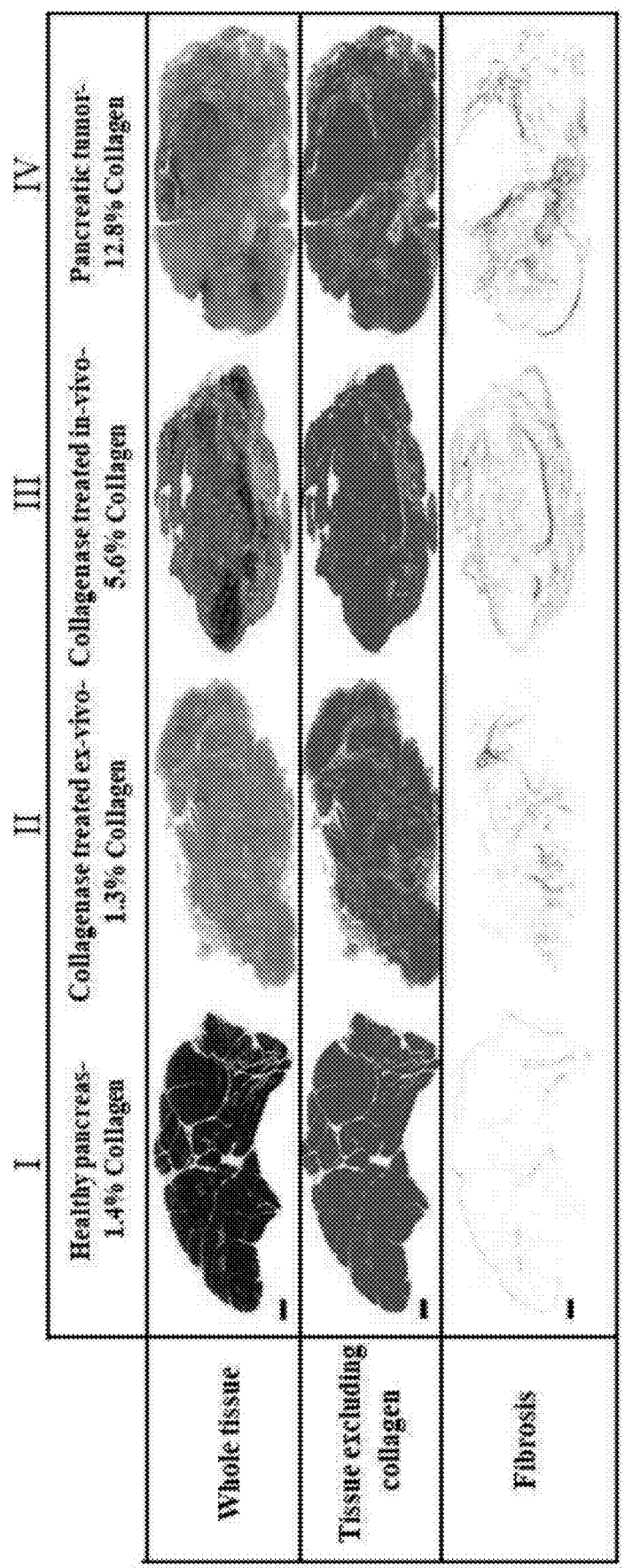
FIGS. 3A-H. Collagenase reduces the level of fibrosis in the PDAC ECM. (3A) Photographs of healthy pancreases (section I), collagenase treated PDAC ex-vivo (section II), collagenase-treated PDAC in-vivo (section III) and non-treated PDAC (section IV). (3B) Bar graph of collagen density. n=8 in each treatment group. (3C-E) Micrographs of collagen fibers in healthy, PDAC and collagenase-treated PDAC tumors in-vivo. PDAC-bearing mice and healthy mice were treated with collagenase-liposomes; the pancreas was then decellularized and imaged using HR-SEM. (3C) PDAC mice after being treated with collagenase-nanoparticles (C) and (3D) healthy pancreas were compared to (3E) non-treated PDAC pancreas. (3F-G) Bar charts showing the collagen mesh (3F) uniformity and (3G) size in healthy and PDAC mice, before and after the collagenase treatment. The in-vivo treatment decreased the mesh size to levels found in healthy pancreas. (3H) Bar graph of the percentage of tissue that is fibrotic after 8 and 24 hours of treatment with various concentrations of free collagenase. Scale bar=500 μm (n=6 biological replicates for the healthy pancreases, n=7 for the ex-vivo collagenase treated PDACs, n=9 for the in-vivo collagenase treated PDACs and n=8 for the non-treated PDACs). *indicates p-value<0.05 according to a student's t-test with two-tailed distribution with unequal variance. ***indicates p-value<0.001 according to student's t-test with a two-tailed distribution with unequal variance.
Figure 3B:
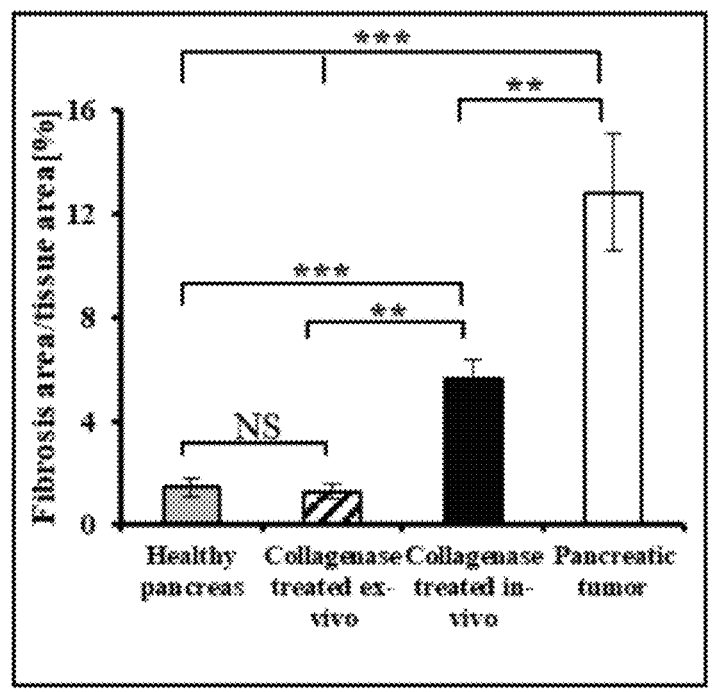

We next sought to characterize the collagen content in healthy and diseased pancreases before and after being treated with collagenase. Masson's trichrome staining was used to quantify the collagen content in the different groups. For this, pancreatic tumors were excised and incubated in collagenase solutions of different concentrations. Then, we evaluated the collagen content in healthy pancreases, pancreases with PDAC after the collagenase treatment and untreated pancreatic PDAC (FIG. 3A). The effect of three collagenase concentrations (0.05, 0.1 and 0.2 mg/ml) on PDAC collagen, was compared after 8 and 24 hours (FIG. 3A, section II; and 3H). The highest levels of collagen were recorded in the PDAC group=12.8±2.3% (FIG. 3A, section IV; 3B, n=10 biological replicates) while the lowest levels were observed in the healthy pancreas 1.4±0.4% (FIG. 3B, n=7 biological replicates). The level of fibrotic tissue in the PDAC group decreased to 1.28±0.3% (FIG. 3A, section II; 3B) after being treated with 0.05-0.2 mg/ml collagenase ex-vivo (n=8 biological replicates).

Figure 3C:
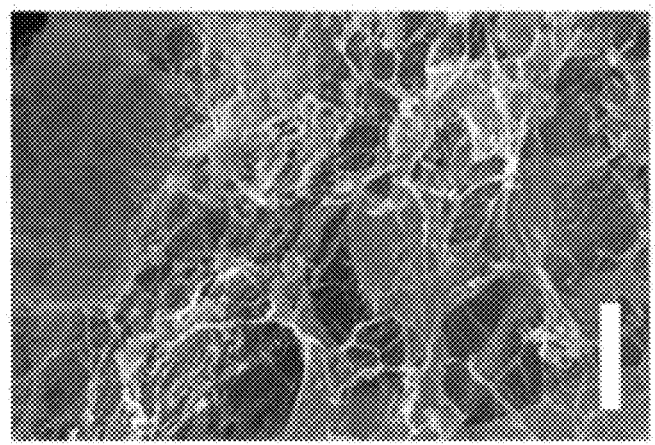
Figure 3D:
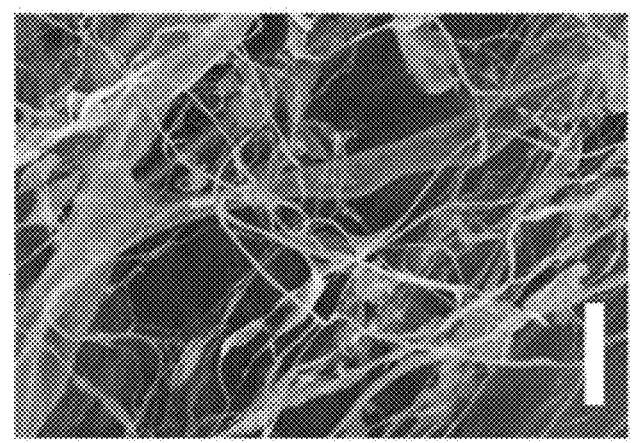
Figure 3E:
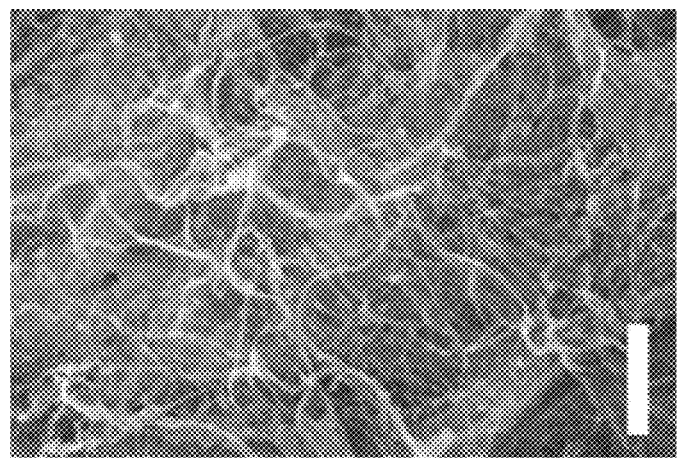
Figure 3F:
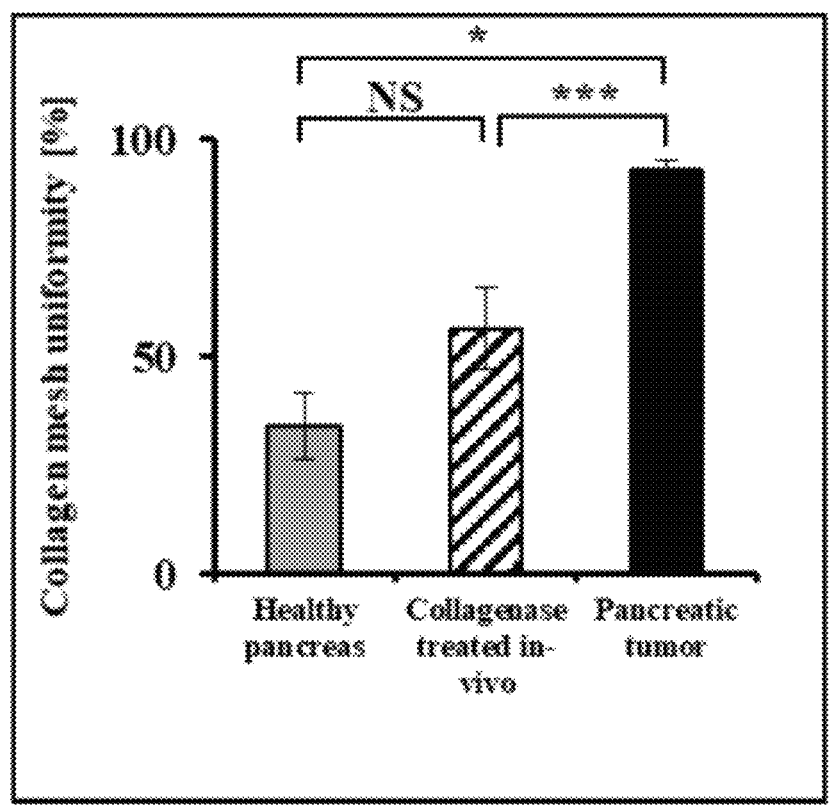
Figure 3G:
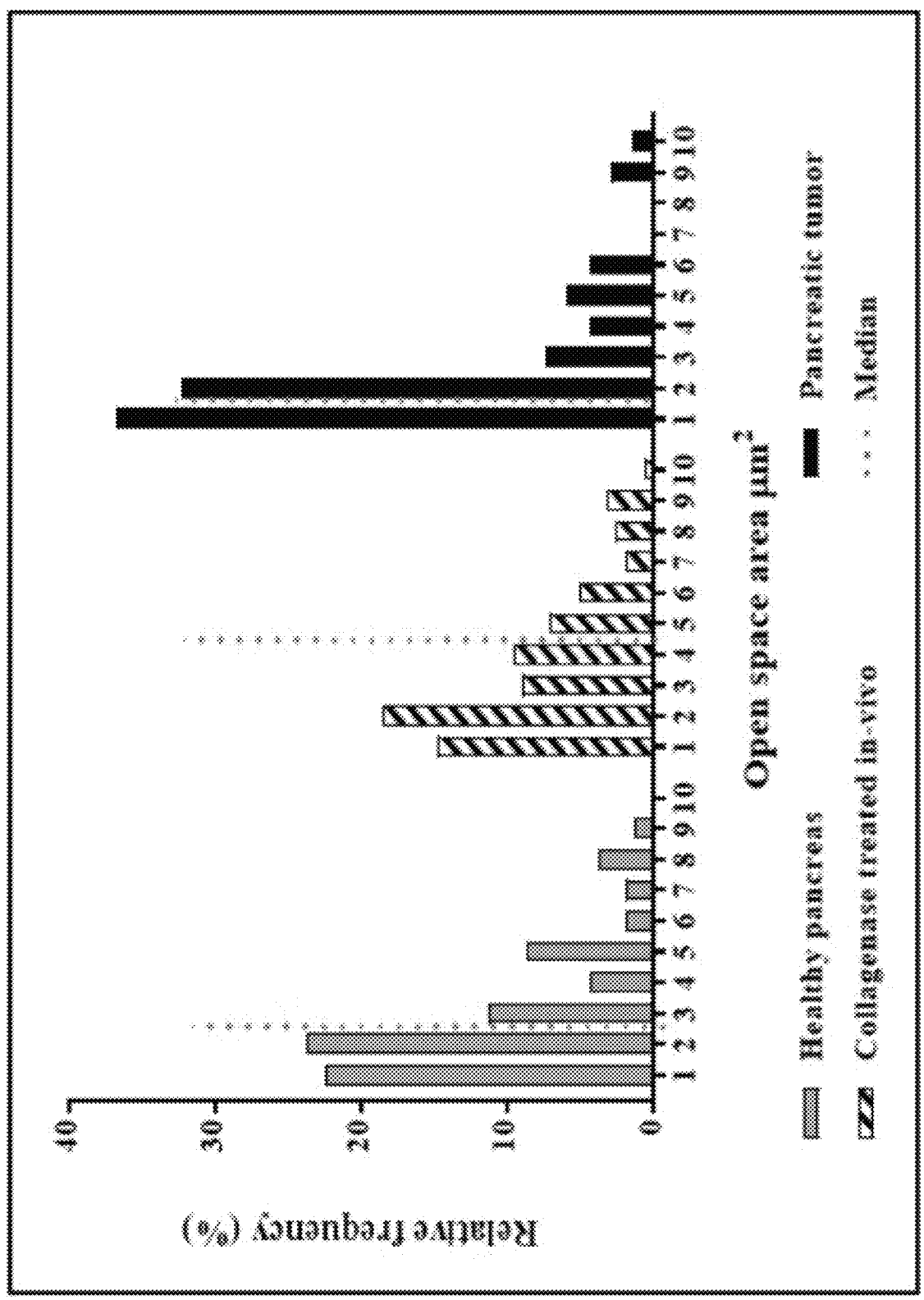
Figure 3H:
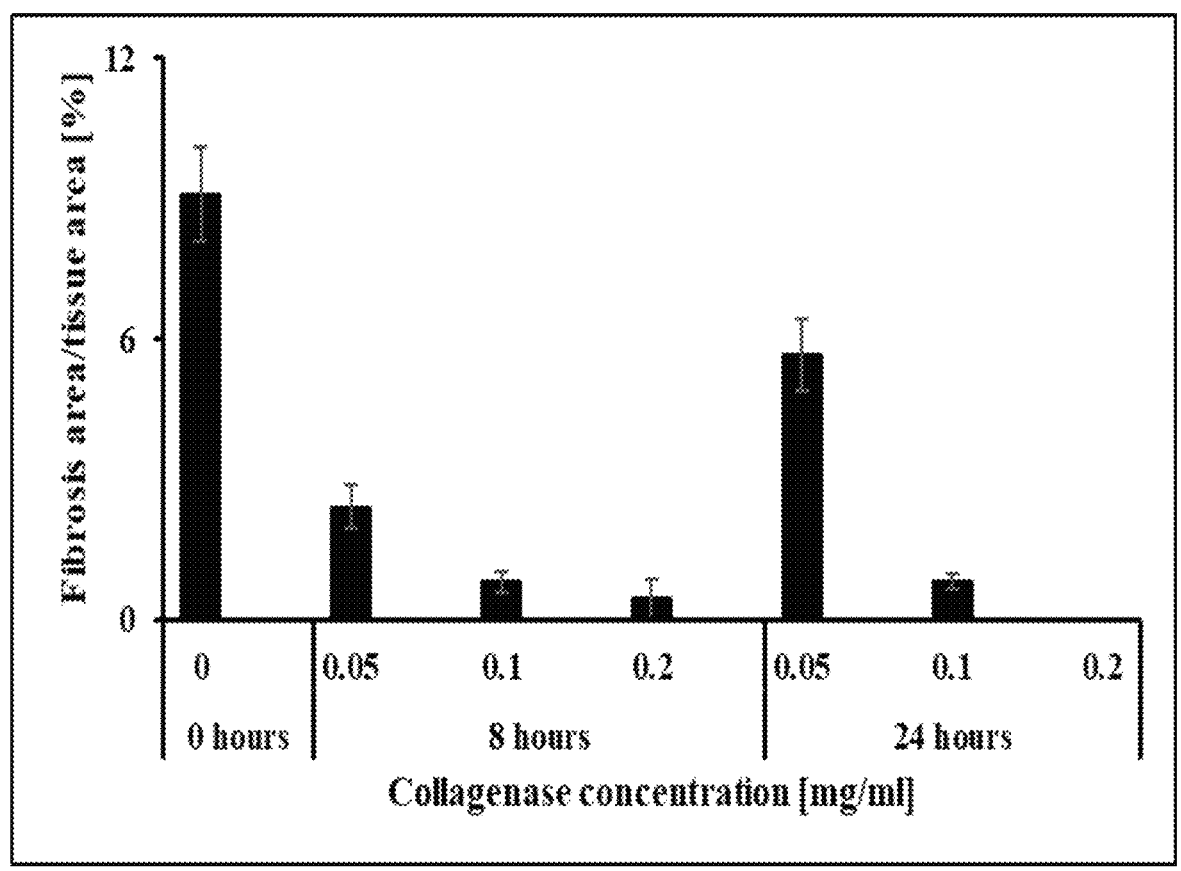

In-vivo, mice (n=9) bearing PDAC tumors were injected with collagenase-encapsulated liposomes and the collagen content of the tumor was evaluated histologically. Mason's trichrome staining 24-hours after the treatment indicated a decreased collagen content of 5.6±0.8% (FIG. 3A, section III; 3B). Additionally, the effect collagenase has on the microstructure of the collagen mesh in-vivo was studied. Healthy pancreases, PDAC after collagenase in-vivo treatment and untreated PDAC were decellularized and their ECM was visualized using scanning electron microscopy (SEM, FIG. 3C-E). Image analysis revealed that the collagen component in the tumor fiber mesh decreased after the collagenase treatment (FIG. 3F). The median of the area bordered within adjacent collagen fibers was 1.65 µm² in the PDAC tumors (n=4), compared to 2.75 µm² in the healthy pancreas (n=6), and 4.32 µm² in the treated PDAC tumors (FIG. 3G; n=4). Greater openings within the mesh suggested that such a treatment can enable improved uptake of drugs by pancreatic tumors. Therefore, we investigated whether the reduction of collagen density in PDA would translate into an improved treatment outcome.

Example 4

Therapeutic Efficacy, Circulating Cancer Cells and Metastasis

Figure 4A:
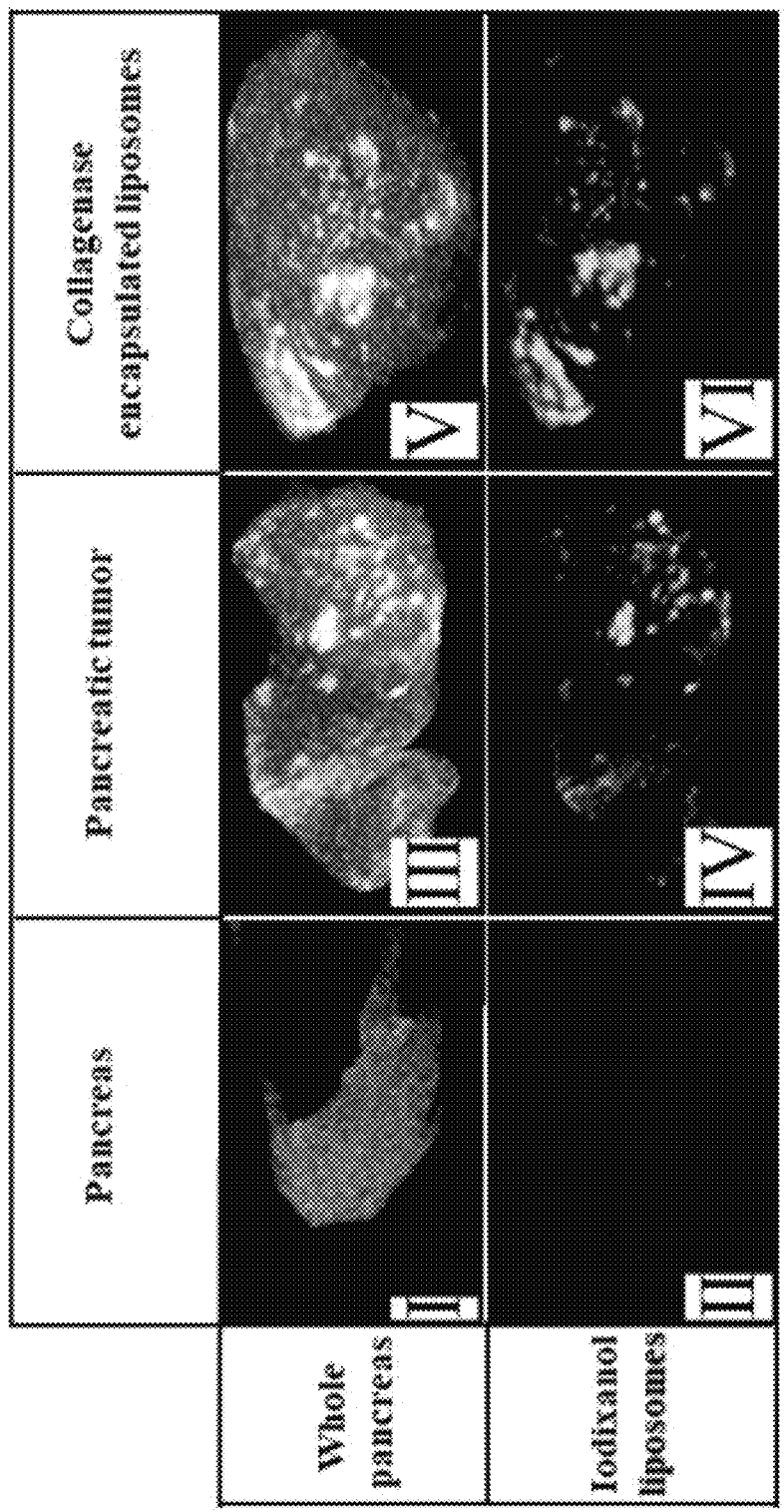
FIG. 4A-F: Enhanced pancreatic uptake after nanoparticulate collagenase pretreatment. (4A-B) Photographs showing collagenase-encapsulated liposomes pretreatment increased the pancreatic uptake of 100-nm liposomes. (4A) Iodine-loaded or (4B) Gd-loaded 100-nm liposomes were injected intravenously to mice bearing PDAC tumors, and the pancreases were imaged by CT; PDAC collagenase nanoparticle treatment group (sections V-VI) was compared to the non-treated PDAC group (sections III-IV) and to a control group (sections I-II). Similar quantitative results were recoded using Gd-liposomes and elemental analysis of the pancreas. (n=10 for the empty liposome group, n=5 of the free enzyme group, n=3 for the no pretreatment group and n=4 for the collagenase encapsulated liposomes treatment group). *indicates p-value<0.05, **indicates p-value<0.01 according to a Student's t-test with a two-tailed distribution with unequal variance. (4C) A schematic representation of the treatment protocol. Mice were administered 100-nm liposomes loaded with collagenase, followed by a single dose of 30-nm paclitaxel-loaded micelles (10 mg/kg-body-weight) the next day and the mCherry-expressing tumors were imaged. (4D) Bar graph showing no major body-weight fluctuations were measured among the groups. (4E-F) Therapeutic efficacy was recorded in mice pretreated with collagenase type-I encapsulated liposomes followed by paclitaxel. (4E) Photographs of mice bearing PDAC tumors pretreated (right) or non-treated (left) with collagenase liposomes. (4F) Bar graph showing the radiance in tumors imaged over two weeks; tumor radiance decreased by 64% in the liposome (test) group and increased by 16% in the control. Results are representative of five biological replicates for both groups. *indicates p-value<0.05 according to a Student's t-test with a two-tailed distribution with unequal variance.
Figure 4B:
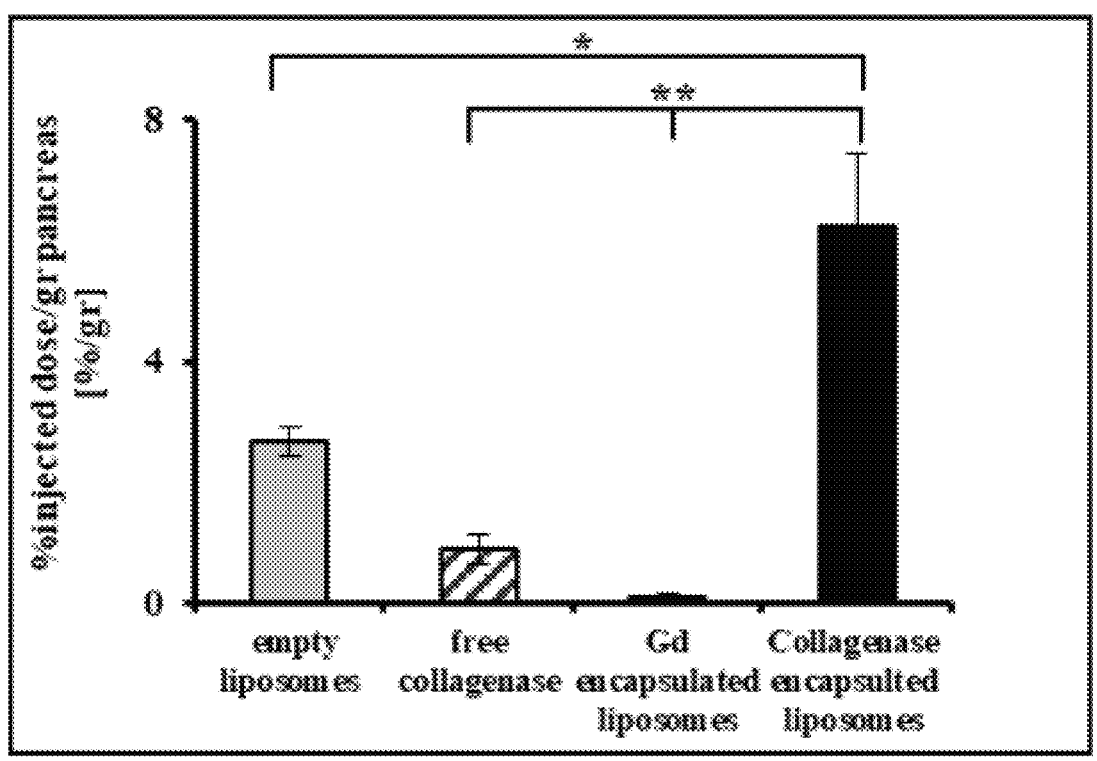

To test the capacity of collagenase nanoparticles to enhance drug delivery to pancreatic tumors, a 2-step approach was employed. Initially two doses of collagenase-loaded liposomes were given to amplify the degradation effect. Twenty-four hours later, a dose of therapeutic paclitaxel nanoparticles was given. To evaluate the penetration of the second stage therapeutic nanoparticles we loaded them with clinical contrast agents—Gd and Iodixanol. CT scans of PDAC-bearing mice after the 2-stage treatment revealed a 17% increase in uptake after the collagenase pretreatment, compared to the control (FIG. 4A). Even greater enhanced pancreatic uptake was measured by elemental analysis of Gd (FIG. 4B), specifically, 30.9 µg-Gd/g-pancreas (n=4) in the collagenase-nanoparticle treated PDAC mice, versus 15.1 µg-Gd/g-pancreas in mice (n=5) treated with the free enzyme (FIG. 4B).

Figure 4C:
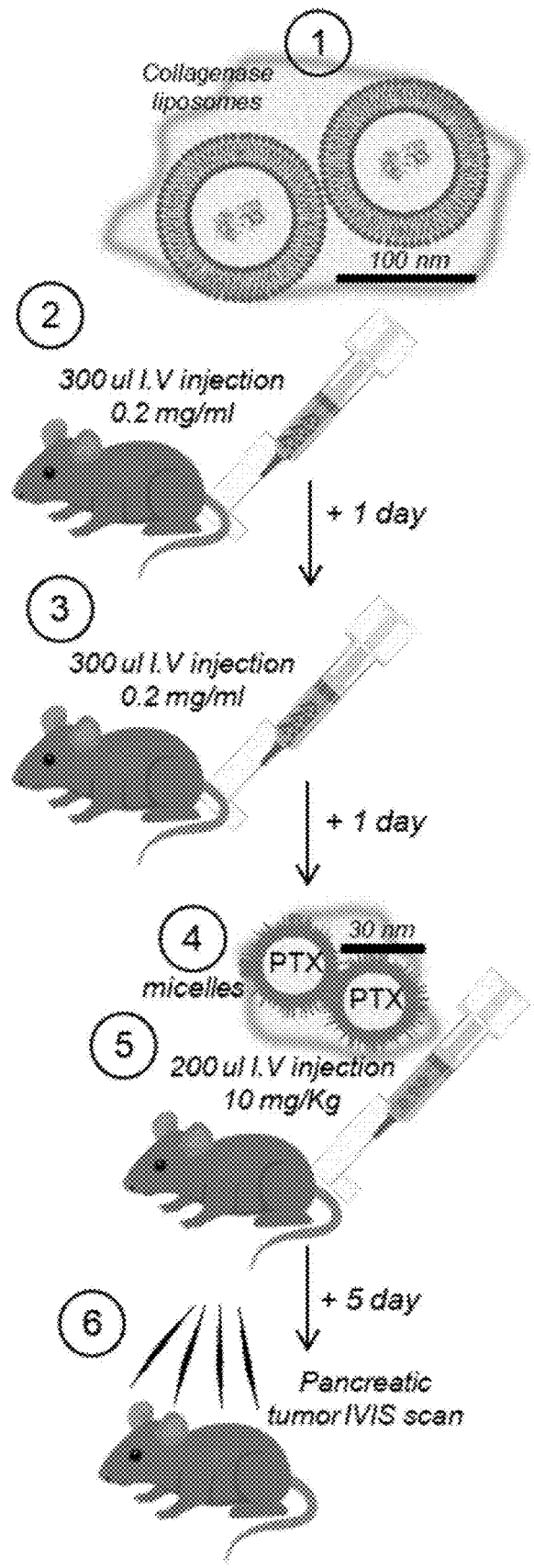
Figure 4D:
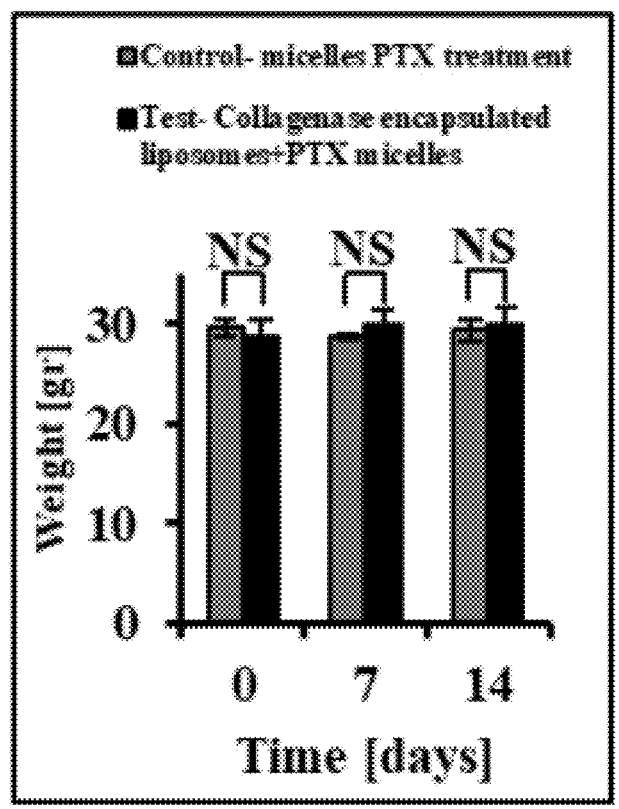
Figure 4E:
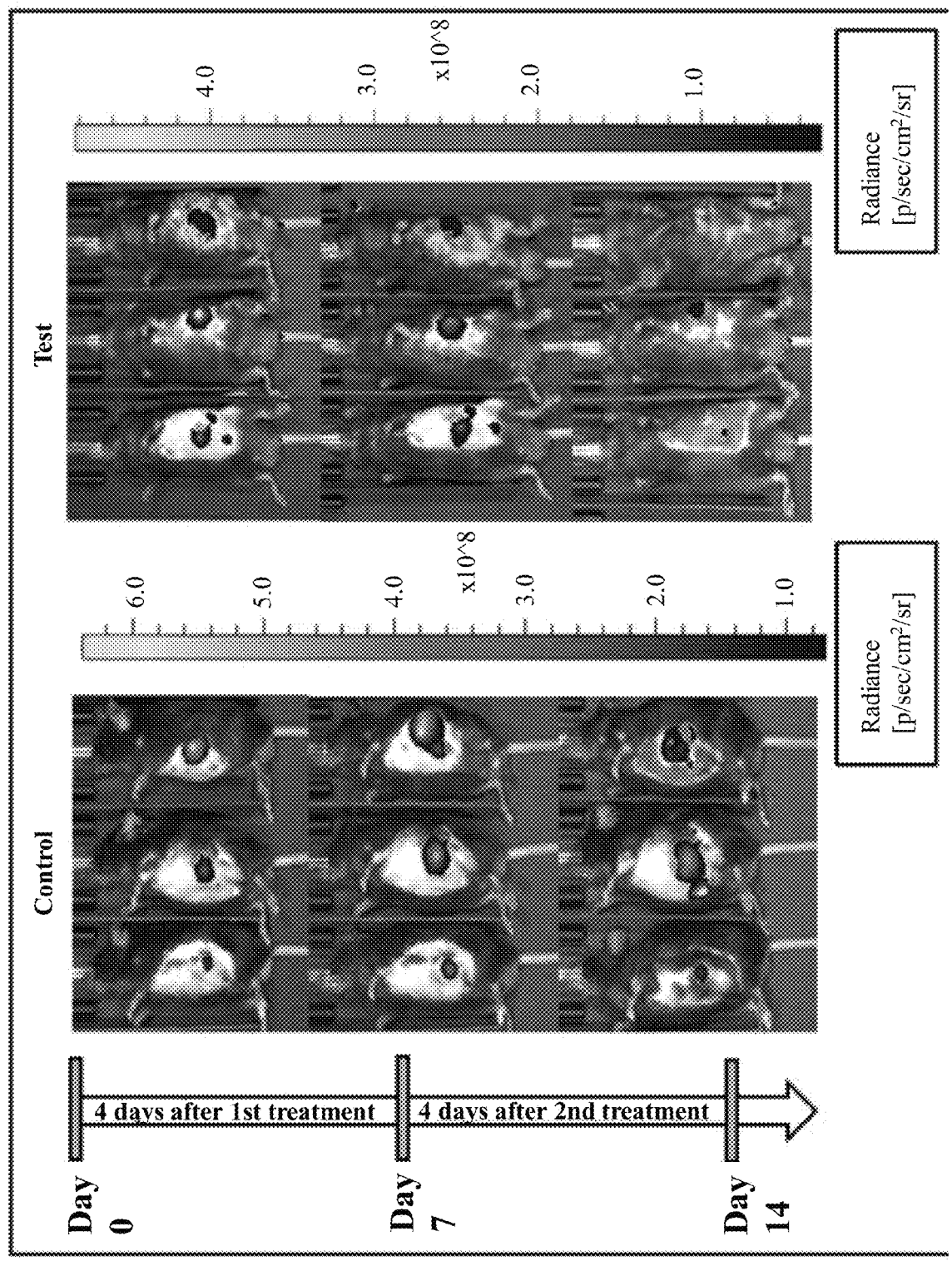
Figure 4F:
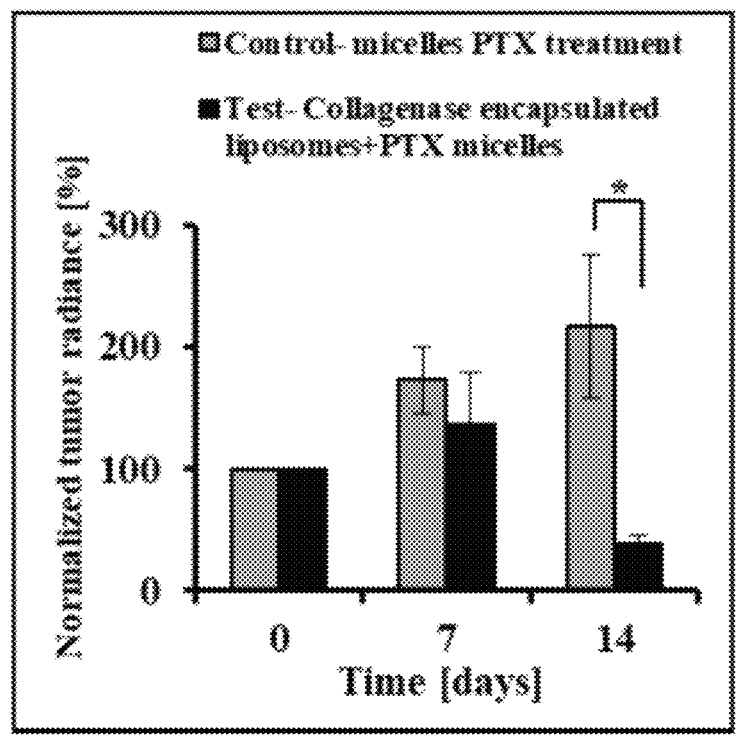

To evaluate the therapeutic efficacy of the collagenase pre-conditioning of PDAC tumors, mice bearing orthotopic mCherry expressing-KPC (Kras/+; p53R/+; P10dx/+) tumors were administered with nanomedicine micelles loaded with paclitaxel (10 mg/kg-body-weight) with or without the collagenase-nanoparticle pre-treatment. Five days after the paclitaxel treatment, the mice were scanned using a whole-animal imaging system (IVIS) to evaluate the drug effect on the tumor (FIG. 4C-D). The average tumor radiance decreased by 62±8.3% in the collagenase-treated group (n=5), while the average normalized tumor radiance in the control group increased by 16% (n=5, FIG. 4E-F).

Figure 5A:
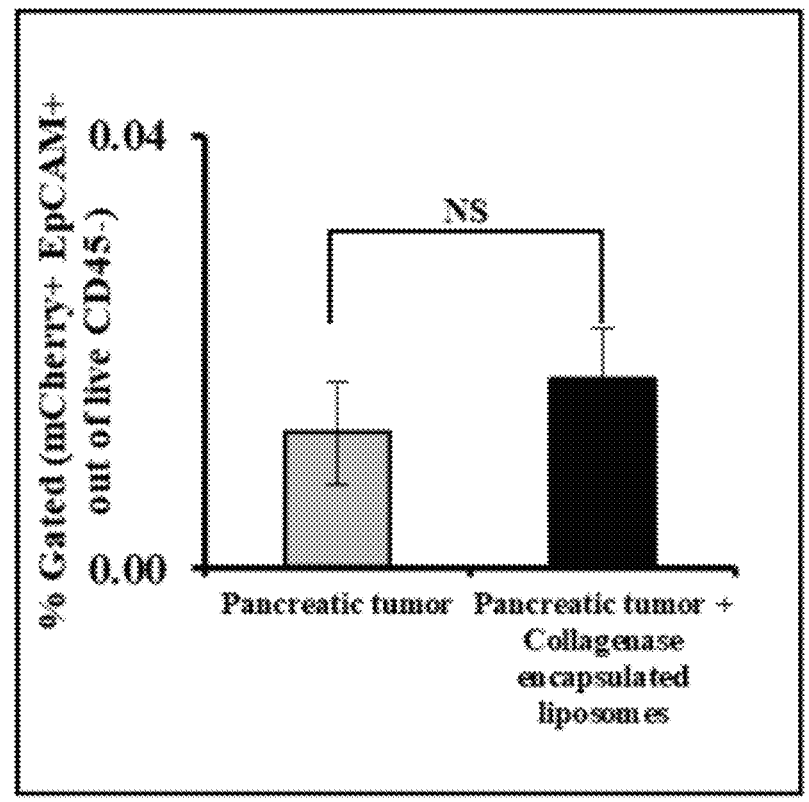
FIGS. 5A-F: Circulating tumor cells (CTCs) and tissue morphology after collagenase treatments. (5A) Bar graph showing circulating tumor cells (CTCs) measured in mice serum 24-hours after the collagenase treatment. No significant differences were observed between the PDAC-treated and the non-treated groups (n=4 for both groups). NS indicates p-value>0.05 according to a Student's t-test with a two-tailed distribution with equal variance. (5B) Bar graph showing the absence of metastatic disease in the liver, brain, spleen and lungs 7 days after the collagenase treatment. Results are representative of 2 biological replicates for all groups. NS indicates p-value>0.05 according to a Student's t-test with a two-tailed distribution with unequal variance. (5C) Histological evaluation of organs from in-vivo collagenase-treated and untreated mice. H&E staining (sections I-II) Masson's trichrome collagen staining (sections III-IV) of the liver, spleen, kidneys and lungs among the collagenase-liposome non-treated (odd numbers) and treated groups (even numbers). Results are representative of two biological replicates for both groups). Scale bar=50 μm. (5D-F) Bar charts comparing blood panels of collagenase-nanoparticle treated and untreated mice. (5D) oxygen chemistry, (5E) electrolyte analysis and (5F) red blood cell, reticulocyte, platelet count and white blood cell analysis between the collagenase encapsulated treated mice and non-treated mice 24 hours after the injection are shown. *indicates p-value<0.05 according to a Student's t-test with a two-tailed distribution with unequal variance.
Figure 5B:
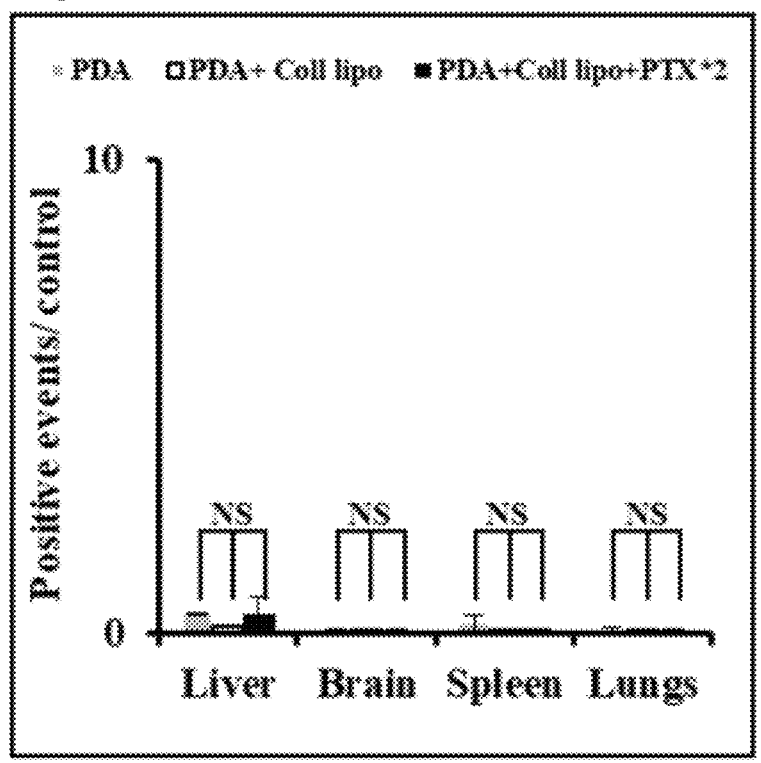

It has been theorized that delivering collagenase has the potential to act as a double-edged sword, by harming healthy organs or altering the tumor extracellular matrix in a manner that releases cancerous cells from the primary tumor into circulation. Therefore, we quantified the circulating tumor cells (CTCs) in mice treated with collagenase and the untreated control. No significant difference in the CTC blood count was observed among more than 300,000 cells that were analyzed in either group after 24-hours (FIG. 5A; n=4). Furthermore, metastatic cells were not detected in the liver, brain, spleen and lungs 7 days after either the collagenase treatment or the combined collagenase and paclitaxel treatment (FIG. 5B). These data suggest that the liposomal collagenase degrades the dense tumor ECM allowing nanomedicine penetration, but in a manner that is insufficient to release cancer cells into systemic circulation.

Figure 5C:
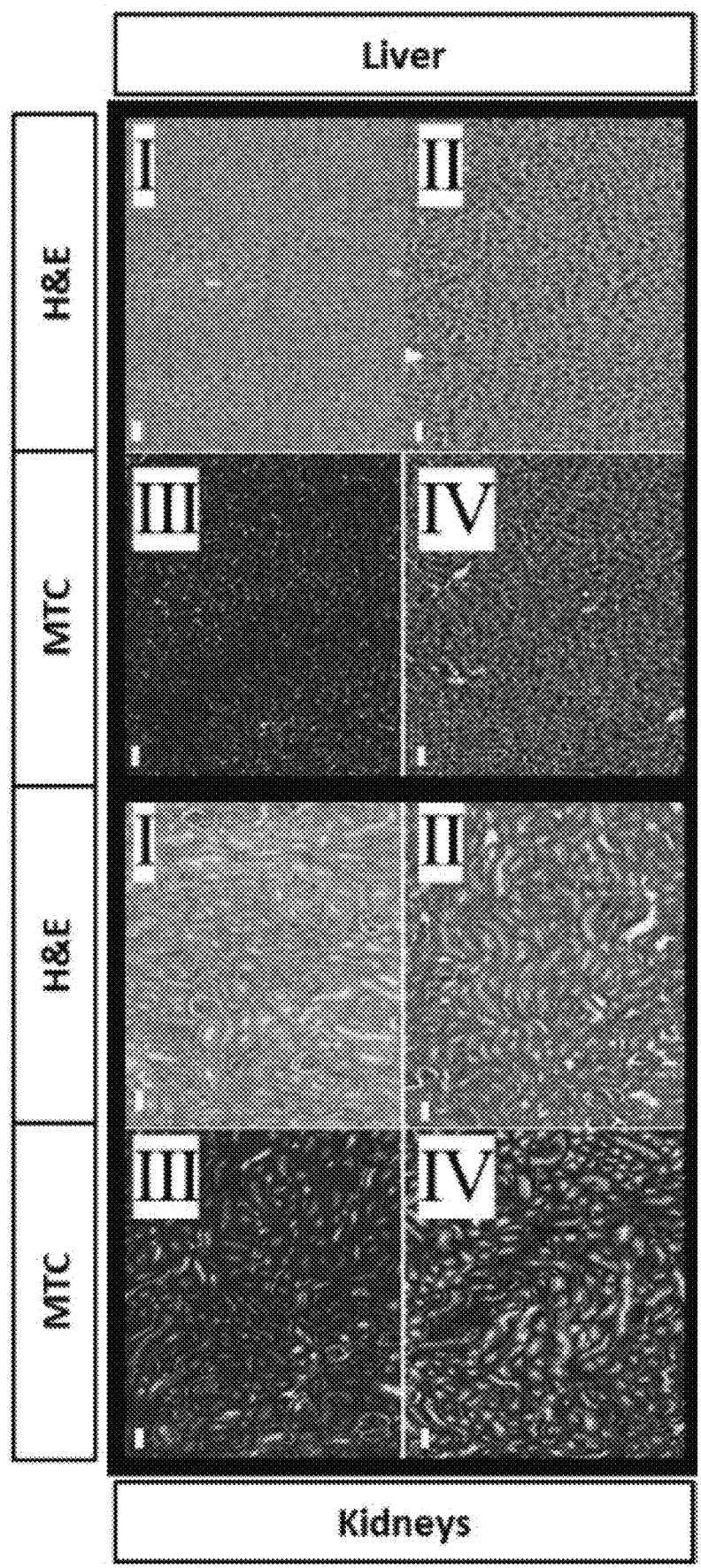
Figure 5C:
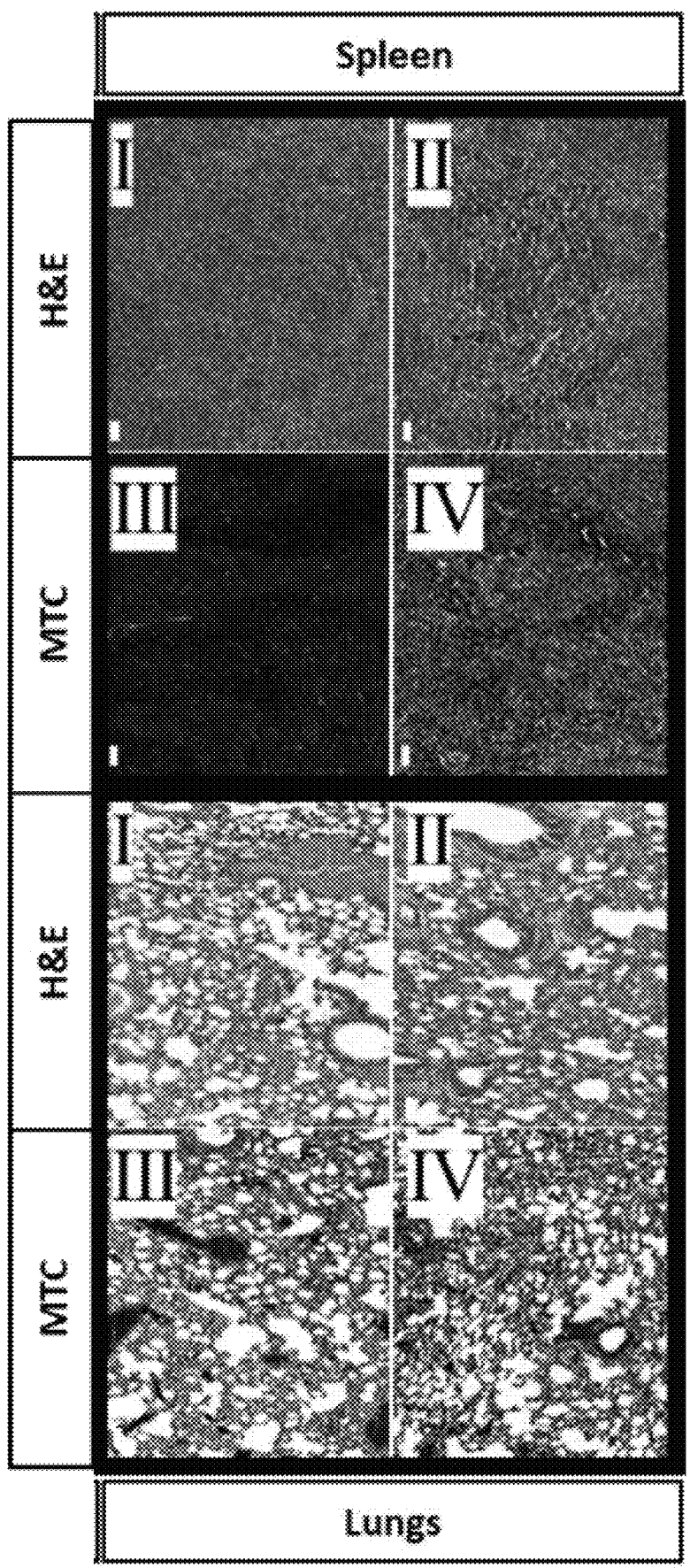
Figure 5D:
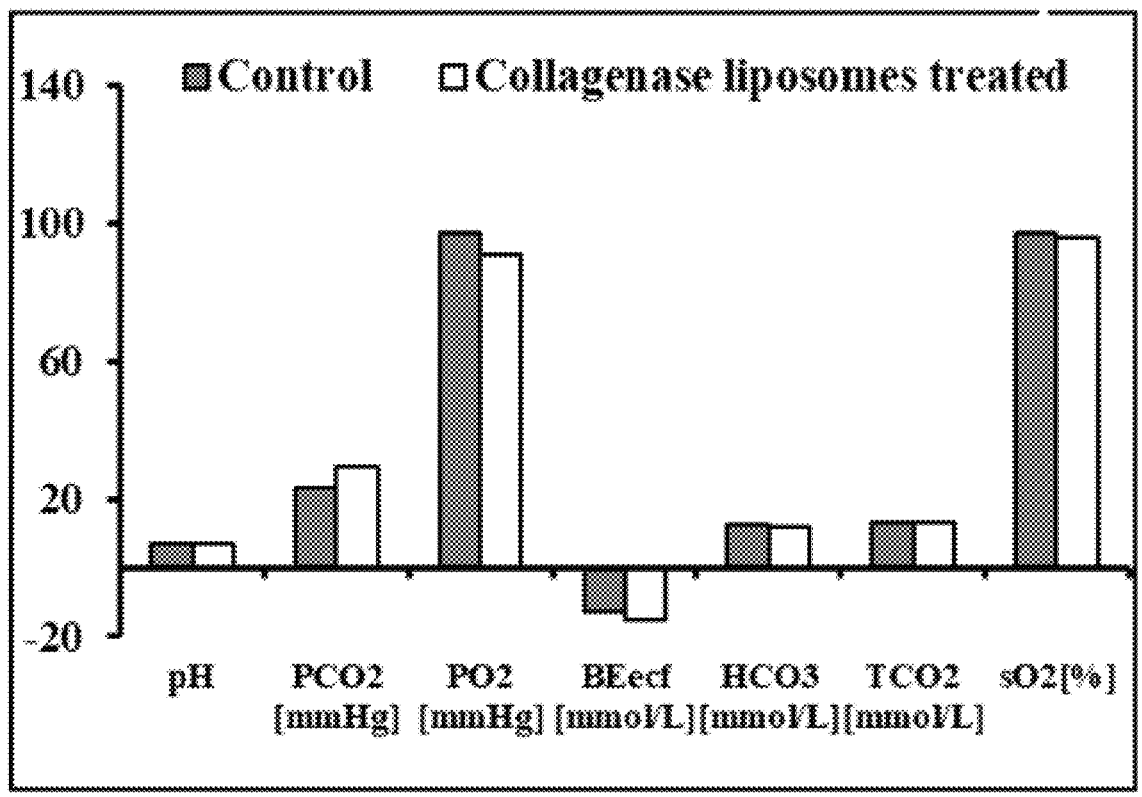
Figure 5E:
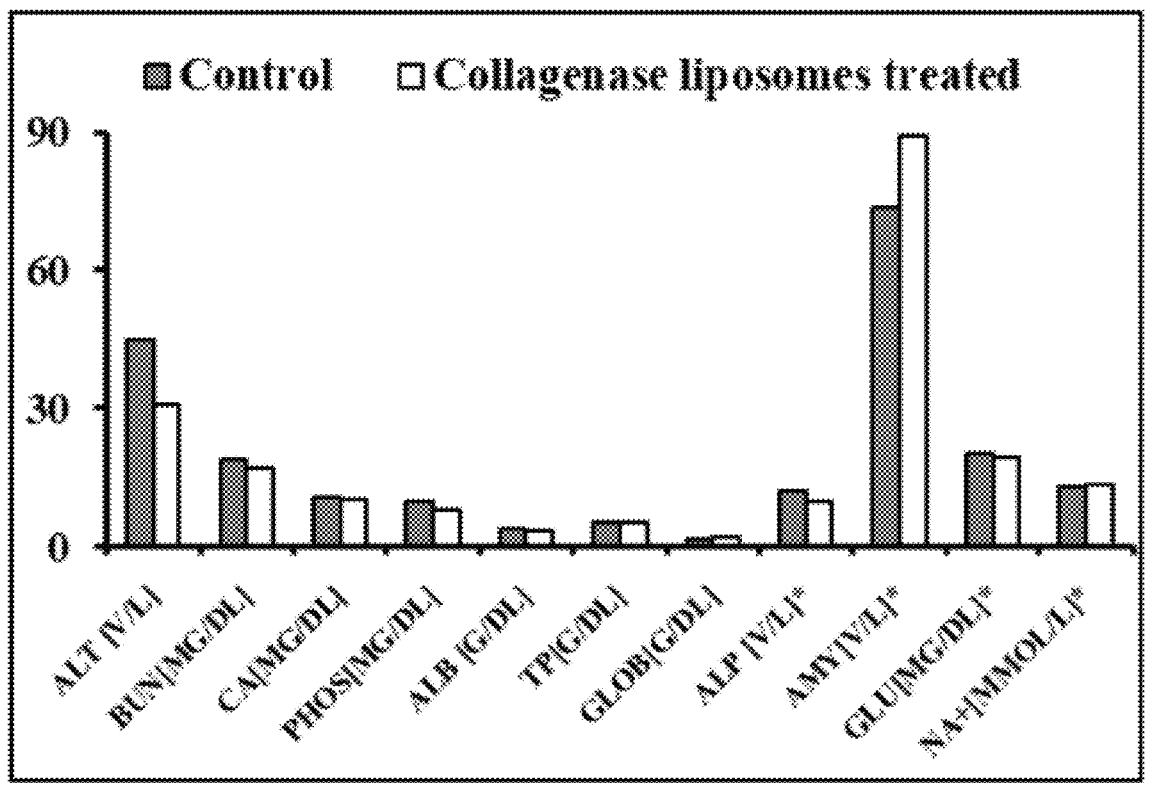
Figure 5F:
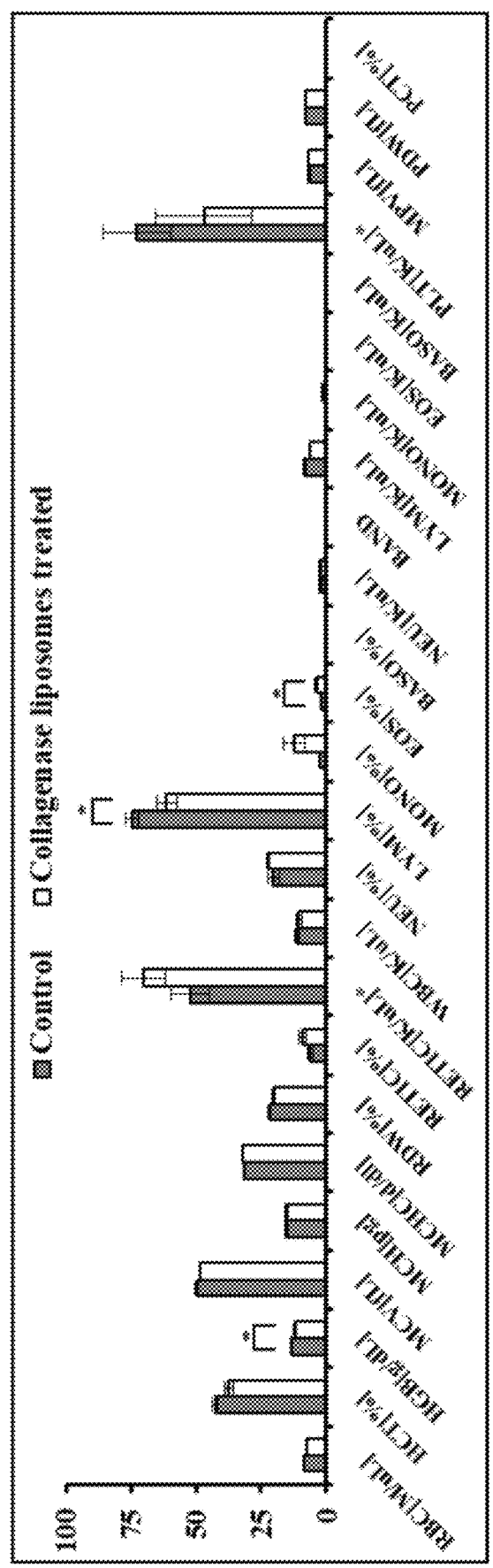

To test the safety of the collagenase treatment, we sacrificed healthy mice 24-hours after intravenous injections of liposomal collagenase. Hematoxylin and eosin (H&E) and Masson's trichrome staining of the liver, spleen, kidneys and lungs did not indicate any major physiological damage after collagenase treatments (FIG. 5C). To evaluate the effect of collagenase on organ function we collected blood from the control and test groups (n=4 biological replicates). Several differences were noticed when comparing blood gases and a chemistry blood panel in the collagenase treated and untreated mice (FIG. 5D-E). Specifically, a difference was recorded in alanine transaminase (ALT) which was higher in the control group, and amylase (AMY) which was higher in the test group (FIG. 5E). In a complete red blood cell analysis, somewhat higher levels of hemoglobin (HGB) and lymphocytes (% LYM) were observed among the control group, while higher levels of eosinophils (% EOS) were observed among the test group, however, all fall within normal blood ranges (n=4 biological replicates, FIG. 5F). The ability of healthy, but not diseased, tissue to withstand the collagenase treatment, is explained by normal homeostasis that regulates collagenase concentrations by secreting tissue inhibitor matrix metalloproteases (TIMP).

Example 5

Liposomes Versus Free Collagenase

Figure 6A:
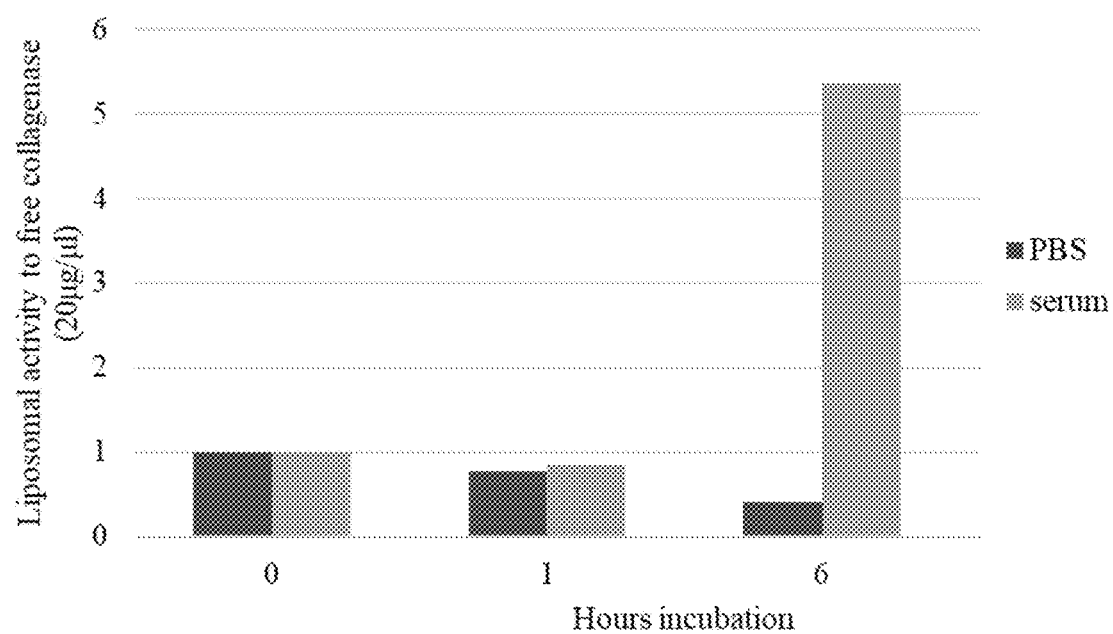
FIGS. 6A-H: Liposome encapsulated collagenase is superior to free collagenase. (6A) A bar graph of encapsulated collagenase activity standardized to the activity of free collagenase. (6B-G) Bar graphs showing the penetrance of (6B, 6E) 100 nm, (6C, 6F) 20 nm, and (6D, 6G) 5 nm gold particles into various (6B-D) tissues or (6E-G) tissues and bodily fluids after pre-administration of empty liposomes, free collagenase or liposome encapsulated collagenase. (6H) A bar graph of relative pancreases (or pancreases and tumor) size after treatment with Paclitaxel and pretreatment with empty liposomes, free collagenase and liposome encapsulated collagenase. Results are standardized to the size of a healthy pancreas and representative images of the excised pancreases/tumors are shown.

In order to quantify the protective nature of liposome encapsulation versus free collagenase, both free enzyme and encapsulated enzyme were incubated in PBS or serum and protein activity was measured by Enzcheck Assay at 0, 1, 6 and 24 hours. After 6 hours in serum the activity of the encapsulated enzyme was greater than 5 times higher than free enzyme, attesting to the protective effect that lipid encapsulation has on the enzyme (FIG. 6A).

Figure 6B:
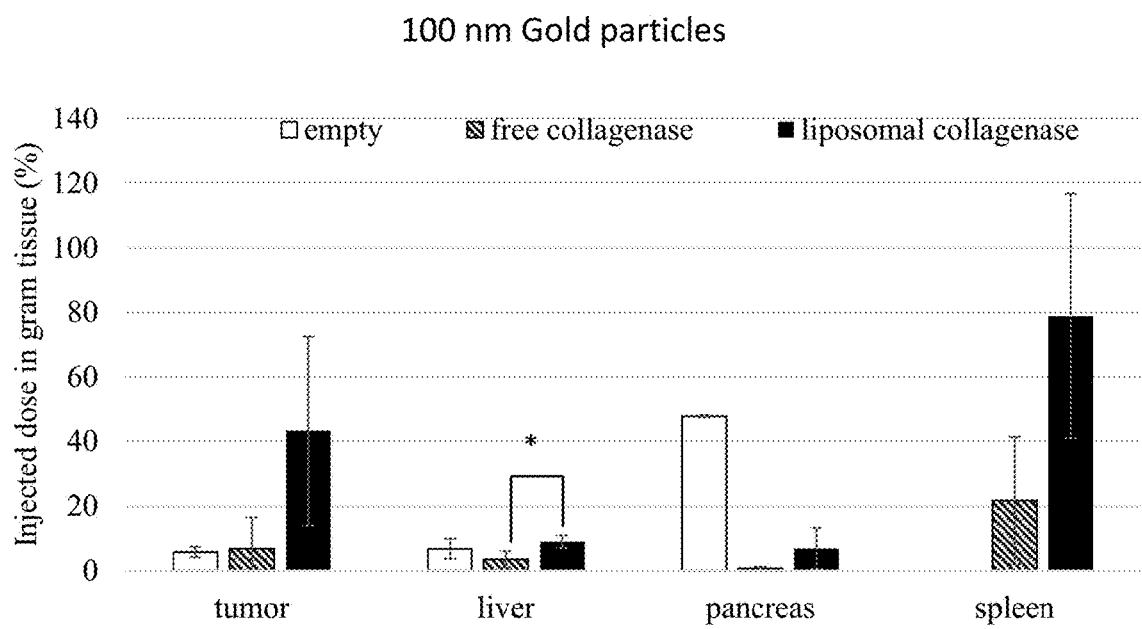
Figure 6C:
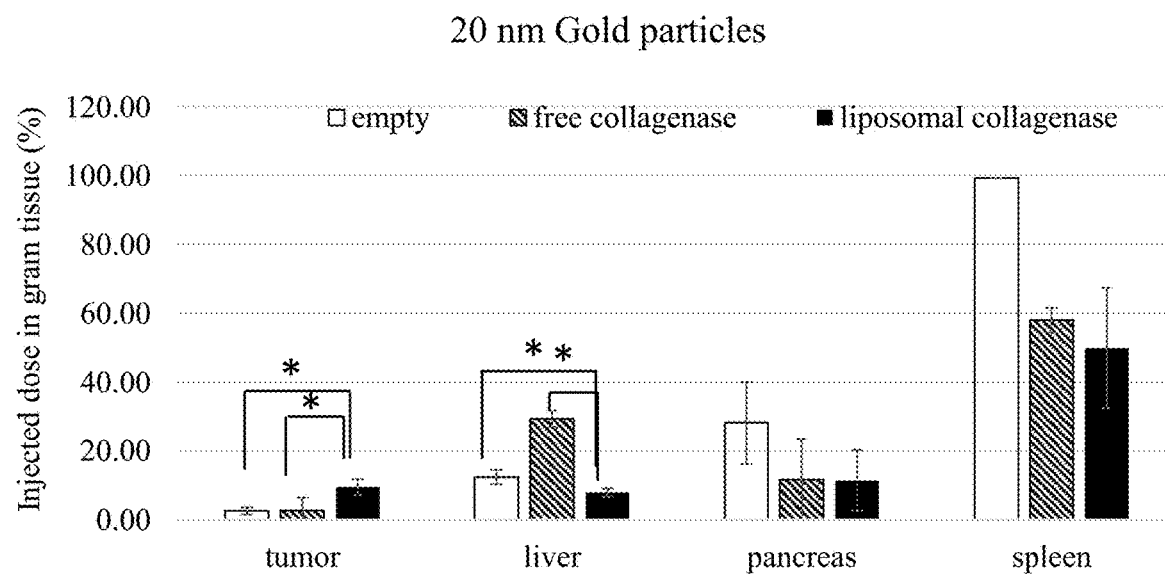
Figure 6D:
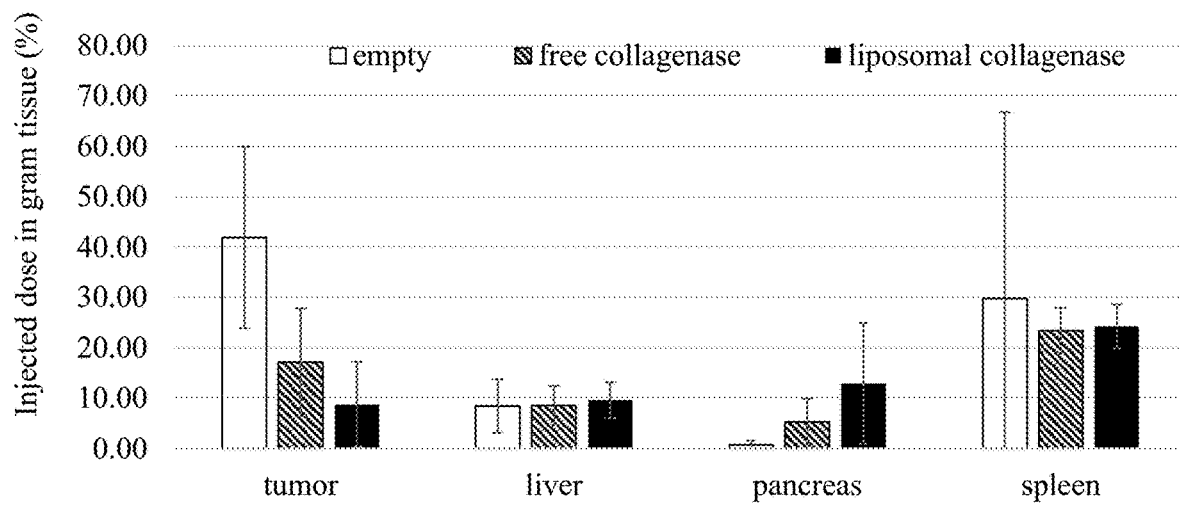
Figure 6E:
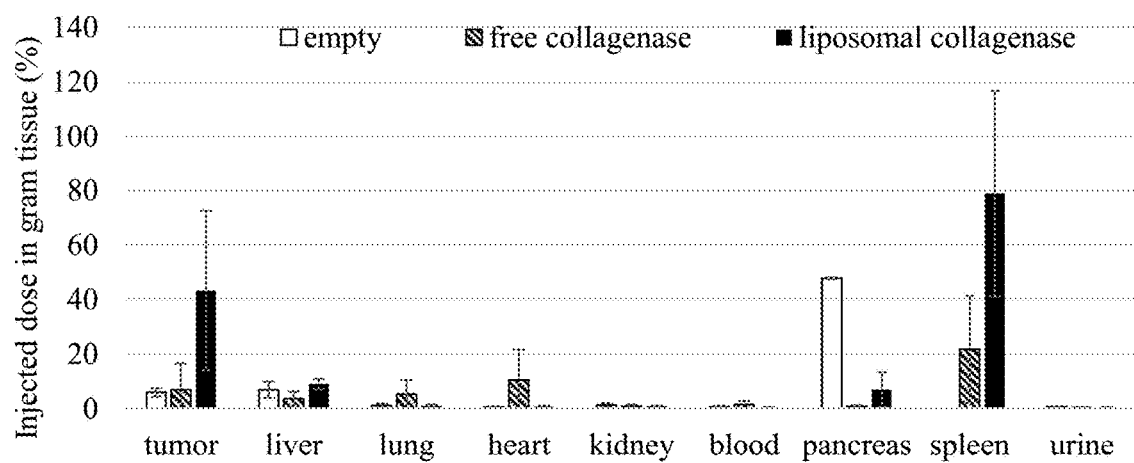
Figure 6F:
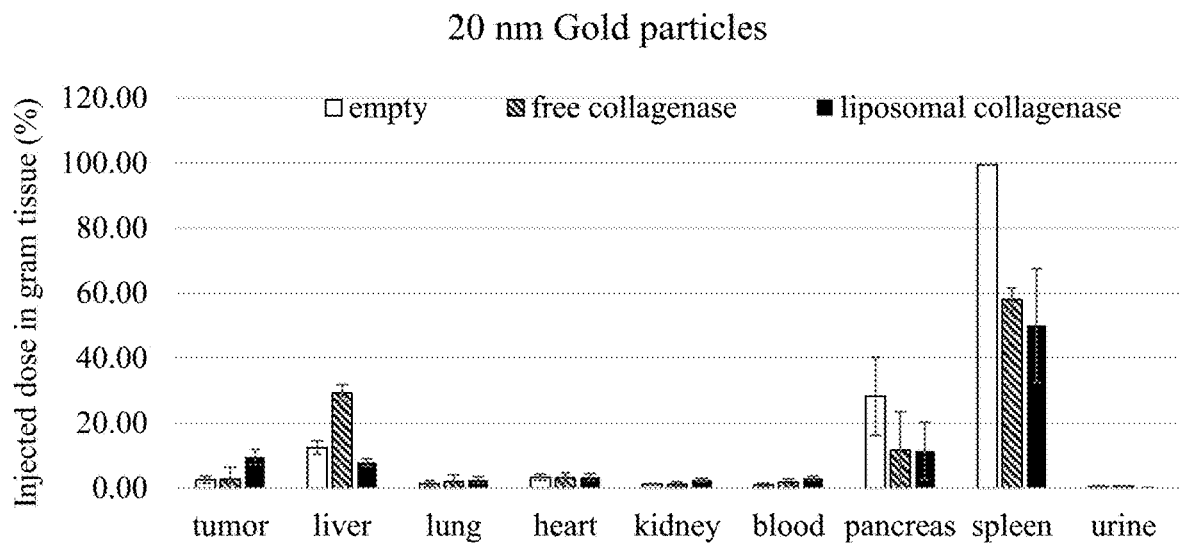
Figure 6G:
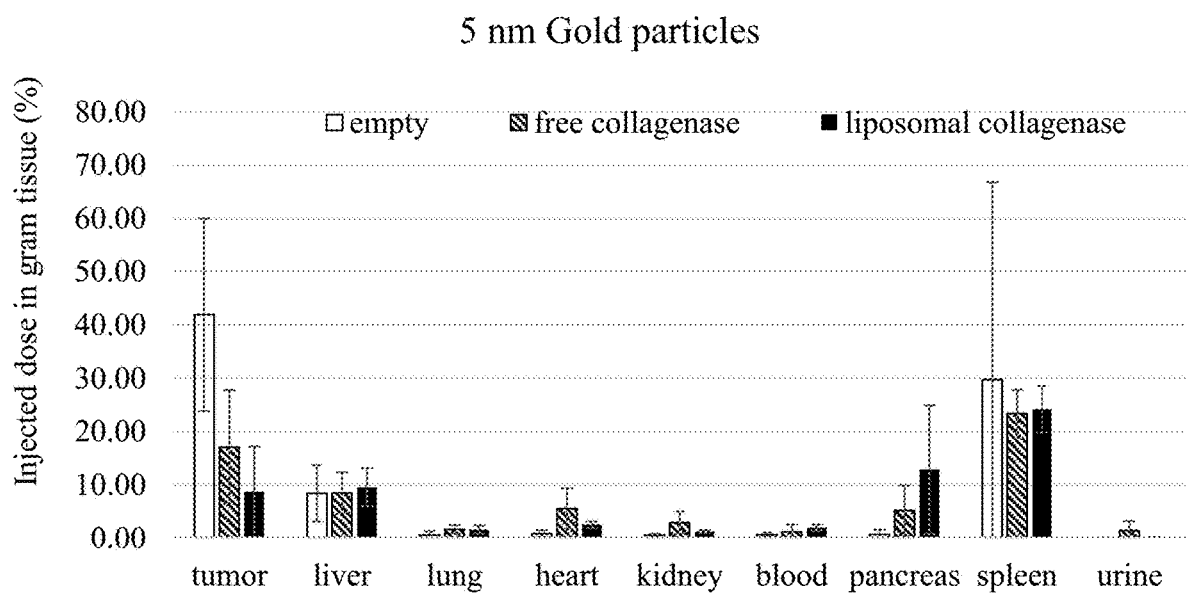

In order to quantify the extent to which encapsulation of collagenase in liposomes improved drug penetrance over free collagenase, PDAC mice were pretreated (intravenous injection twice, 24 hours apart) with empty liposomes, free collagenase or liposome encapsulated collagenase and then 24 hours later gold nanoparticles of various sizes. Specifically, 5, 20, and 100 nm gold nanoparticles were injected and gold penetrance to various organs was monitored 24 hours later. Liposome encapsulated collagenase increased the penetrance of 100 nm (FIG. 6B) and 20 nm (FIG. 6C) gold particles into pancreatic tumors as compared to free collagenase and empty liposomes. The penetrance of 100 nm particles into liver was also significantly increased with encapsulated collagenase as opposed to free collagenase, while increases into pancreases and spleen were not significant (FIG. 6B). Interestingly, the penetrance of 20 nm particles was only increased in tumors (FIG. 6C). 5 nm particles actually had decreased penetrance into tumors after treatment with collagenase whereas no significant change was observed in other organs (FIG. 6D). The experiment was repeated, and more organs/bodily fluids were examined, but similar results were obtained (FIG. 6E-G).

Figure 6H:
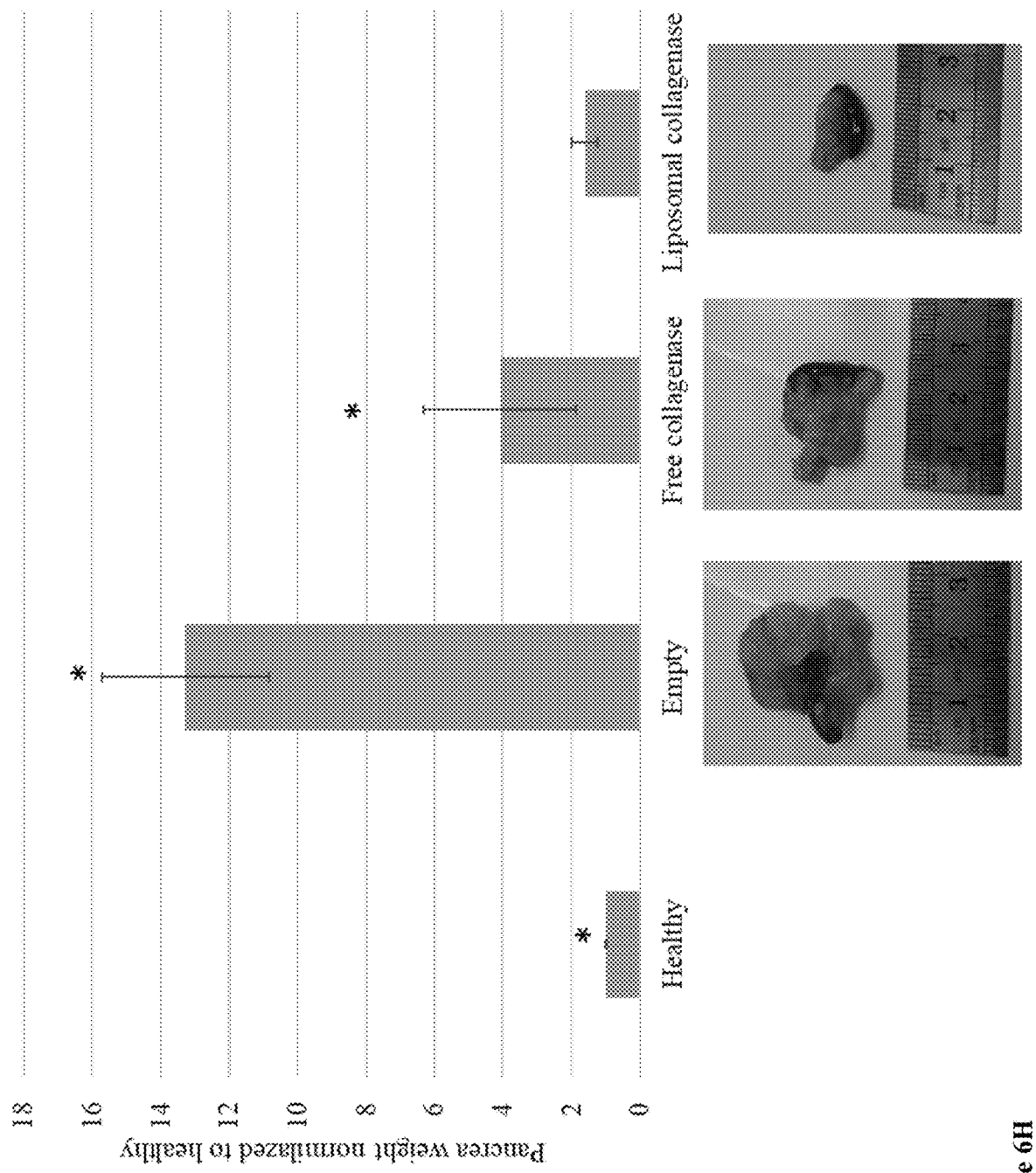

Next PDAC mice harboring tumors were pretreated with empty liposomes, free collagenase or liposome encapsulated collagenase (intravenous injection twice, 48-72 hours apart) followed 48-72 hours later by treatment with Paclitaxel micelles (10 mg/kg) which are about 20 nm particles. This treatment cycle was in total 1 week long and was repeated for a second and third week, for a total of 21 days of treatment. At the end of the third cycle the mice were sacrificed, and the tumors excised and weighed. Encapsulation of collagenase decreased the tumor size by greater than 50% as compared to free collagenase (FIG. 6H) and by more than 90% as compared to no collagenase treatment.

Example 6

Collagenase Nanoparticles Inhibit Early Activation of the Enzyme

Figure 7A:
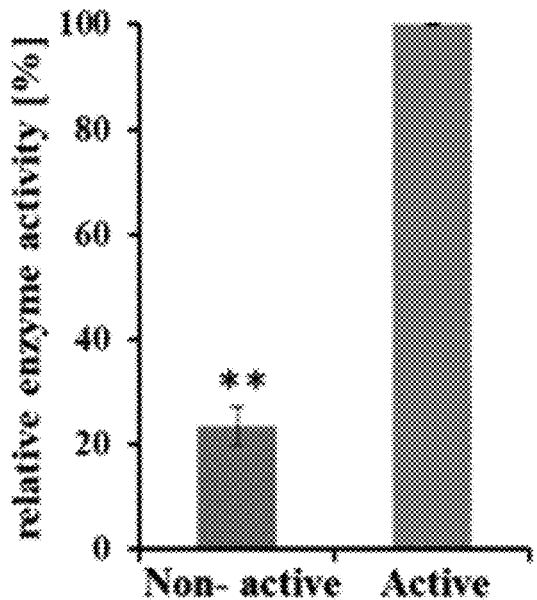
FIGS. 7A-M: Nanosurgery. Controlled release and activation. (7A) Bar graph of collagenase activity. (7B) Line graph of the activity of the collagenase, over a period of 6 hours. (7C) Empty and collagenase-encapsulated liposomes were formed in a PBS-buffer with $Ca^{+2}$ ions. 1 hour later, the liposomes were dissolved using methanol, and the lipid profile was compared by thin layer chromatography (mobile phase composition: chloroform, methanol and water with ratio of 75:20:5 vol), versus the pure components: collagenase, cholesterol, DSPE-PEG 2000 and DMPC. The liposome components have similar retention spots compared to their respective control test. (7D) Line graph of collagenase released from the nanoparticles over 48 hours at physiological conditions. (7E) Cryo-TEM images of collagenase-encapsulated liposomes as well as characterization by Zetasizer Nano ZSP. Scale bar=5 nm. (7F-H) Collagen fibers were exposed to collagenase at various concentrations for different periods of time. (7F) Cartoon of the fibers stressed using a force machine under oral physiological conditions. (7G) A line graphs showing time to rupture with various collagenase concentrations. The higher collagenase concentrations (0.5 and 1 mg/mL) degraded the collagen fibers within less than 10 hours. A therapeutic window of 0.05-0.1 mg/ml at which the collagen fibers were relaxed but not fully degraded by collagenase was determined. (7H) Line graphs of individual fibers response to strain with and without collagenase treatment. Each fiber served as is its own control by exposing half the fiber to collagenase and the other half to an aqueous buffer. Each fiber was cut to proximal and distal sections. Each section was stressed using an Instron force machine and the mechanical characteristic was recorded. (7I-K) Images of a collagen fiber (beneath the optical field) with adherent fibroblasts during the process of collagenase treatment, at time point (7I) zero minutes (7J) 33 minutes and (7K) 80 minutes. As the collagen fiber relaxes, the adherent fibroblasts change their morphology from an elongated structure to a round structure. Error bars indicate the standard deviation of at least five independent measurements. *denotes a two-tailed p-value<0.05. **denotes a two-tailed p-value<0.01. (7L) Line graph of collagenase activity over time at 4 degree. (7M) Bar graph of collagenase activity after 24 hours at 4 and 37 degrees.
Figure 7B:
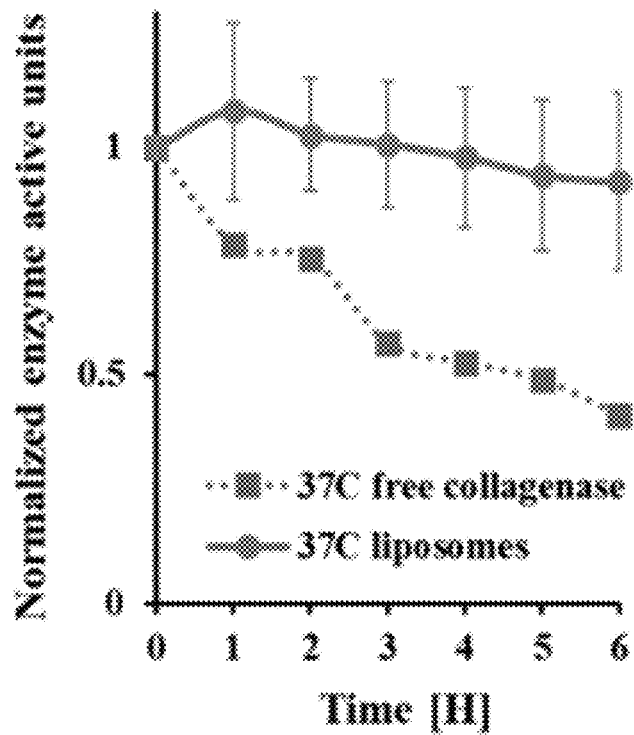
Figure 7C:
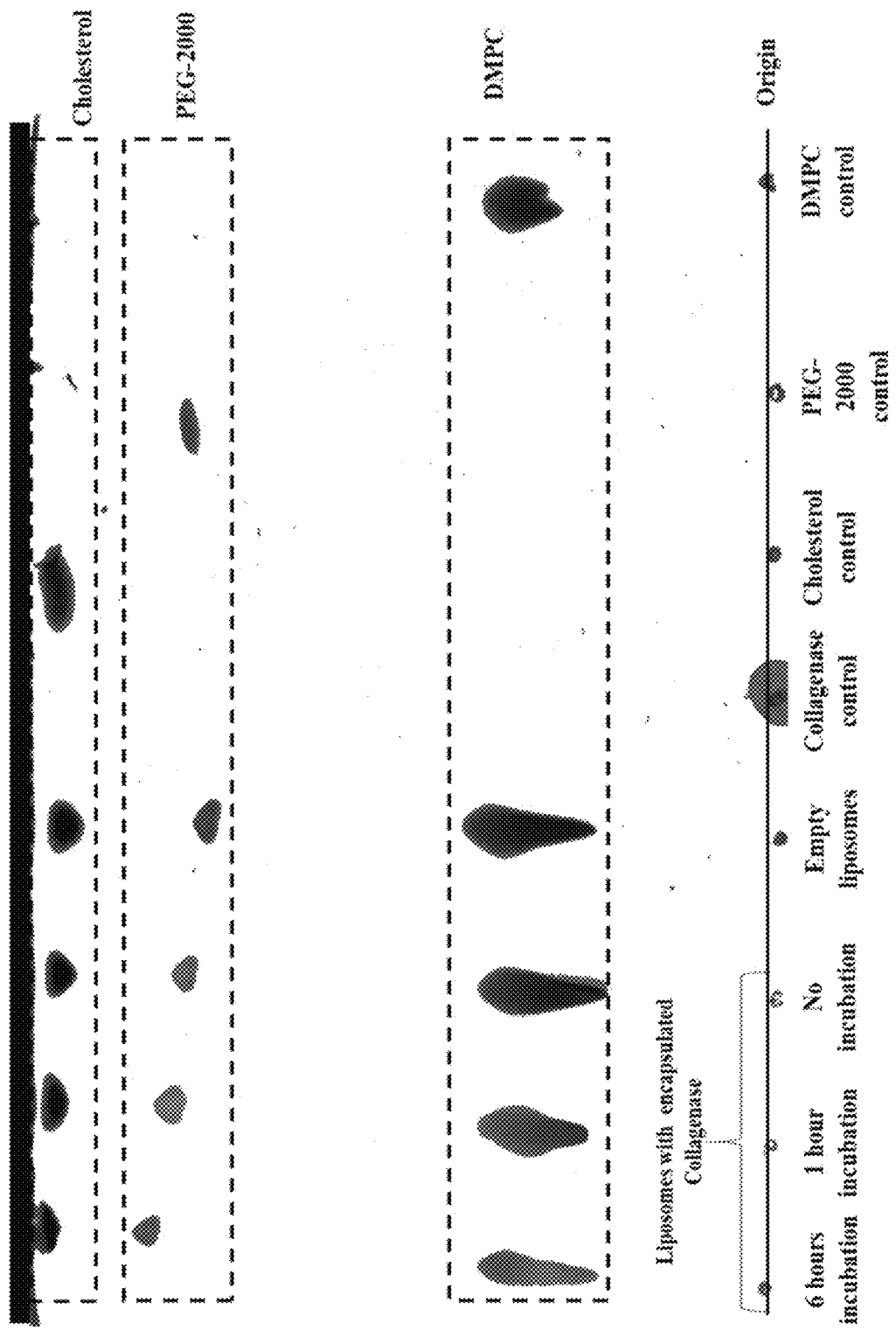
Figure 7D:
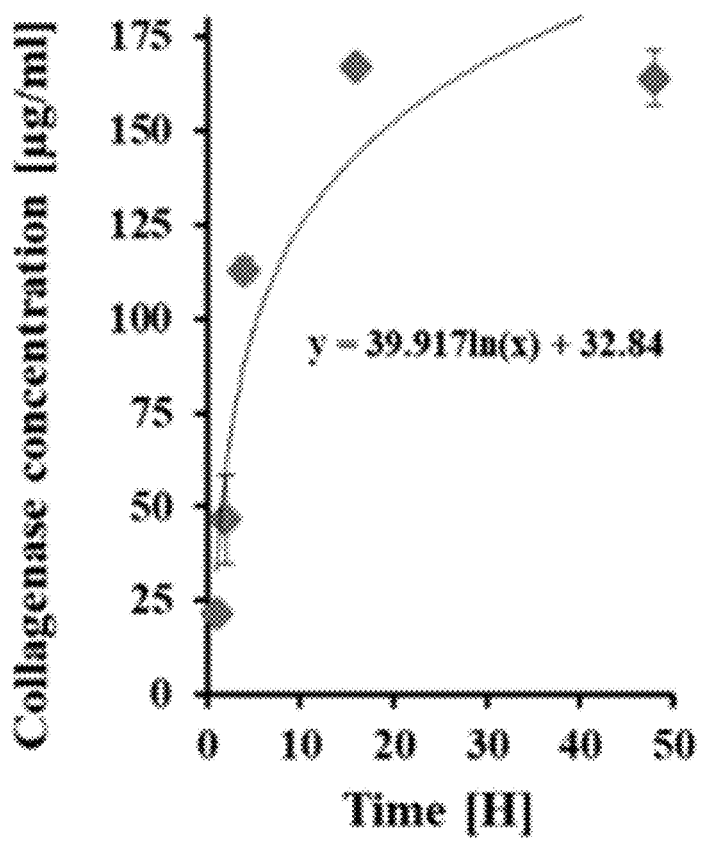
Figure 7E:
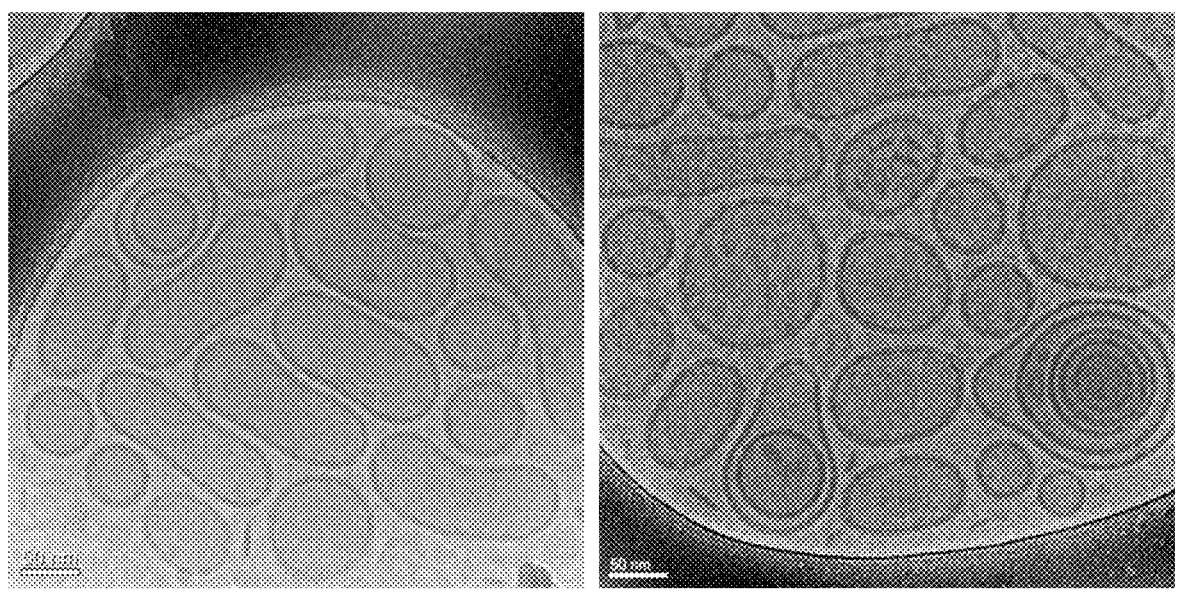
Figure 7E:
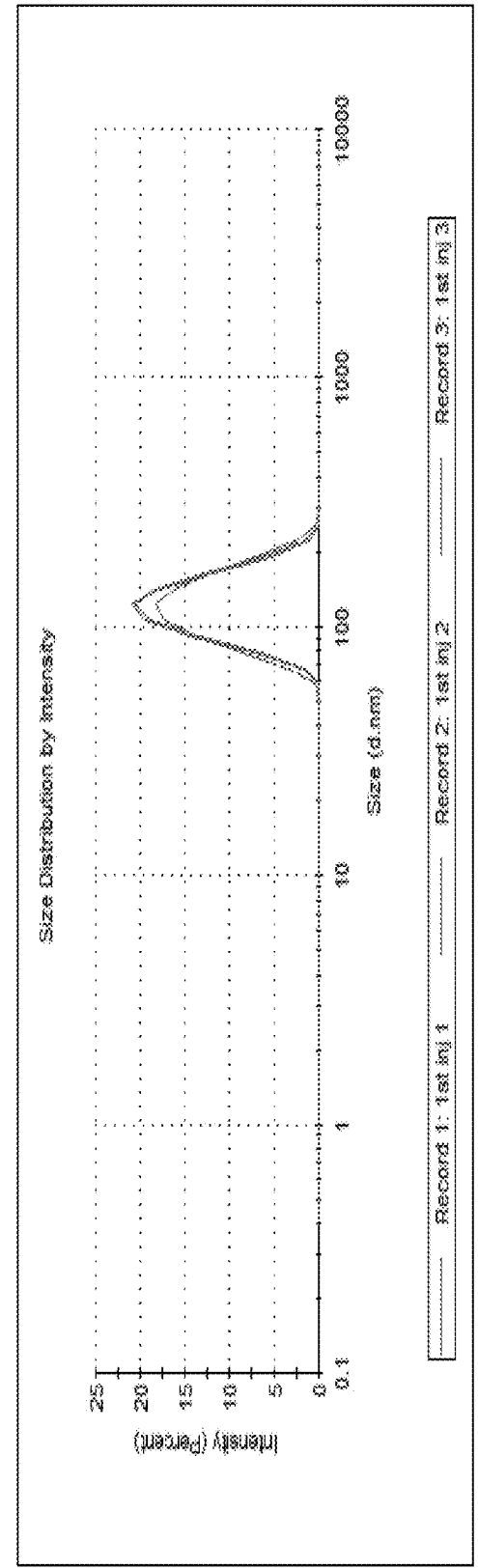

Experiments were conducted to better understand the enzyme protection afforded by encapsulation in liposomes. Collagenase is activated by calcium, its biological cofactor, which catalyzes the proper folding of the enzyme and enables collagenase binding to its collagen substrate (FIG. 7A). Once activated, the half-life of collagenase is several hours until it is retarded by metalloproteinase inhibitors or by other physiological conditions (FIG. 7B). We sought to develop a system in which collagenase is activated only after it reaches the desired site of action. For this, we loaded collagenase into the 100-nm liposomes in the absence of Ca. The liposomal lipid bilayer, composed of 1,2-dimyristoyl-sn-glycero-3-phosphocholine (DMPC), is impermeable to $Ca^{2+}$ ions (FIG. 7B). This impermeability protects the enzyme from early activation (FIG. 7A-B). This was true even at 4 degrees (FIG. 7L), although the protection was significantly greater at 37 degrees (FIG. 7M). The liposome lipids were not susceptible to degradation by collagenase (FIG. 7C). Once placed in the sulcus, collagenase began diffusing out of the liposomes (FIG. 7D-E). Naturally present in the oral cavity, the calcium activated the enzyme, which in turn began relaxing the collagen fibers (FIG. 7F-G).

Figure 7F:
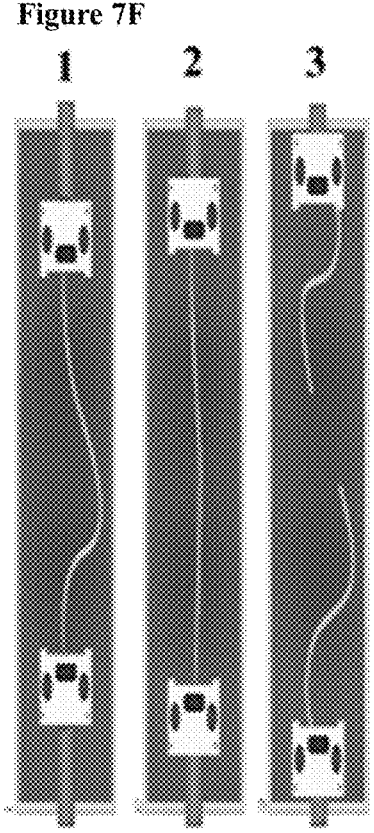
Figure 7G:
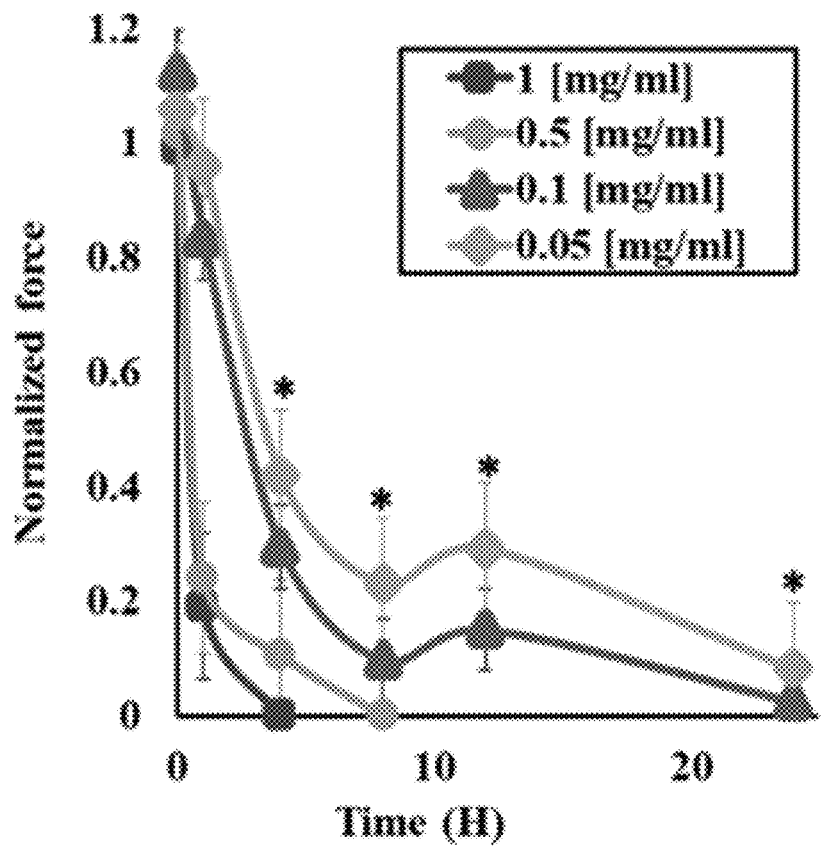

More than 300 collagen fibers were stressed in the presence of collagenase at different concentrations using an experimental setup that mimics physiological condition (FIG. 7F). The tensile strength of each collagen fiber was measured as a function of the collagenase concentration and treatment time. As the concentration of collagenase increased the fibers weakened (FIG. 7G). During this process, a therapeutic collagenase concentration of 0.05-0.1 mg/mL was determined, at which the fibers relaxed but did not tear. We expressed the relative change in fiber strength during the treatment using a dimensionless number, α:

$$\alpha = \frac{\text{Force needed to tear a collagenase treated fiber}}{\text{Force needed to tear an untreated fiber}}$$

Figure 7H:
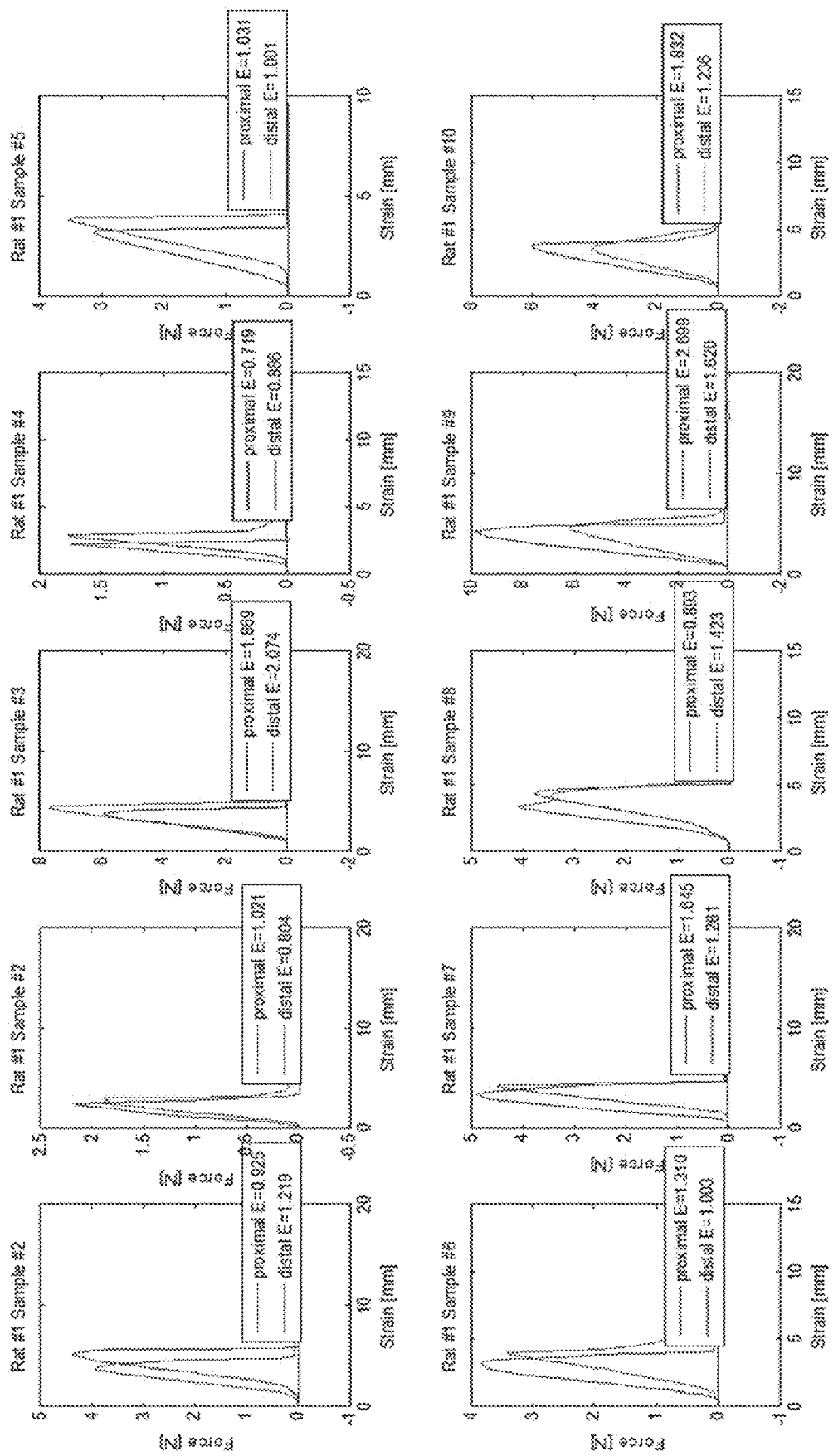
Figure 7H:
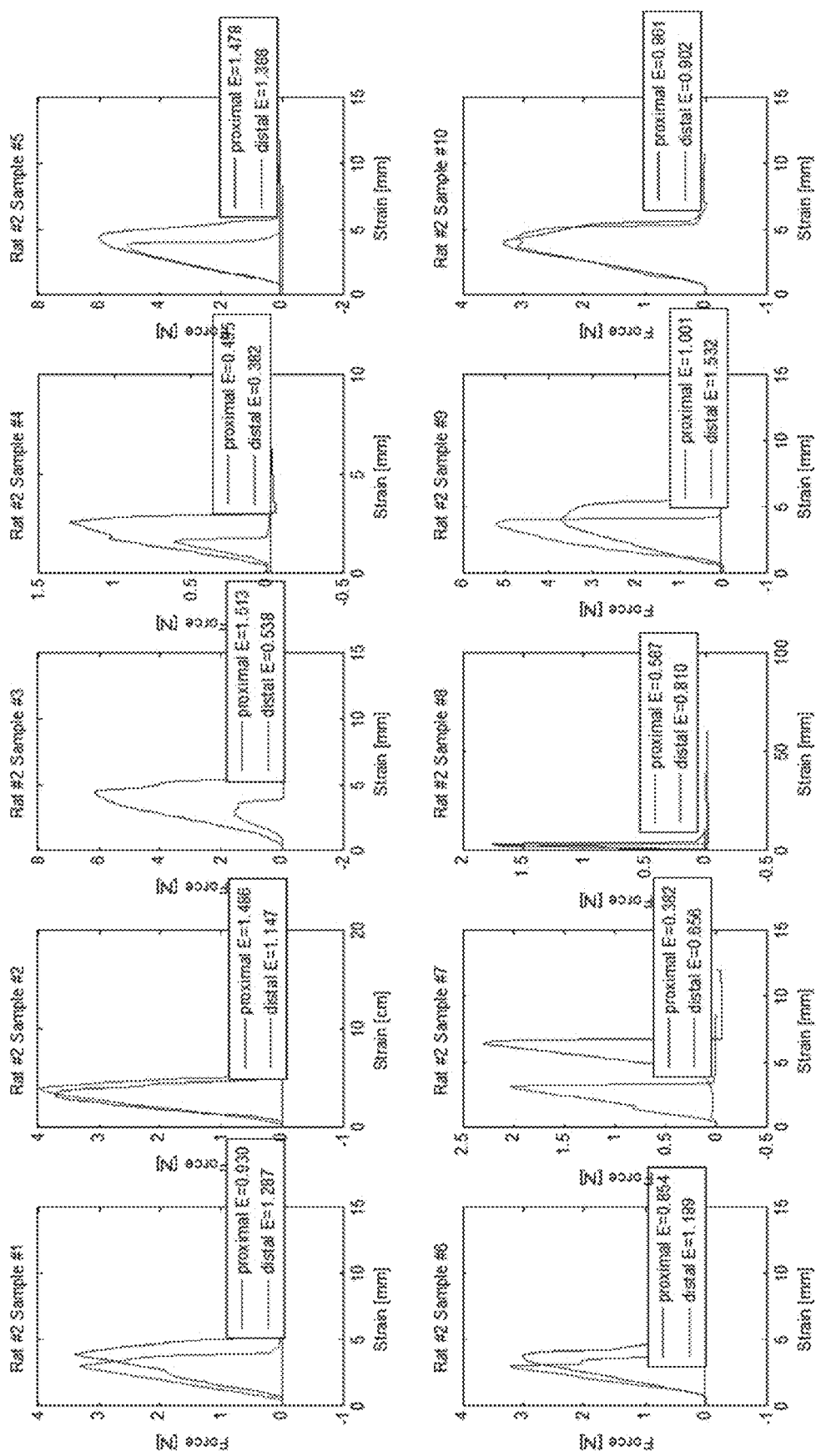

A descending α slope implies that the collagen bundle is weakening, while an ascending slope implies that a reparative process is occurring. Three modes of α can be noticed, as the collagen bundles are being exposed to collagenase (FIG. 7G-H). At first, rapid weakening of the fibers treated with collagenase was recorded ($0<\alpha<0.2$). Thereafter, some strengthening of the collagen fibers occurred ($0.2<\alpha<0.4$) followed by gradual collagen weakening until the fiber tore ($\alpha=0$). The weakening of the collagen is intuitive due to the degradative activity of the collagenase. However, the strengthening of the fiber suggested that endogenous collagen repair mechanisms are activated after the fiber is exposed to collagenase.

Figure 7I:
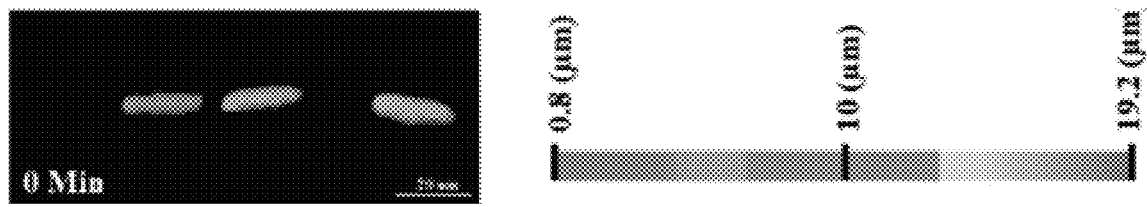
Figure 7J:
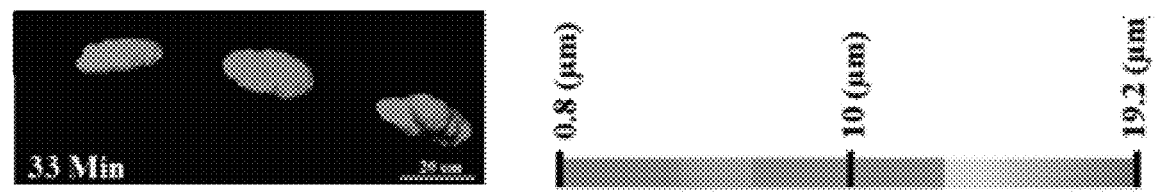
Figure 7K:
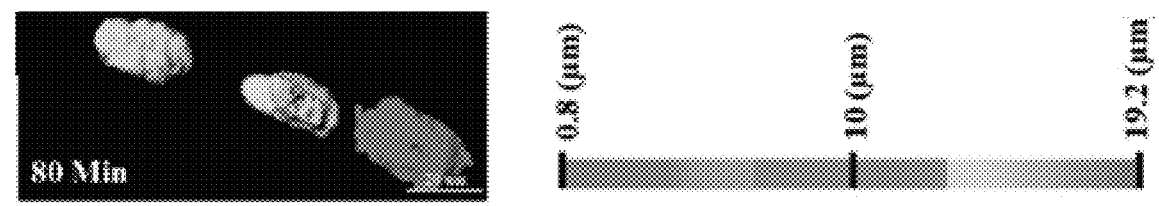
Figure 7L:
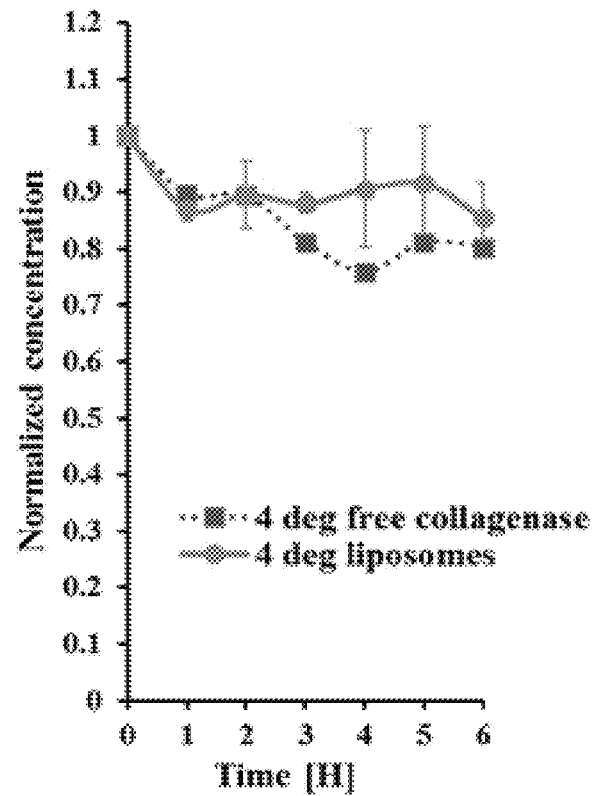
Figure 7M:
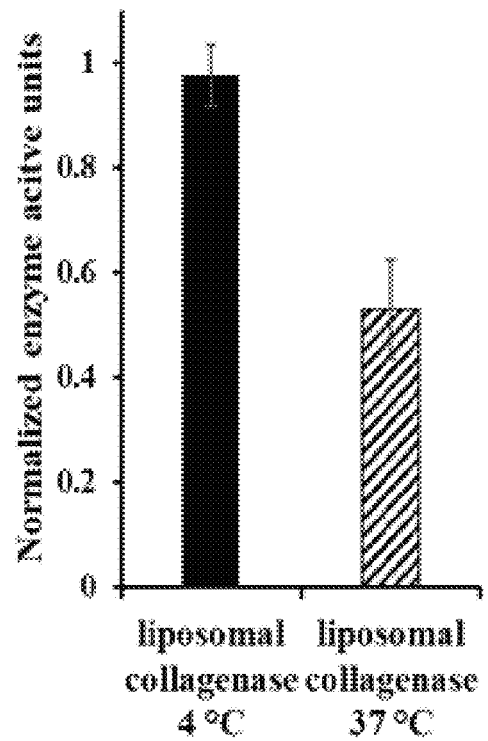

Fibroblasts play an important role in collagen remodeling. Adherent to the collagen fibers, fibroblasts sense the fiber tension and initiate regenerative processes when the fiber is degraded. Using a time-lapse laser scanning confocal microscopy, we imaged the fibroblast morphology in response to the collagenase treatment (FIG. 7I-K). When the fiber was stretched, the fibroblasts had an elongated, ellipse morphology (FIG. 7I). Due to the exposure to collagenase, the fiber relaxed, and the fibroblasts assumed a round structure (FIG. 7J-K). Interestingly, throughout the process we did not observe fibroblast detachment from the fiber and fibroblast viability was retained (FIG. 7I-K). This finding suggests that natural reparative processes can be carried out by the adherent fibroblasts.

Example 7

Collagen Regeneration

Figure 8A:
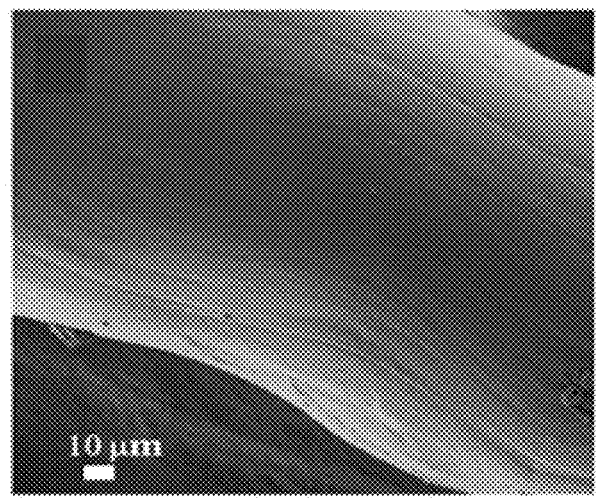
FIGS. 8A-E: Collagen regeneration. A collagen fiber imaged using HR-SEM (8A) before (8B) during and (8C) after being exposed to collagenase, allowing collagen regeneration. (8D) Bar graph of fiber strength before adding the collagenase, during the collagenase disassembling activity (8 h), and after the collagenase activity was retarded (16 h). The collagen fibers regained ~90% of their initial strength profile. All data points are the mean of 14-20 experiments. (8E) Bar graph showing the RNA profile of Col1A1, IL1b, TNC, VEGF and TNFα (genes associated with collagen repair and extracellular matrix remodeling). β-2 microglobulin (B2M) was used as the relative housekeeping gene. *indicates a two tail, unequal variances P-Value<0.05, **indicates a two tail unequal variances P-Value<0.01. A one-way ANOVA analysis of gene expression comparing between the enzymatic nano-surgery group, the untreated, and the empty liposome treatment groups, demonstrated a significant effect of the liposome-surgery on gene expression, having a p<0.05 for the COLA1A1 gene [F(3, 15)=9.05, p=0.001], IL1B gene [F(3, 16)=7, p=0.003] and TNC gene [F(3, 16)=32.9, p<0.001]. Post hoc comparisons using the Benjamini-Hochberg procedure using an error discovery rate of Q=10% indicated that for the COLA1A1 gene the mean score of nano-surgery group plus braces (M=2.3, SD=0.6) was significantly different than the control empty liposome group (M=0.64, SD=0.16). However, did not significantly differ from the control-untreated group (M=1, SD=0.07). For the IL1B gene the mean score of nano-surgery group plus braces (M=2.5, SD=0.5) was significantly different than the control untreated group (M=1, SD=0.2) and the control empty liposomes group (M=1.1 SD=0.1). For the TNC gene the mean score of nano-surgery group plus braces (M=2.2, SD=0.2) was significantly different than the control untreated group (M=1, SD=0.1) and the control empty liposome group (M=1.3 SD=0.01).
Figure 8B:
Figure 8C:
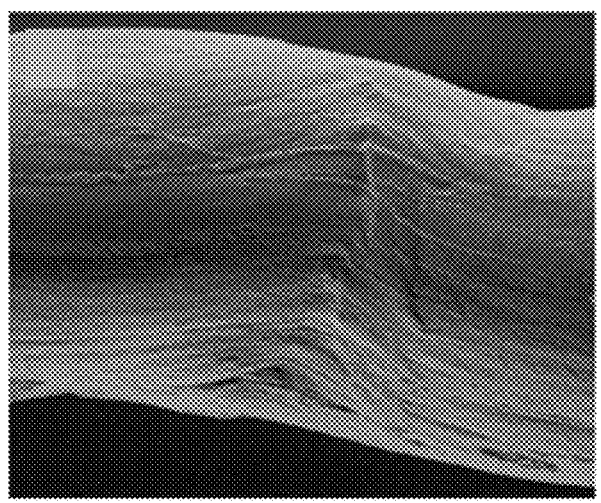
Figure 8D:
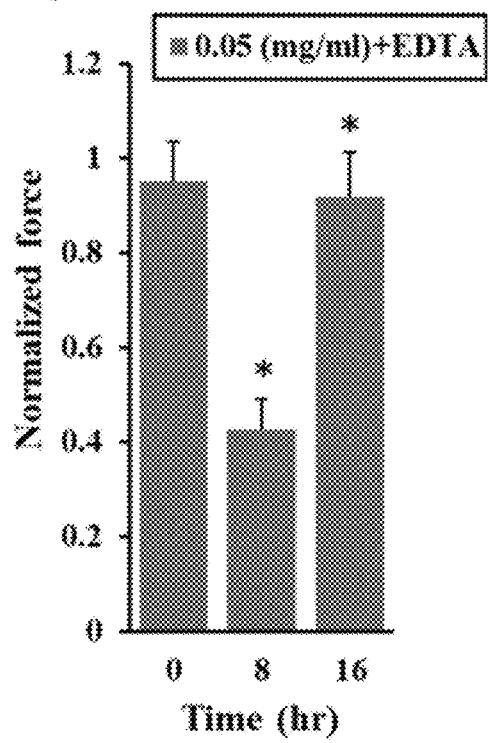

Using collagen type-I fibers sourced from a rat, we were able to observe the regenerative process after the enzymatic treatment (FIG. 8A-C). The mechanical properties of the collagen fibers were tested before, during and after the exposure to collagenase (FIG. 8D). The tensile strength of the collagen fibers was approx. 5N before being exposed to collagenase. After exposing the fibers to a therapeutic dose of collagenase, their strength decreased by approximately 50%. As expected, 16 hours after completing the process, the fibers regained their initial strength (FIG. 8D).

Throughout the treatment we imaged the morphological changes that the collagen fiber undergoes using scanning electron microscopy (FIG. 8A-C). Before the treatment we observed that the collagen has a tightly packed fiber structure. After being treated with collagenase, the collagen fibers unraveled (FIG. 8A). Several hours after retarding the collagenase activity, collagen fibers resumed their initial morphology (FIG. 8B) with the exception of some regions of the regenerated fiber which were not perfectly aligned (FIG. 8C). There is a slight discrepancy between the time it takes the fiber to reach visual repair (as seen under the electron microscope) and mechanical repair (as measured using a force machine). Even though the fiber appears regenerated, the internal molecular bonds between the collagen bundles may require more time to fully develop.

Figure 8E:
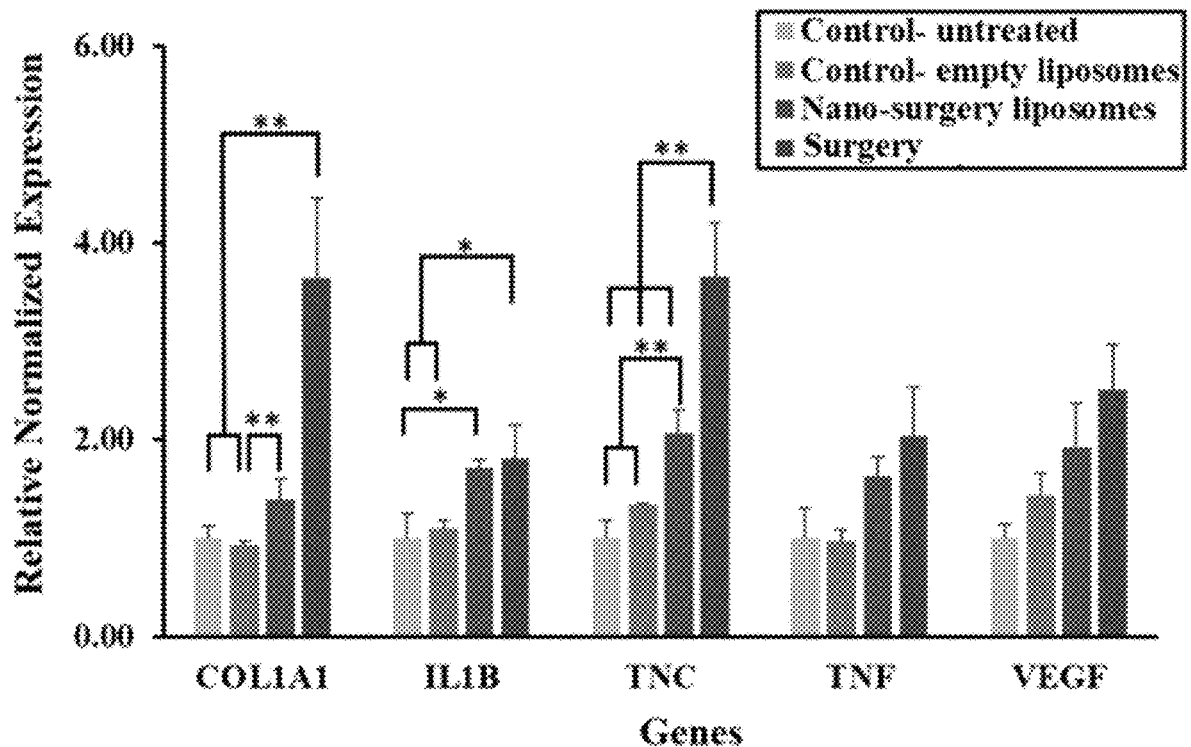

Regenerative biological cascades were triggered in response to the degradative signal. We applied collagenase type-I to rat's gingiva, in vivo. Twenty-four hours later the tissue surrounding the teeth was collected and RNA was isolated. The RNA profile of genes that are associated with collagen repair and extracellular matrix remodeling was measured (FIG. 8E). We found that multiple genes were upregulated in the treated tissue; namely, Col1a1, a gene that encodes for collagen type-I synthesis, IL1B, a gene that is associated with osteoclast activation and TNC, a gene that is expressed during remodeling of the extracellular matrix (FIG. 8E).

Example 8

Enzymatic Nano-Surgery Versus Surgery with a Scalpel

Figure 9A:
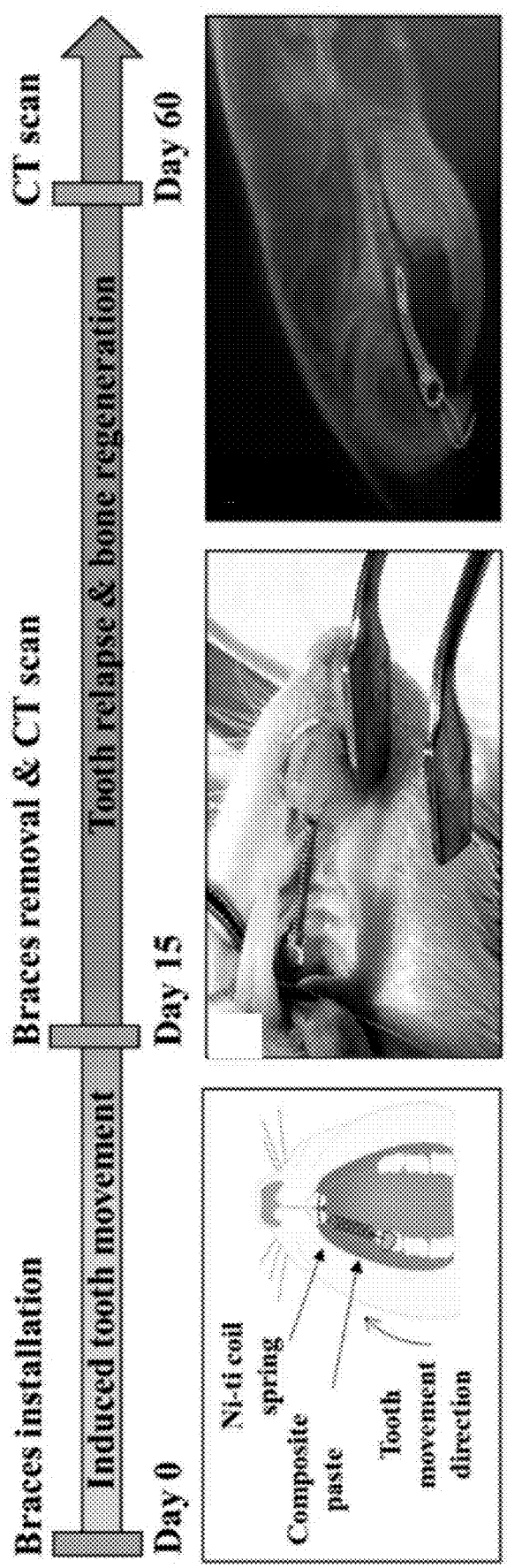
FIGS. 9A-P: Accelerating orthodontic treatments with a local application of enzymes. (9A) A diagram of the orthodontic procedure. Nanoparticles containing a therapeutic dose of collagenase (0.2 mg/ml) were inserted into the sulcus of Wistar rats. An orthodontic spring was used to connect the front upper right molar to the incisors, generating a constant pull force of 2N. A lateral X-ray scan of a Wistar rat with an orthodontic spring connecting the front upper right molar to the incisors generated a constant pull force of 2N. The gap between the front incisors and molar was measured over time using a caliper and the effect of the procedure on the underlying tissue was evaluated. (9B) Bar graph of tooth displacement. Tooth displacement was measured over a period of 15 days with and without nano-surgery or in comparison to oral surgery. Three test groups consisted of rats treated with nanoscale liposomes, free enzyme or oral surgery. Two control groups consisted of rats with braces only or a sham treatment with empty liposomes. *One-way ANOVA analysis, comparing tooth movement in the nano-surgery group plus braces versus braces alone, or to the free enzyme plus braces, or the empty liposomes (sham) plus braces, demonstrated a significant effect of p<0.05 in all four conditions [F(4, 19)=3.78, p=0.01]. Post hoc comparisons using the Benjamini-Hochberg procedure using error discovery rate of Q=10% indicated that the mean score of nano-surgery group plus braces (M=1.86, SD=0.16) was significantly different than the braces group (M=0.64, SD=0.16). However, it did not significantly differ from the surgery group (M=1.66, SD=0.26). (9C) Line graph of the biodistribution of nano-liposomes. Organs were collected at different time points with the highest florescent levels measured at the treatment site. After 4 hours a 50% decrease in the signal was recorded. After approximately 12 hours the signal was below detection (See also FIG. 9L-P). (9D) Micrographs of histological evaluation of collagenase-treated tissues. Seven days after placing the collagenase-liposomes in the rat sulcus, oral tissues of the control and treated groups were stained with H&E and Masson's trichrome. Both histological groups appear similar, specifically, no difference was noticed between the control and the treated group after 15 days of treatment surrounding the treatment area. (9E) Micrographs of axial histology cuts of the rats' gingival tissue performed in order to evaluate the damage caused by the different treatments: (left) braces, (middle) traditional surgery plus braces, or, (right) nano-surgery plus braces. Among all cuts the same mild inflammation, typical for orthodontic treatment was observed. (9F) A bar graph of the rats average weight after surgery and nano-surgery. The rat's average weight in the surgery group decreased by 8.2%, while the average weight of the rats in the nano-surgery group decreased by only 2.7%. The well-being of the rats was monitored by weighing them and following behavioral changes. The initial weight drop in both groups is attributed to an oral procedure, and is expected in orthodontic treatments, over the first 5 days. No unusual behavioral changes were observed. (9G-J) Lateral and axial views of the (9G) control (braces only) and (9H) nano-surgery groups imaged by microCT on day (9G-H) 15 and (9I-J) day 60. The tooth enhanced movement can be noticed between the front and second molars and is marked with circles and arrows. Full bone regeneration was observed 60 days after initiating the treatment (45 days after removing the braces) in (9J) the nano-surgery group, but not in (9I) the normal orthodontic group. (9K) Bar graphs showing tooth movement during treatment and after treatment (relapse). (9L-O) Micrographs of florescent (ICG) liposomes placed in the sulcus and the florescent signal was recorded over time in the (9L) gingival tissue, (9M) tongue, (9N) heart and (9O) liver. Moreover, 24 hours after placing the Gd-liposomes in the periodontal pocket, less than 0.1% of the Gd placed initial dose=171.5±6.2 μg was detected in the different organs: gingival tissue, skin, lungs, brain, spleen, urinary balder, kidneys, tongue, liver, stomach and digestive system based on elemental analysis. There were no statistically significant differences between group means as determined by one-way ANOVA (F(0.03,0.09)=1.3, p=0.2) (9P) A summary table of results representative of 5 biological replicates for each organ. SD—standard deviation.
Figure 9B:
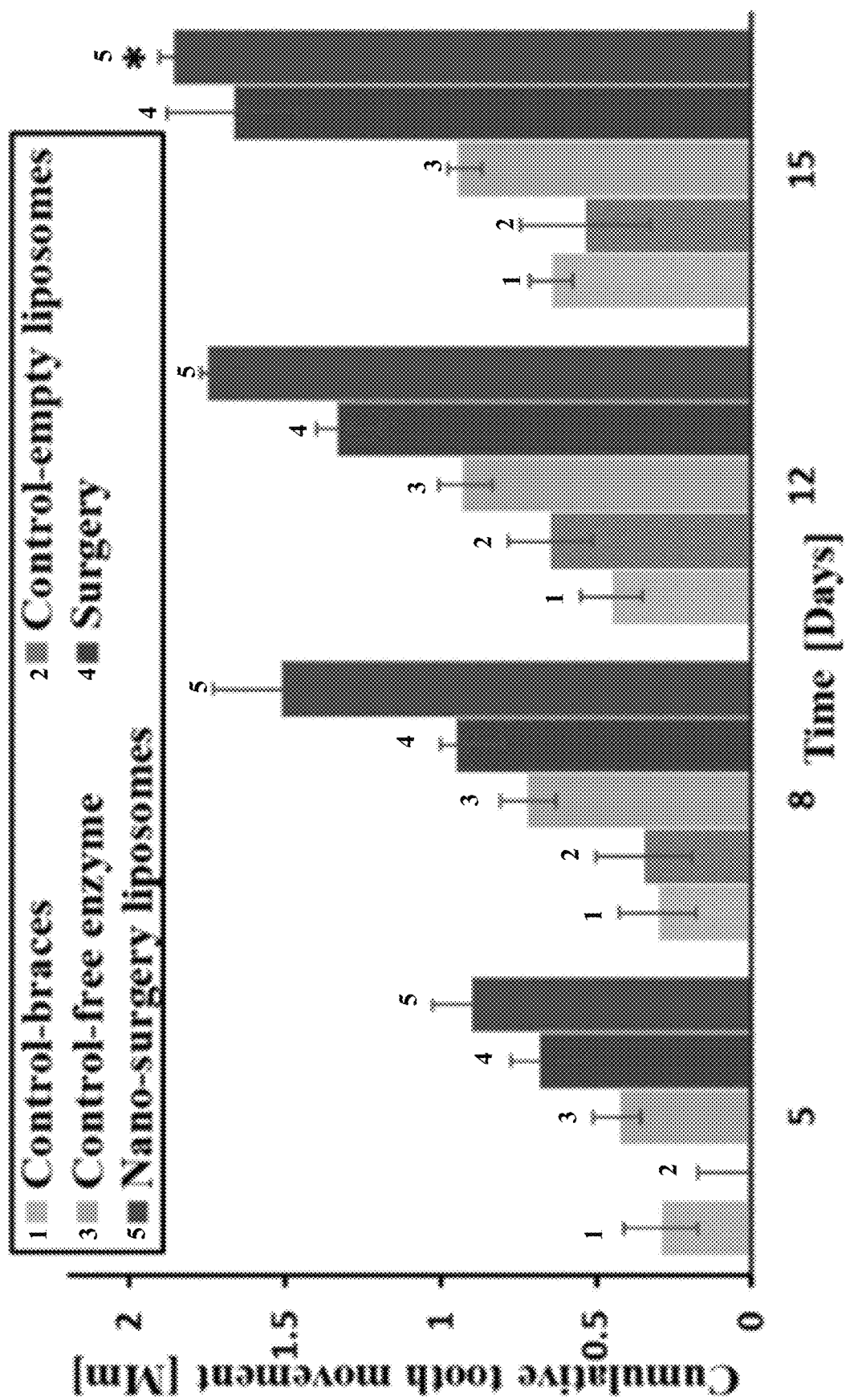
Figure 9C:
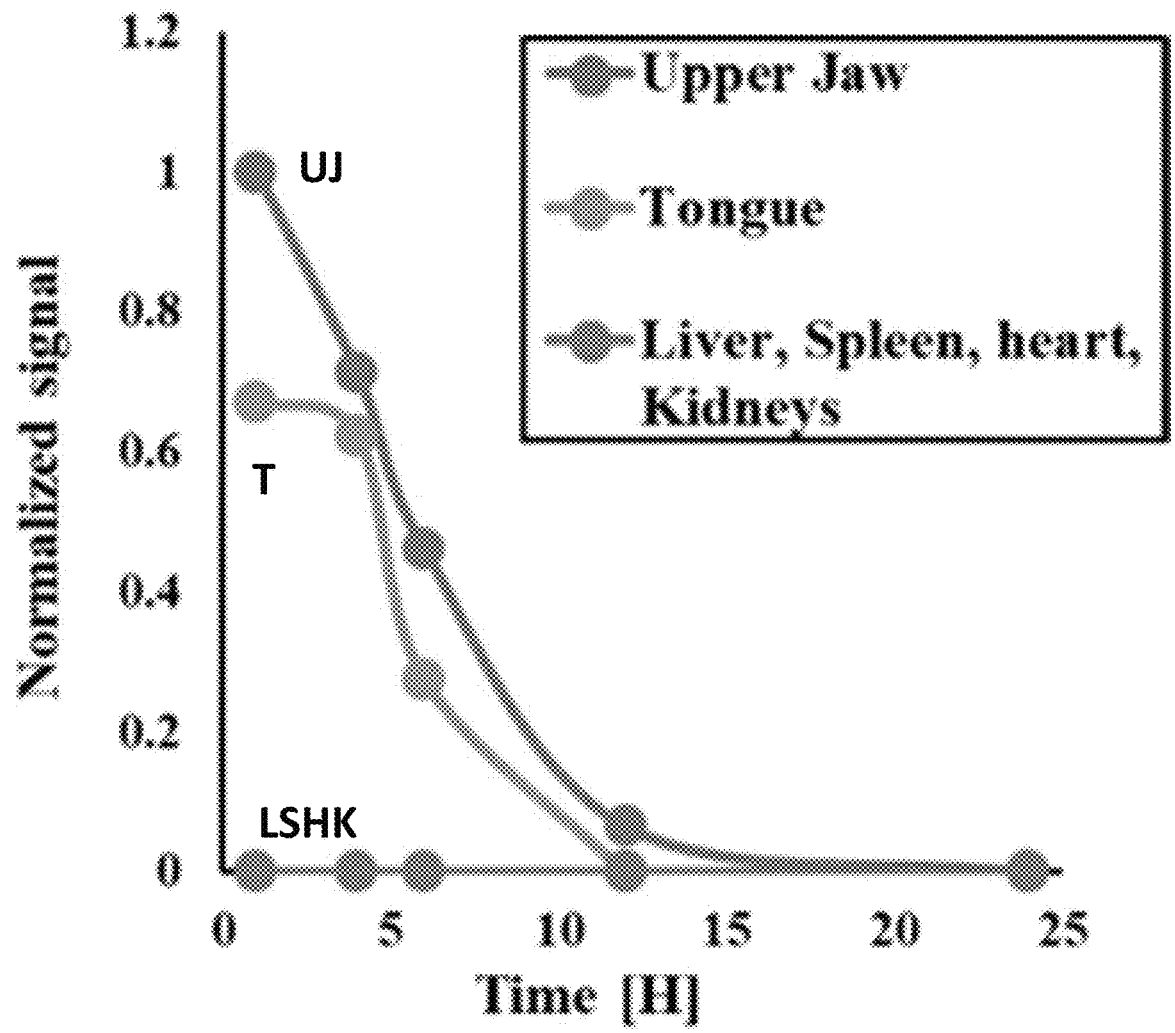

We compared the efficacy of rats treated by nanoparticulate enzymatic surgery to rats that underwent traditional surgery with a scalpel. Collagenase-loaded liposomes were inserted into the gingival sulcus, and tooth alignment was evaluated using an orthodontic spring (FIG. 9A). Over a treatment period of 15 days, we measured a similar enhancement of the tooth alignment trajectory motion in rats that underwent a surgical procedure in which the supracrestal collagen fibers were sectioned with a scalpel, and in rats that underwent the nano-enzymatic procedure. The nanoparticulate collagenase group had enhanced tooth alignment compared to both the sham group (empty liposomes) and the group treated with the free enzyme (FIG. 9B). The liposomal nanoparticulate collagenase group also displayed a three-fold enhancement in tooth alignment compared to ordinary braces (FIG. 9B). The accelerated tooth movement in the nano-surgery group compared to the other treatment groups is attributed to the biological relaxation of the collagen fibers. After 15 days, the teeth reached their maximal magnitude of mobility and the orthodontic spring was removed. The improved in vivo activity of the nanoparticulate delivery system corroborates the rapid in-vitro deactivation of the free enzyme (FIG. 9C). This suggests that the liposomal systems protected the enzyme in vivo, prolonging its release profile and confined the spatial distribution of the enzyme to the treatment site (FIG. 9C). The delivery system prevented the enzyme from deactivating prematurely and allowed it to maintain its therapeutic activity as compared to the free enzyme group.

One requirement a nano-surgery system must satisfy is specificity to the target site. This is achieved by selecting the proper proteolytic enzyme tailored biologically towards the target organ. In addition, the drug delivery system must confine the spatial biodistribution of the enzyme primarily to the treatment site and maintain the therapeutic dose needed for the surgery. To confine the release of collagenase to the treatment site, we tested the biodistribution of liposomes (100 nm) loaded with a florescent dye after being placed in the sulcus (FIG. 9C). The nanoparticles remained in close vicinity of the treated tooth for 24 hours. Eight hours post administration, we found traces of the particles also around the tongue due to liposomes leakage from the sulcus but not in the liver, heart, kidneys or spleen (FIG. 9C). Histological evaluation of these tissues demonstrated that they were unharmed (FIG. 9D), most likely due to the collagenase deactivation in saliva (FIG. 9A).

Figure 9D:
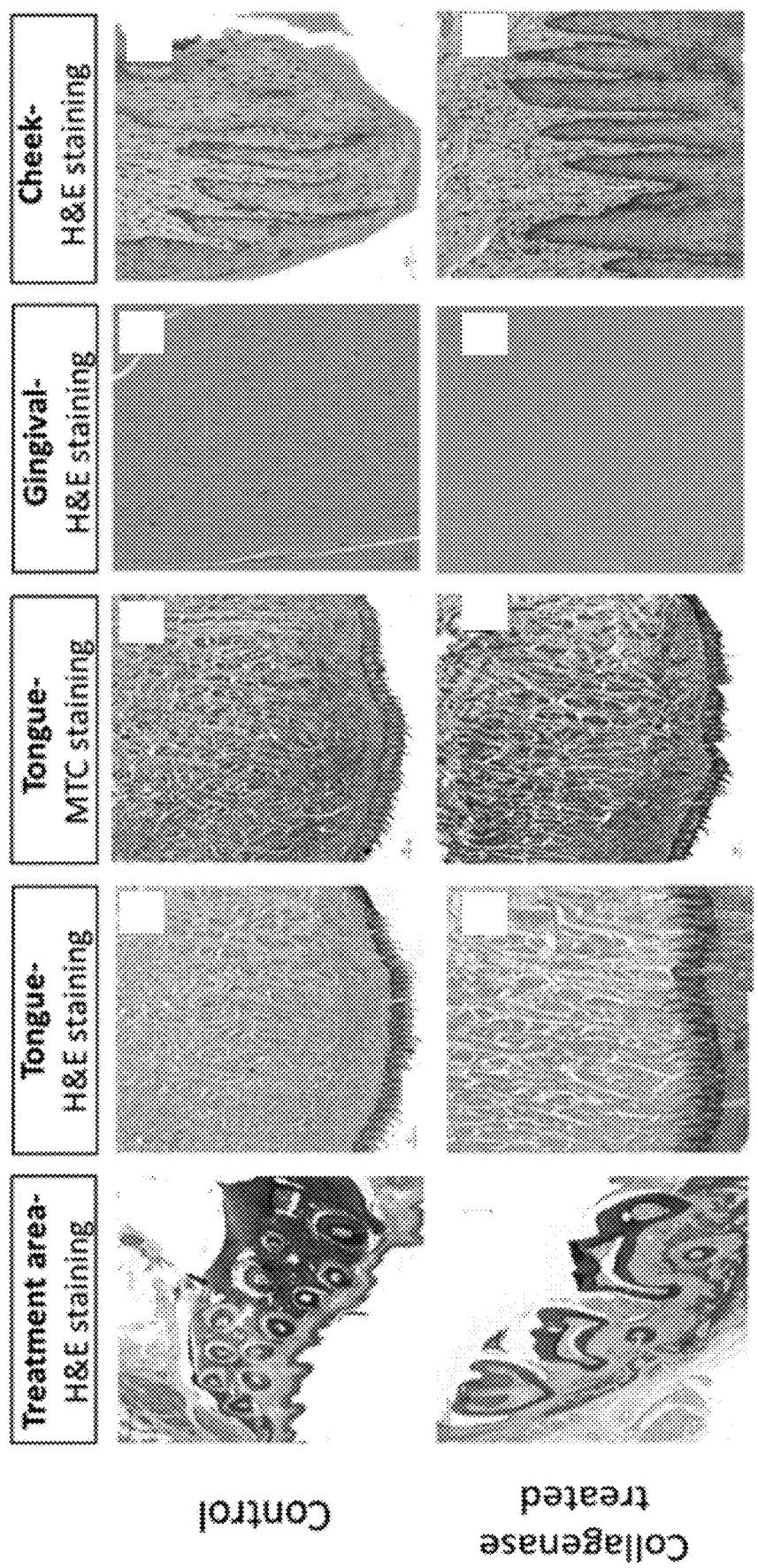
Figure 9E:
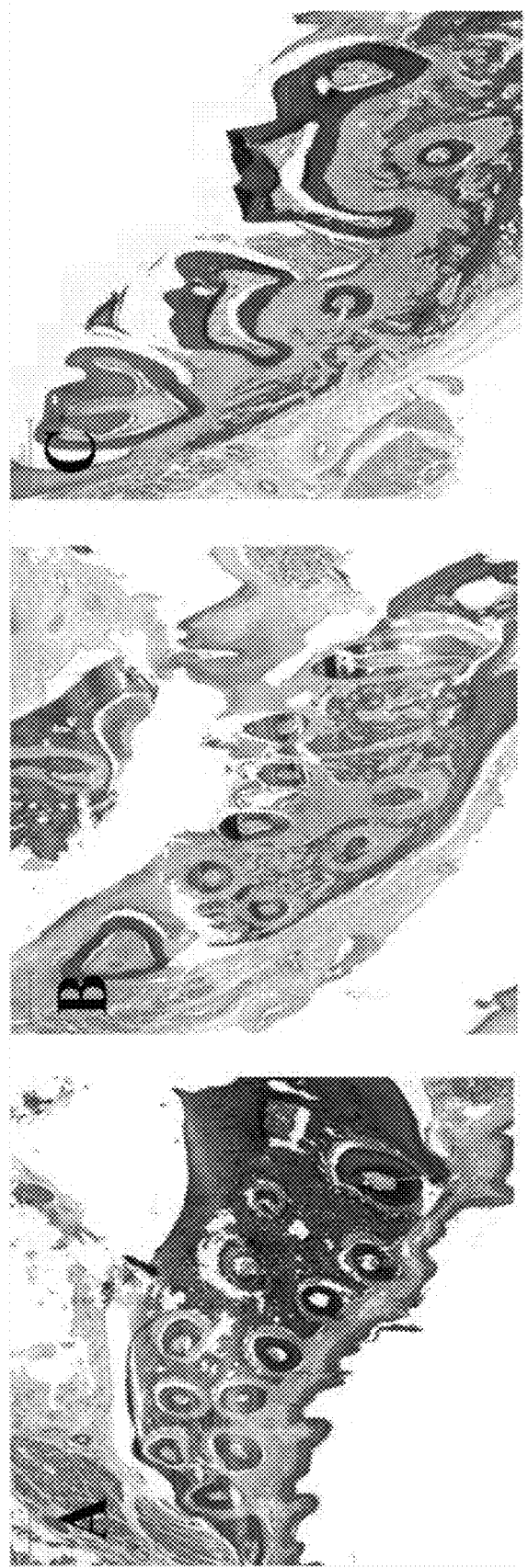

Aseptic inflammatory processes play a major role in preconditioning the alveolar bone for orthodontic tooth movement. We compared the degree of inflammation in rats treated with ordinary orthodontics to those with orthodontics supplemented with non-encapsulated collagenase, liposomal collagenase and surgery. Histological analysis of the gingival tissue shows similar presentation of mild inflammation among all groups (FIG. 9D-E).

Figure 9F:
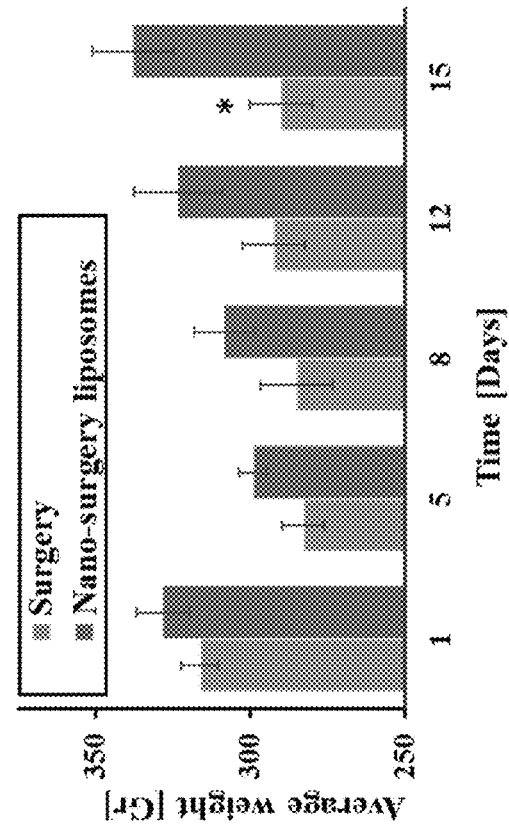
Figure 9G:
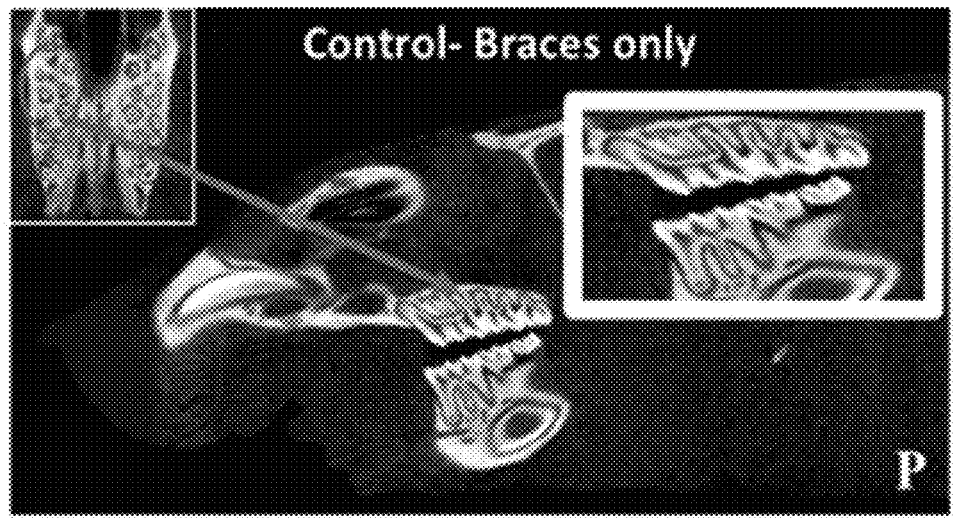

Interestingly, the animals' eating pattern was minimally affected by the treatment. During the first week all rats lost ~10% of their body weight. A similar weight-loss profile occurs also in humans undergoing orthodontic treatments and is associated with adapting to a device in one's mouth. After completing the treatment, only the nanoparticulate enzymatic rats regained the weight they lost (FIG. 9F). In comparison, rats treated by the traditional surgery displayed weight loss. Even though the teeth moved three-fold greater distance in the nano-surgery group, the rats continued eating solid pellet chow and regained normal weight, suggesting this treatment approach is associated with less discomfort.

Example 9

Tissue Remodeling after Nano-Surgery

Figure 9H:
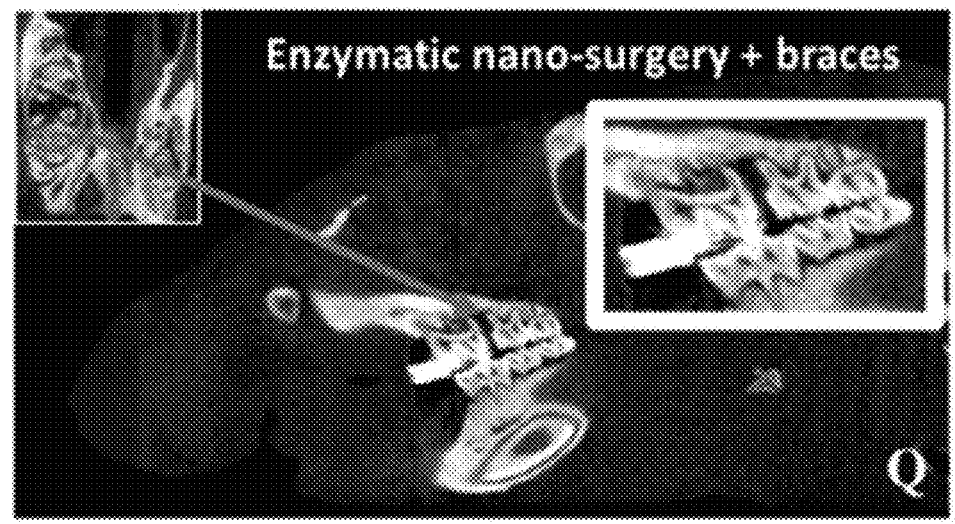
Figure 9I:
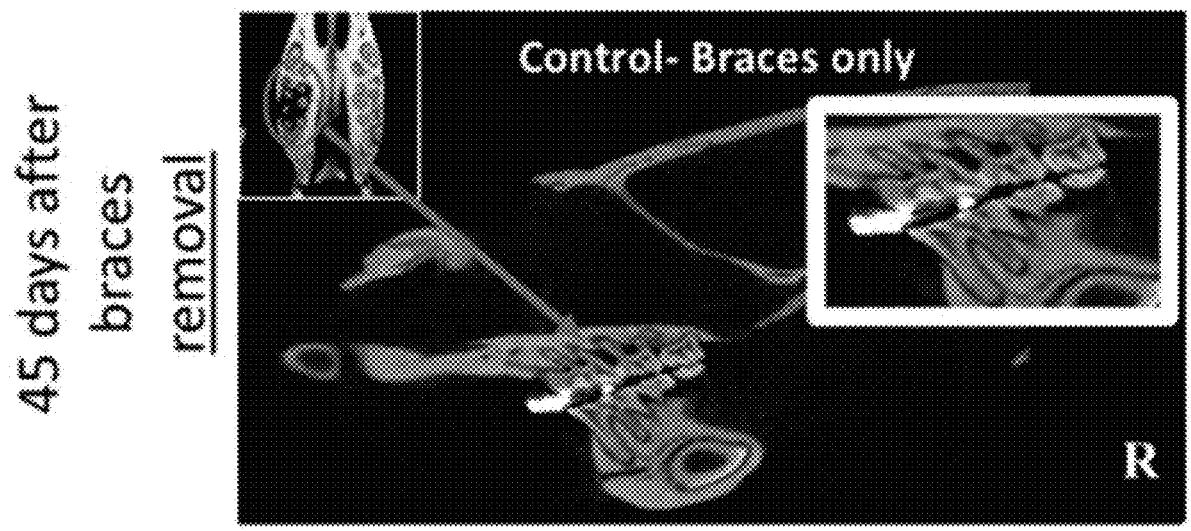
Figure 9J:
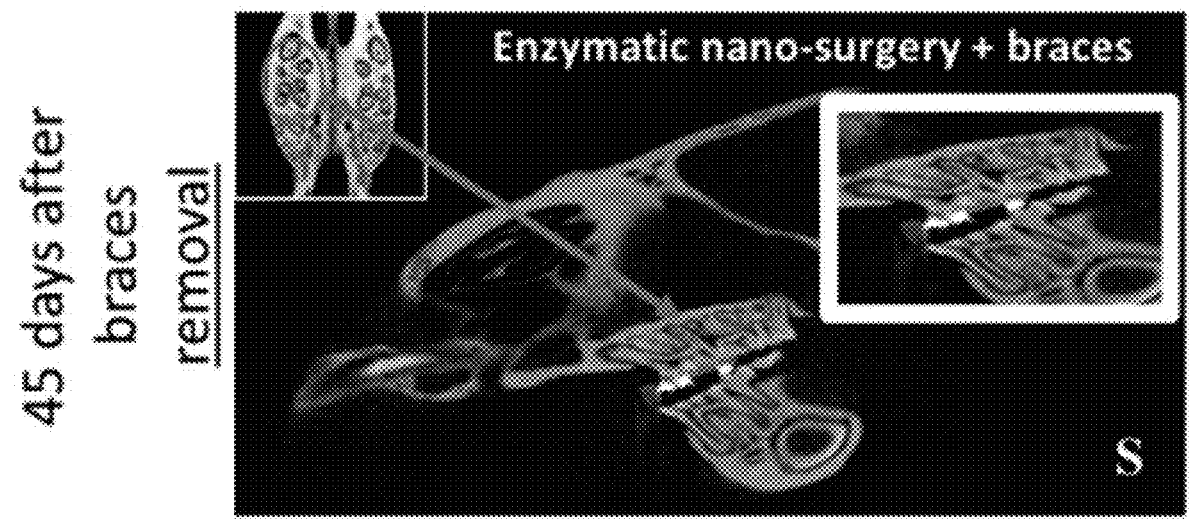

Regeneration of the soft and hard tissues that surround the teeth is necessary after a surgical process. We observed the changes the alveolar bone underwent throughout the enzymatic process. For this, microCT scans of the maxillofacial bone were performed 15 days after initiating the treatment and 45 days after removing the braces (i.e. day 60 of the experiment, FIG. 9G-J). Interestingly, bone recovery was faster and to a greater extent in the nano-enzymatic group compared to bone repair in the group treated with ordinary braces. At the beginning of the procedure, in tandem with tooth movement, bone absorption was observed at the treatment site (FIG. 9H). On day 60 (45 days after removing the braces), full bone recovery was observed at the new tooth orientation (FIG. 9J). These findings suggest that the periodontal bone regenerates in an improved manner after the nano-enzymatic surgical procedure.

Figure 9K:
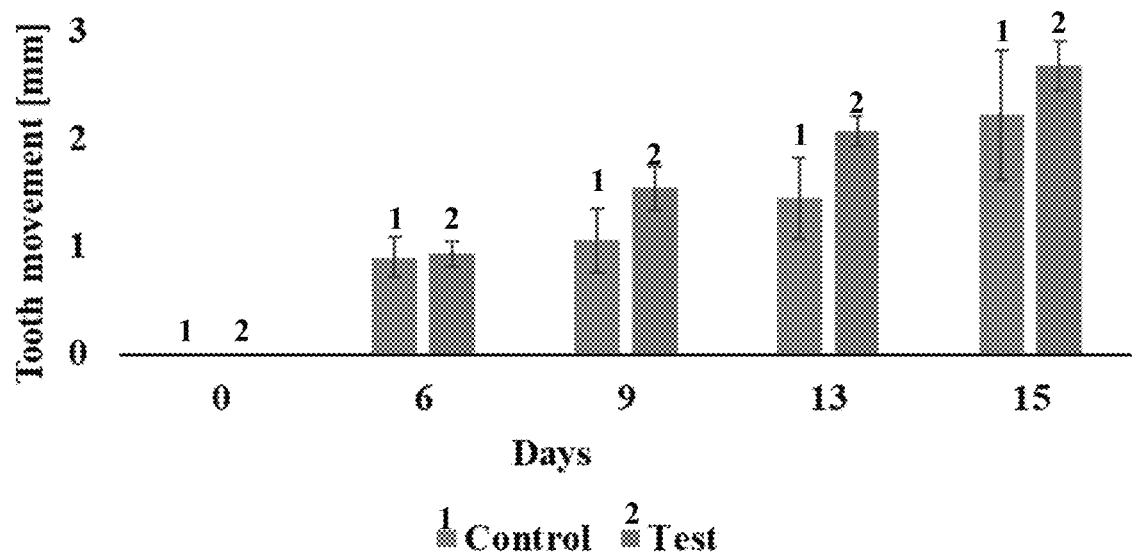
Figure 9K:
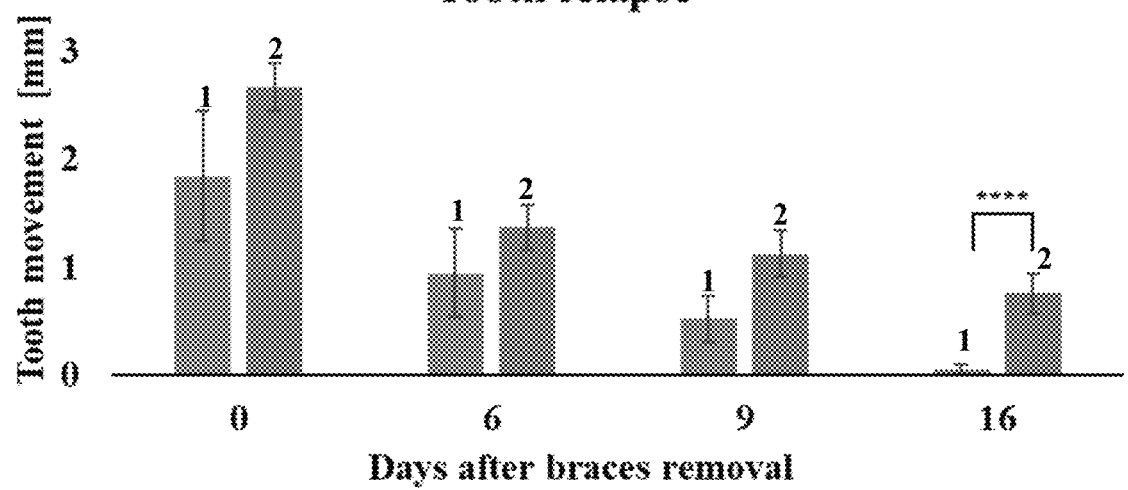
Figure 9L:
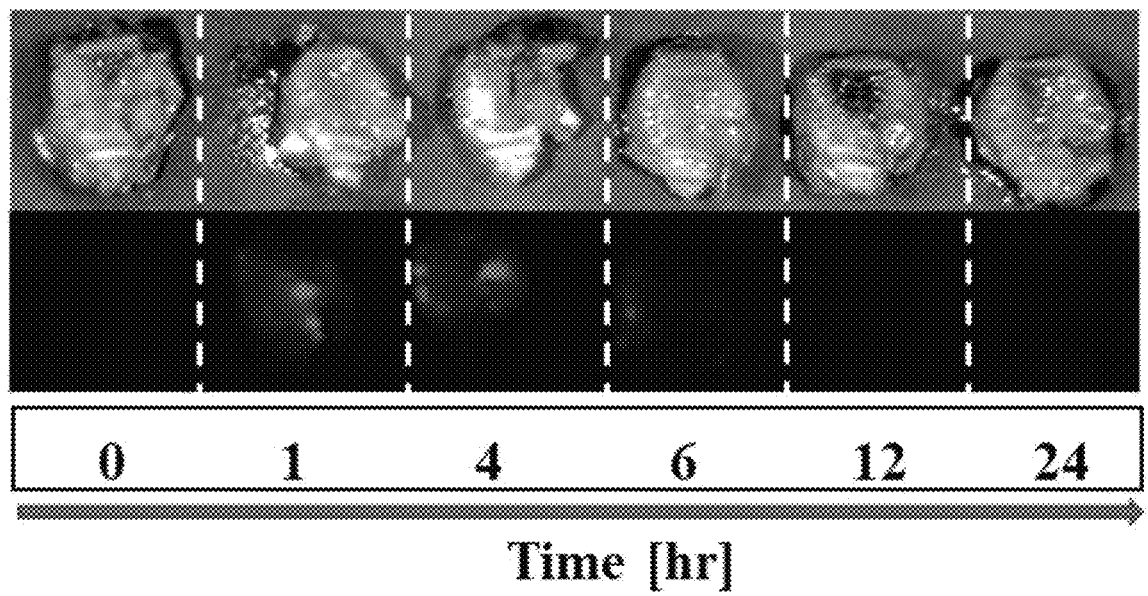
Figure 9M:
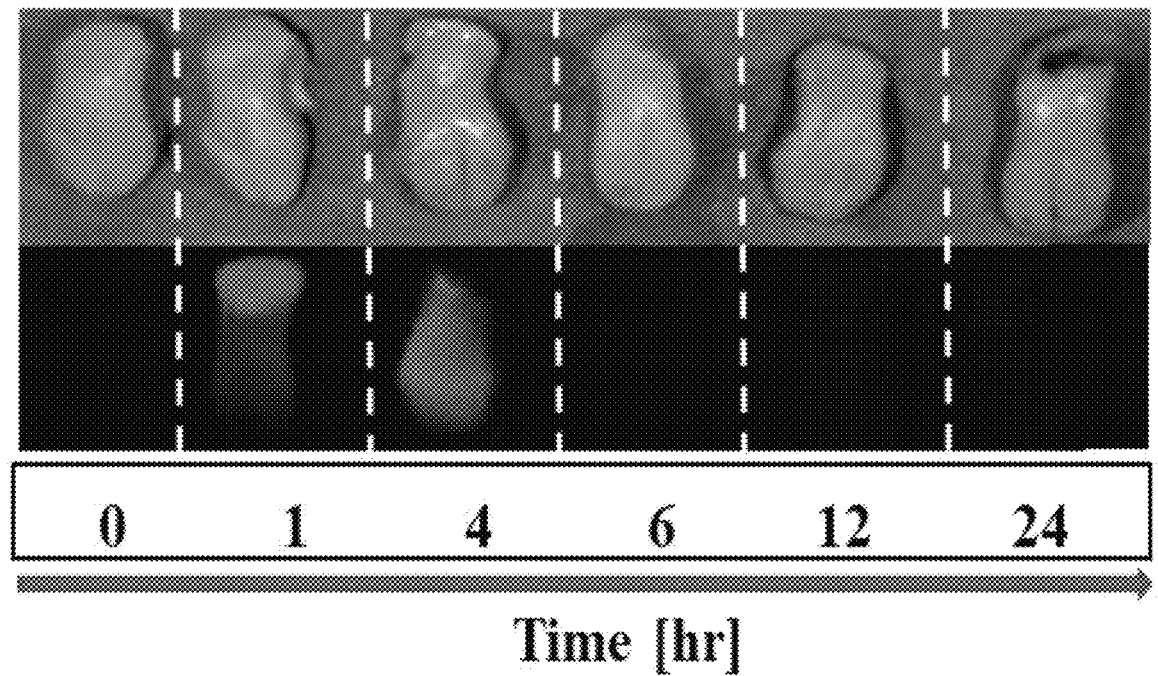
Figure 9N:
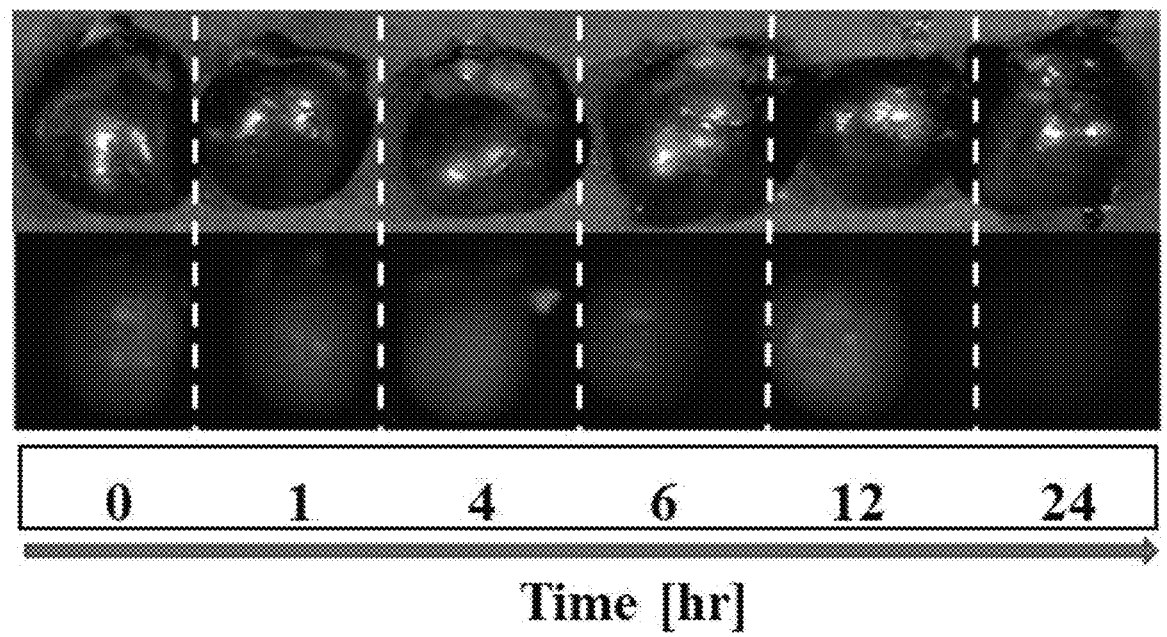
Figure 9O:
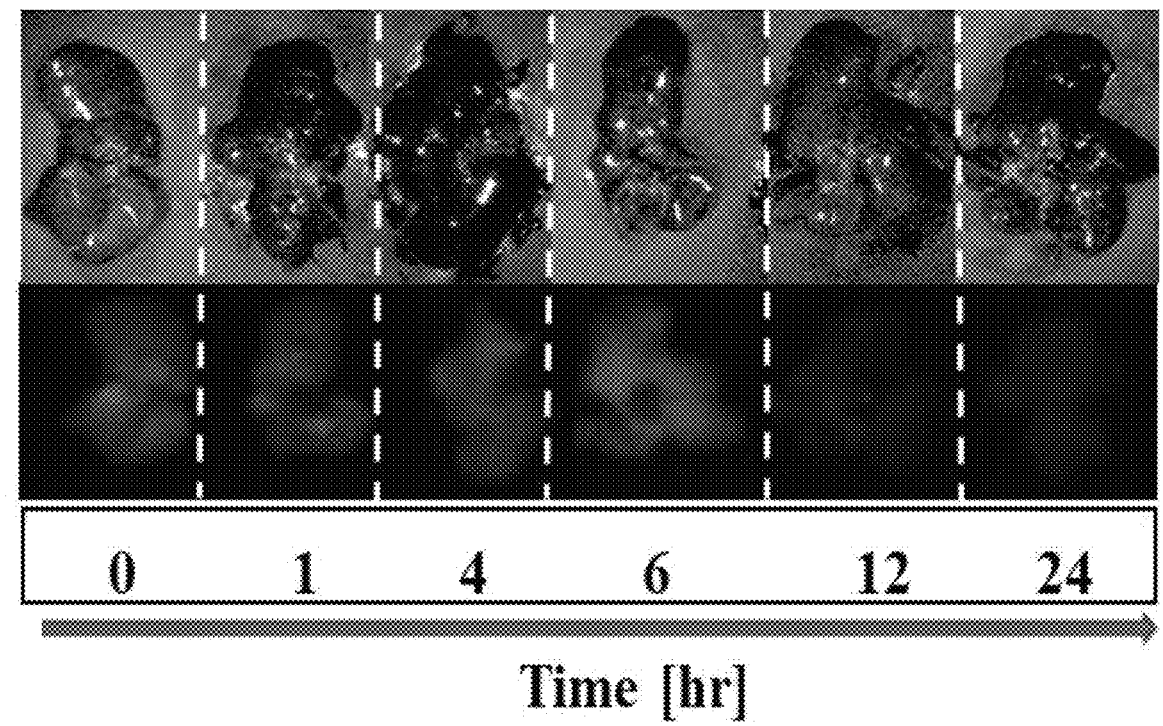

Relapse is a condition in which the teeth shift out of alignment back to their pre-orthodontic treatment position. Approximately 40% of patients suffer relapse, usually leading to a second cycle of orthodontic treatment. To avoid relapse, dentists affix the teeth using NiTi wires. Interestingly we noticed that nano-surgery treated rats had significantly less tooth relapse in comparison to the control group. On day sixteen after removing the braces the regular treatment completely relapsed, while the enzymatic nanoparticle treatment retained a 1 mm displacement gap at the treatment site. (FIG. 9K) We attribute the slow relapse in the nanoparticle treated group to improved regeneration of the collagen fibers and bone at the target position.

Example 10

Improved Liposome Generation

Having established that collagenase's activity drops rapidly at 37 degrees (FIG. 7B), other parameters during liposome production that might affect the protein's integrity and function were examined. For the ethanol procedure (see Materials and Methods), temperatures above 25 began reducing protein activity, likely due to denaturation, and temperatures above 50 had an even stronger effect (FIG. 10, left chart). Inclusion of any amount of ethanol was also found to denature the protein and reduce its activity (FIG. 10, middle chart). Lastly, a force above 10 bar during extrusion was found to have a negative effect on protein activity (FIG. 10, right chart).

Figure 11A:
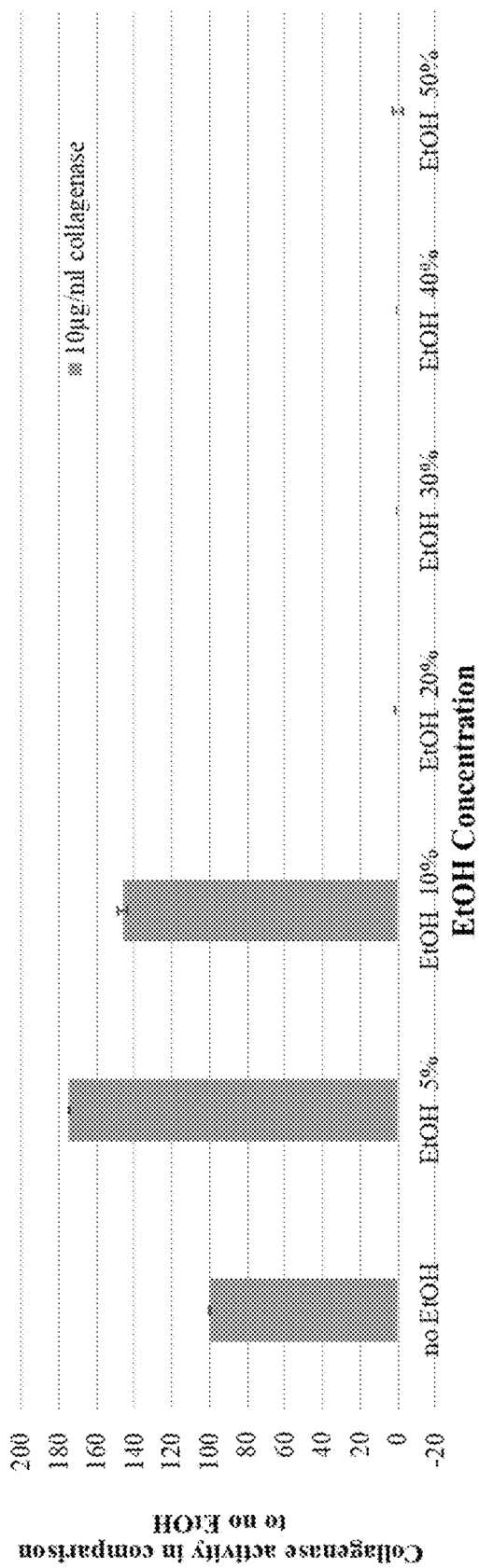
FIGS. 11A-D: Collagenase activity test in various conditions. (11A-C) Bar charts showing free collagenase activity at various (11A) ethanol concentrations, (11B) temperatures and (11C) pHs. (11D) Bar chart of gold particle concentration that leaked from DMPC and HSPC liposomes.
Figure 11B:
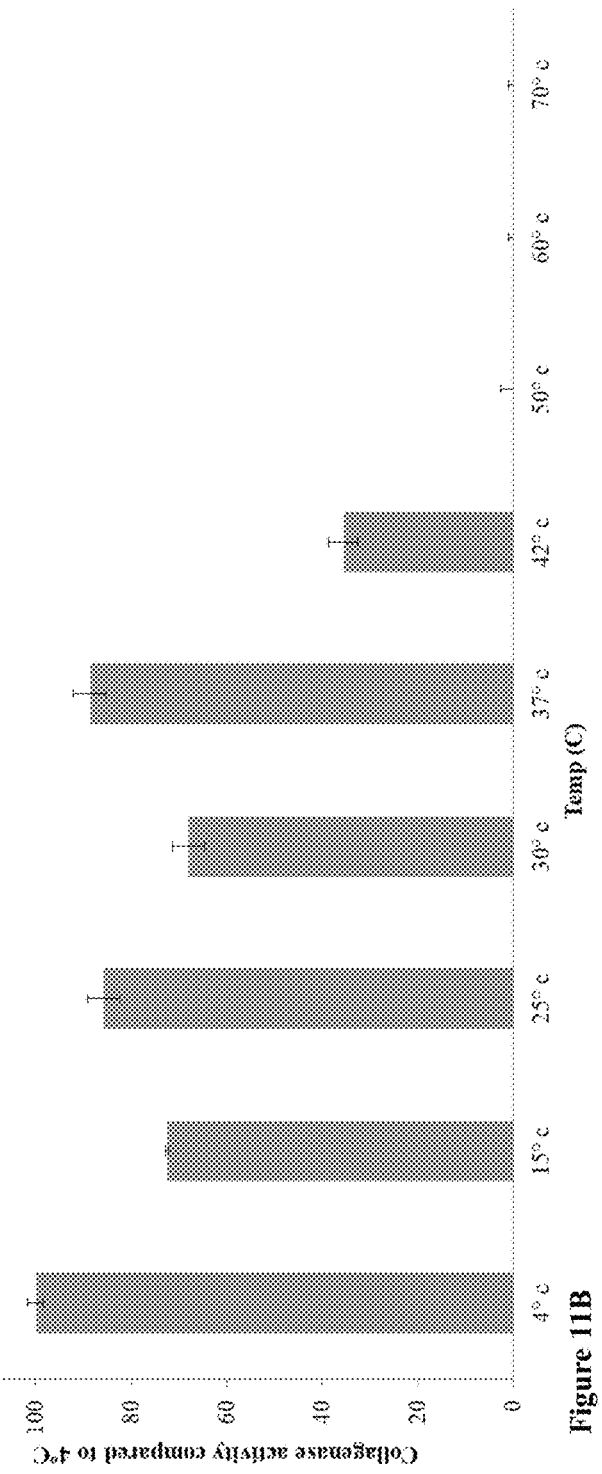
Figure 11C:
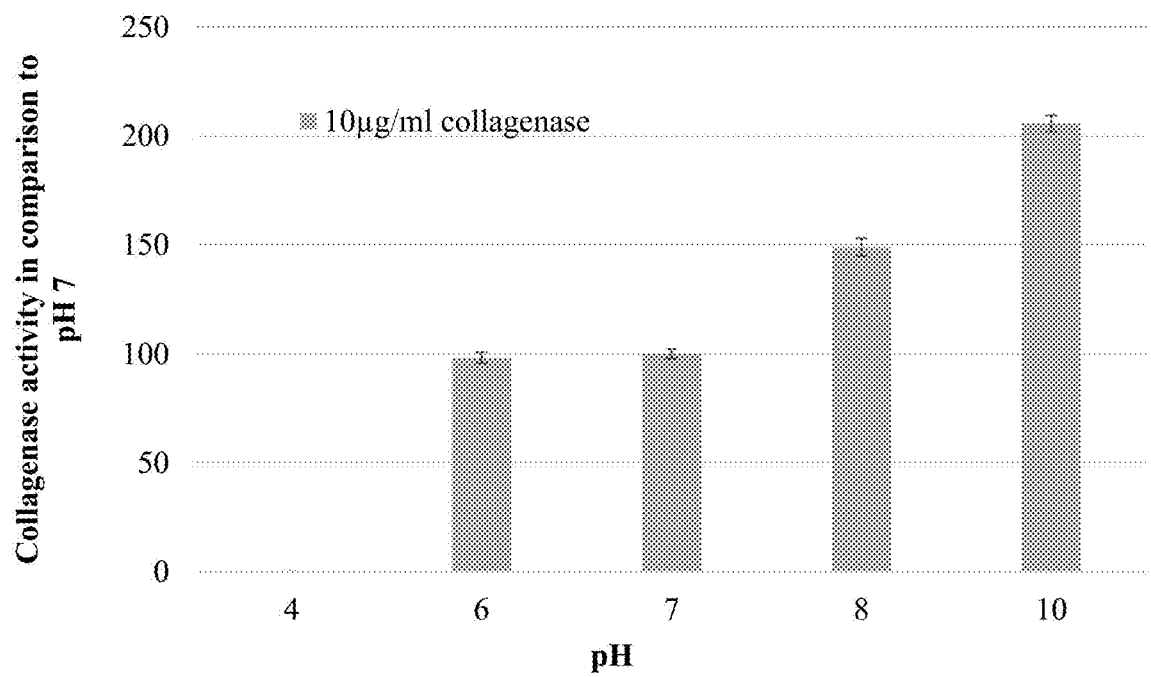

Based on these results, the effect of various conditions on the activity of free collagenase was assessed. Incubation of free enzyme in as little as 20% ethanol completely abrogated protein function (FIG. 11A). Similarly, a temperature of 50 degrees or greater also completely abrogated protein function, while any temperature above 4 degrees had a deleterious effect, highlighting the need to keep the production process as cold as possible (FIG. 11B). Lastly, the activity of free collagenase at various pH was assayed. Basic pH was found to result in improved collagenase activity (FIG. 11C), suggesting that the use of a basic aqueous medium during liposome production might be advantageous This led to the adoption of a new liposome production method: cold thin-film hydration. In this procedure, organic solvents are not used thus protecting the enzyme from their potential damaging effects, further because the lipids are solid during production of the liposomes there is no need for heating and the entire procedure can be performed at or below 20 degrees. Finally, extrusion was performed at not more than 10 bar, further ensuring the integrity and functionality of the enzyme.

Figure 11D:
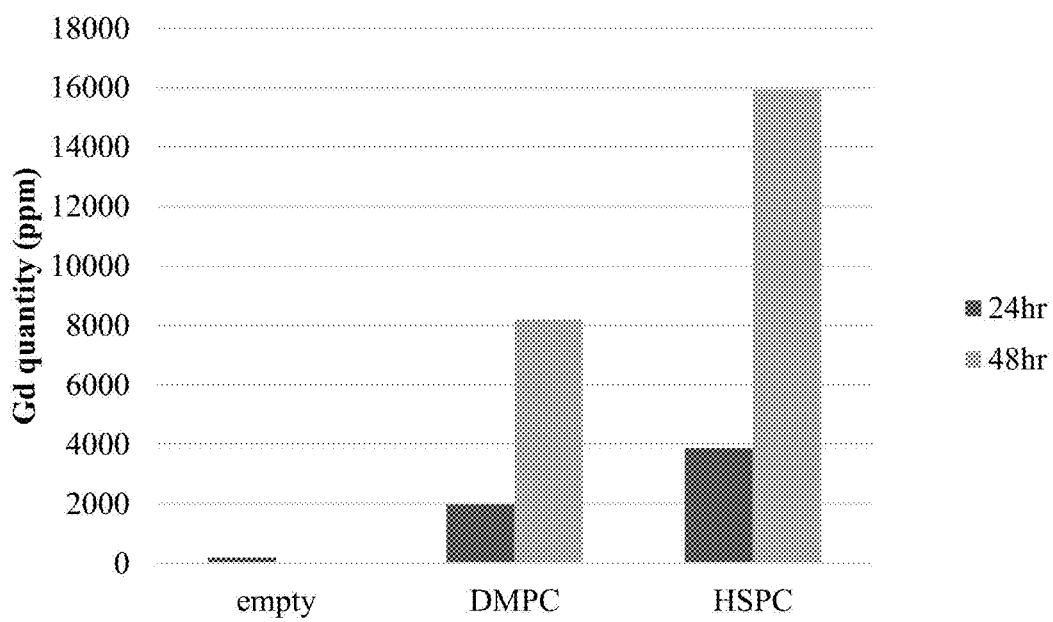

Several lipid combinations were also tested. First 1,2-dimyristoyl-sn-glycero-3-phosphatidylcholine (DMPC) and hydrogenated soy phosphatidylcholine (HSPC) were tested as the primary lipid in the liposome. HSPC has the higher Tm and thus was hypothesized to be less leaky than DMPC, which would result in extended enzyme retention and release. Liposomes comprising the primary lipid, cholesterol and PEG in a ratio of 56:39:5 and loaded with gold particles were generated by the cold thin-film method. The liposomes where then placed in a dialysis bad containing serum and release of the particles into the bag was measured after 24 hours and 48 hours. Unexpectedly, HSPC liposomes were found to be leakier, which a greater amount of gold particles found to have been released into the bag at both time points (FIG. 11D). Thus, thought HSPC has a higher Tm, DMPC was a superior primary lipid for generating slow release liposomes. 1-palmitoyl-2-oleoyl-sn-glycero-3-phosphocholine (POPC) and 1,2-dioleoyl-sn-glycero-3-phosphocholine (DOPC) were also tested, however, DMPC encapsulated the largest amount of protein as well as the most active protein (Table 1). Interestingly, with all three primary lipids the inclusion of positive charge (5% Dotap) resulted in increased protein encapsulation.

TABLE 1

|  | DOPC | DOPC-5% Dotap | POPC | POPC-5% Dotap | DMPC | DMPC-5% Dotap |
|---|---|---|---|---|---|---|
| Total Protein Florusecamine assay (ug/ml) | 40.81 | 78.78 | 12.5 | 99.56 | 111.84 | 130.4 |
| Active Protein Enzcheck assay (ug/ml) | 41.41 | 72.21 | 120.94 | 99.35 | 106.78 | 108.71 |

DMPC was thus selected as the primary lipid and the amount of DMPC to use was further assayed. Liposomes were generated using either 50 or 100 mM DMPC and encapsulating 2 mg/ml collagenase. The total amount of active collagenase encapsulated was comparable between the two compositions (Table 2). Further, addition of positive charge (Dotap) significantly increased the amount of encapsulated active protein, though a greater increase (5× vs 4×) was observed with 50 mM versus 100 mM. Finally, a starting concentration of 4 mg/ml collagenase instead of 2 mg/ml doubled the amount of encapsulated active collagenase. As such, the final production method entailed 50 mM DMPC, 39% cholesterol, 5% PEG encapsulating 4 mg/ml collagenase.

TABLE 2

|  | 50 mM DMPC-2 mg/ml collagenase | 50 mM DMPC 5% Dotap 2 mg/ml collagenase | 100 mM DMPC 2 mg/ml collagenase | 100 mM DMPC 5% Dotap 2 mg/ml collagenase | 50 mM DMPC-4 mg/ml collagenase |
|---|---|---|---|---|---|
| Enzcheck results concentration (μg/ml) | 202.76 | 998.27 | 214.22 | 757.806 | 1854.19 |

Finally, the cold thin-film method was directly compared to the ethanol injection method. Liposomes were produced with each method using 50 mM DMPC (56%), 39% cholesterol, and 5% PEG. Starting concentrations of 2 and 4 mg/ml collagenase were tried. Although ethanol injection produced more total encapsulated enzyme at both concentrations, the amount of active enzyme as assessed by Enzcheck was actually higher with the cold thin-film method (Table 3). Indeed, the ethanol method resulted in less than 25% of the enzyme that was encapsulated being active/non-denatured enzyme. In contrast, approximately 100% of the enzyme encapsulated by the cold thin-film method was active.

TABLE 3

|  | Ethanol injection | | Cold Thin-Film | |
| --- | --- | --- | --- | --- |
| Input collagenase concentration | 2 mg/ml | 4 mg/ml | 2 mg/ml | 4 mg/ml |
| Total Protein Florusecamine assay (ug) | 344.5 | 502.7 | 106.8 | 386.3 |
| Active Protein Enzcheck assay (ug) | 69.6 | 63.5 | 111.8 | 1854.2 |

Example 11

Treating Fibrosis with Highly Active Collagenase Liposomes

Having established that collagenase activity can be increased by producing liposomes at cold temperatures and without an organic solvent, the new liposomes were used for treating several forms of fibrosis. The new high-activity liposomes are used for decreasing fibrosis around pancreatic tumors as described hereinabove. PDAC mice are administered the new liposomes at least twice, spaced apart by at least one day, before the administration of paclitaxel micelles. The dosing regimen can be repeated for as many cycles as needed. The effect on tumor size and/or mice survival is measured.

Figure 12A:
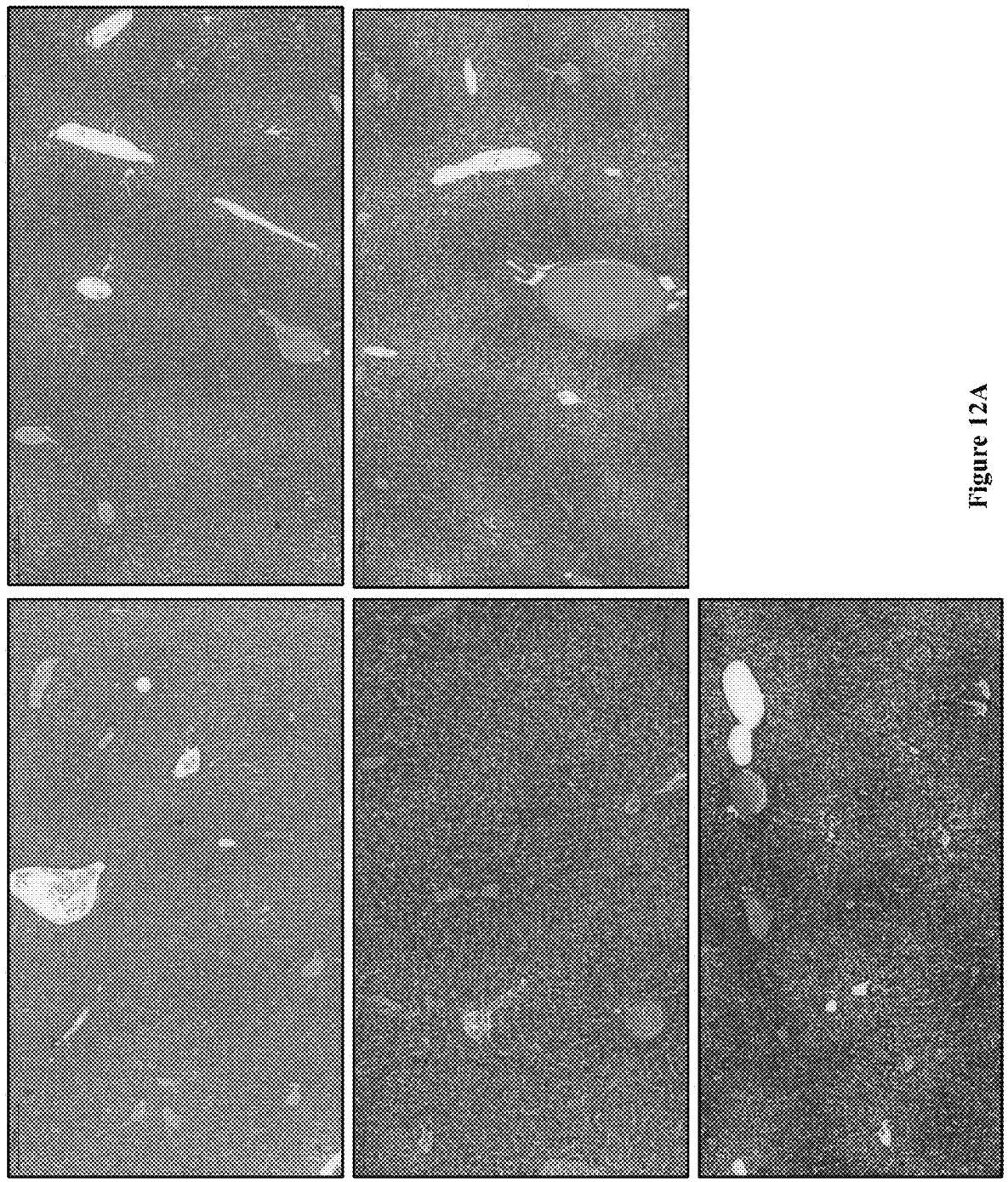
FIGS. 12A-F: Fibrotic conditions. (12A) Micrographs of Masson's trichrome staining of collagen in healthy and CCl4 treated livers, showing fibrosis in the treated livers. (12B) Micrographs of H&E staining in control and LPS treated lung tissue showing increased inflammation in LPS treated lungs. (12C-D) SEM images of (12C) healthy human conjunctiva and (12D) human pterygium. (12E) Photographs of the eyes of mice that received collagenase injections. (12F) Micrographs of Masson's trichrome staining of collagen in healthy human conjunctiva treated with PBS, collagenase I or collagenase II.

Liver fibrosis is generated in healthy mice by CCl4 administration. Balb/c mice are injected intraperitoneally with CCl4 for 2 weeks with 3 injections per week of 2-3 ml/kg CCL4. Collagen increase is measured by Masson's Trichrome (FIG. 12A) and optionally by H&E staining. After establishment of fibrosis, the mice are administered the new high-activity liposomes. Administration may be repeated and/or spaced apart by at least a day. After at least one round of dosing the animals are sacrificed and the collagen content of the livers is assessed.

Figure 12B:
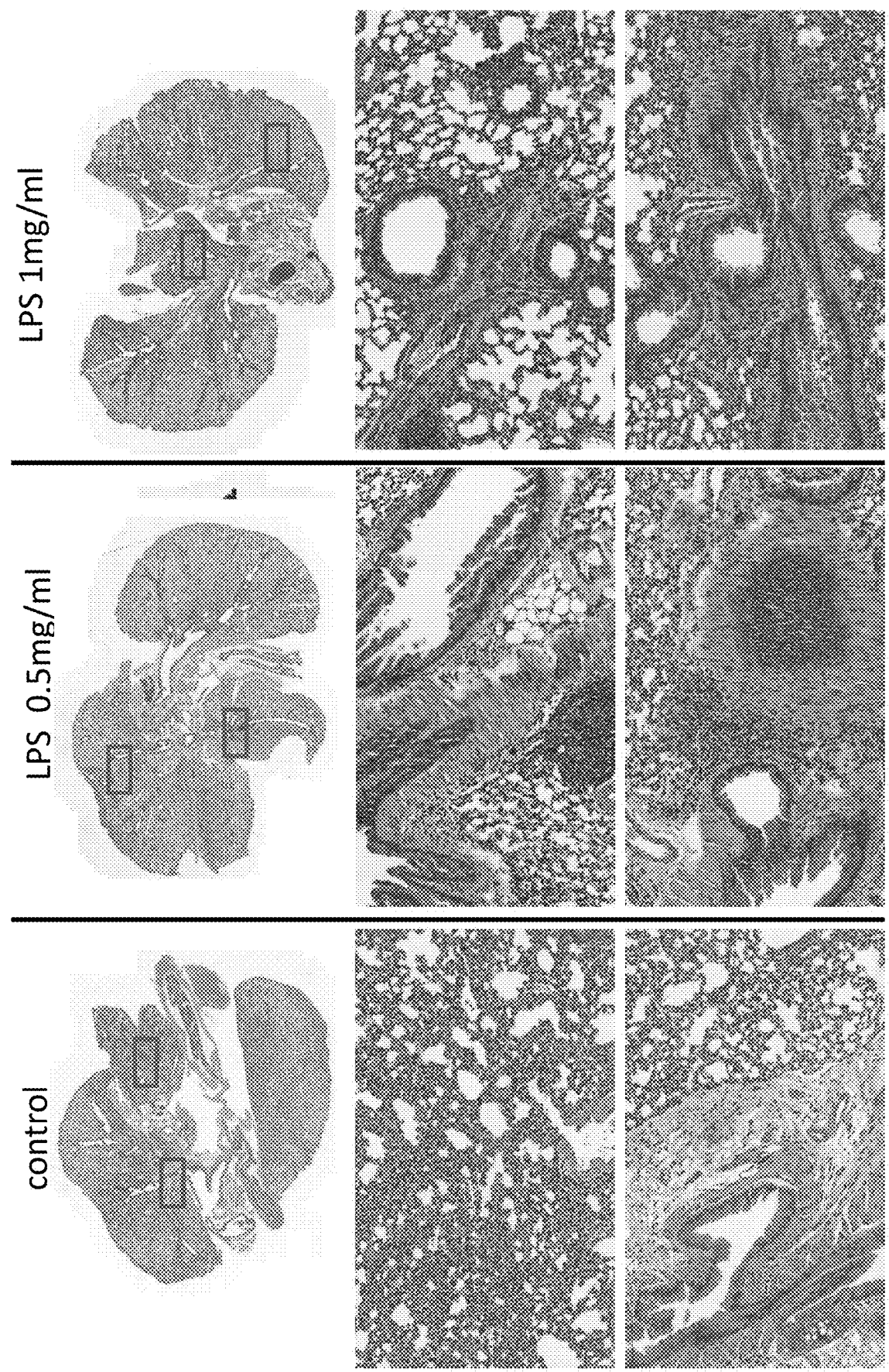

Lung fibrosis is generated by LPS inhalation. C57BL/6 mice are administered a single dose of 1 mg/ml LPS by aerosol inhalation for 2 minutes and lung fibrosis and inflammation are assayed by H&E staining and/or by Masson's Trichrome. 0.5 mg/ml LPS caused inflammation within 1 hour, with increased inflammation visible in the lungs of mice that received 1 mg/ml LPS (FIG. 12B).

Figure 12C:
Figure 12C:
Figure 12C:
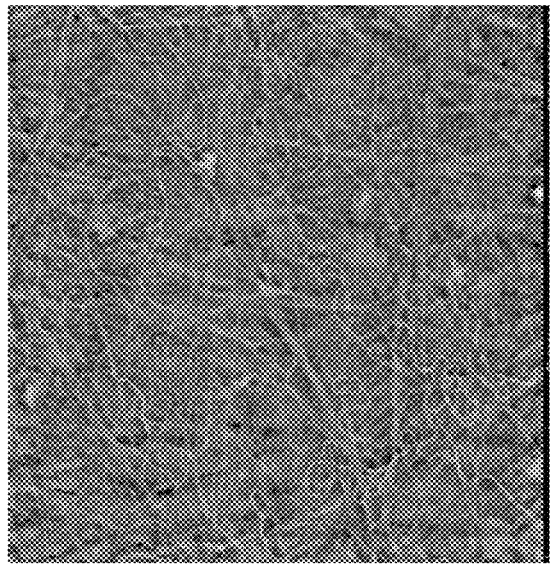
Figure 12D:
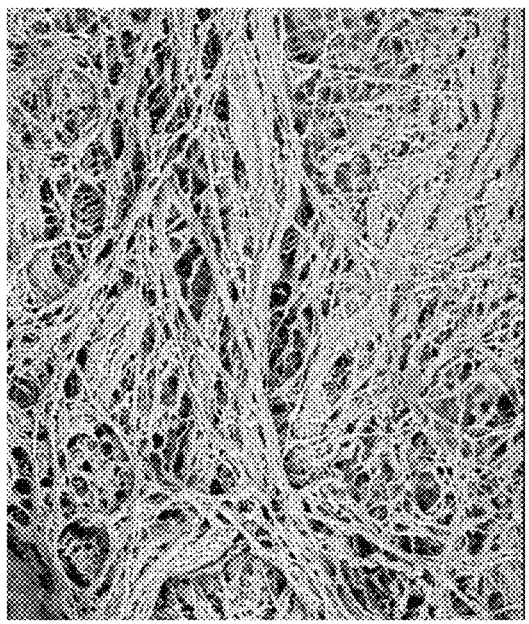

One form of increased connective tissue generation in the eye is known as pterygium, an outgrowth of the conjunctiva. This defect can be considered a form of fibrosis caused by sun and UV exposure. Healthy human conjunctiva samples were acquired and examined by scanning electron microscope (SEM) (FIG. 12C). Samples of human pterygium were also examined by SEM (FIG. 12D). In contrast to healthy conjunctiva, pterygium was found to be full of numerous pores of varying size (Table 4). The median pore size was 68 um$^2$, suggesting that particles below this size would readily enter the pterygium, but would not easily enter healthy conjunctiva.

TABLE 4

| Property | Median | Average |
| --- | --- | --- |
| Circle equivalent diameter | 9.32 μm | 10.2 μm |
| Major axis | 11.8 μm | 13 μm |
| Minor axis | 7.34 μm | 8.1 μm |
| Circumference | 31.2 μm | 35 μm |
| Convex hull | 31.1 μm | 34.6 μm |
| Circumscribed circle diameter | 12.6 μm | 14 μm |
| Area | 68.2 μm$^2$ | 89.6 μm$^2$ |
| Volume by area | 424 μm$^3$ | 758 μm$^3$ |
| Pixel count | 180 | 236 |
| Aspect ratio | 0.652 | 0.643 |
| Circularity | 0.888 | 0.863 |
| Convexity | 1 | 0.991 |
| Elongation | 0.348 | 0.357 |
| Grayscale | 175 | 179 |
| Inscribed circle diameter | 6.74 μm | 7.21 μm |

Figure 12E:
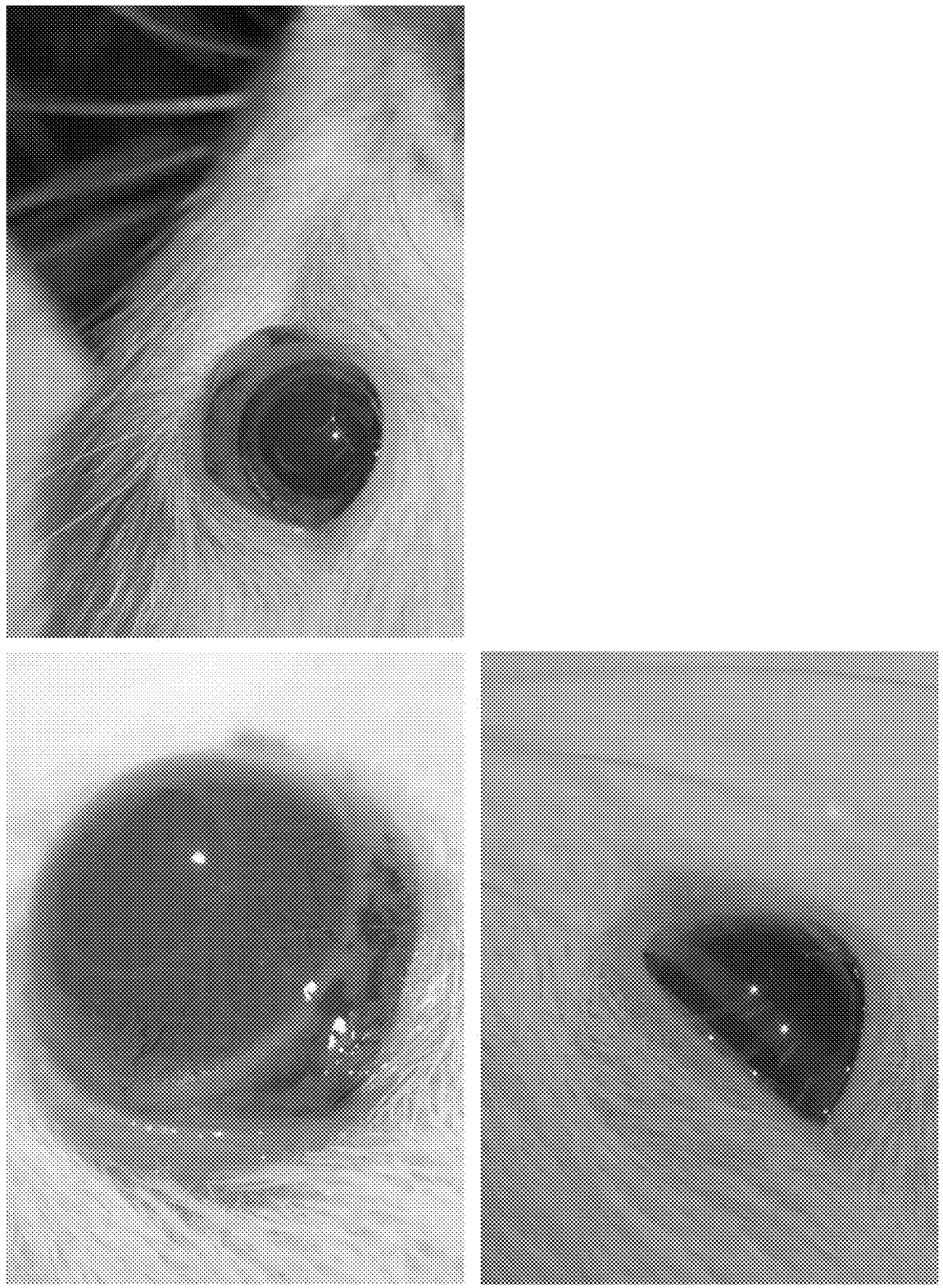

Pterygium is known to comprise four types of collagen: types I, II, III and IV. The stroma of pterygium and normal conjunctival tissue contains collagen types I, II, and II. To test the ability of collagenase to break up and treat pterygium, mice that had human pterygium transplanted to their eyes were administered 10 mg/ml free collagenase I by injection to the conjunctiva. However, due to the large amount of collagen found in many areas of the eye, the free collagenase caused a general breakdown of the eye, with extreme inflammation and damage seen throughout the eye (FIG. 12E).

Figure 12F:
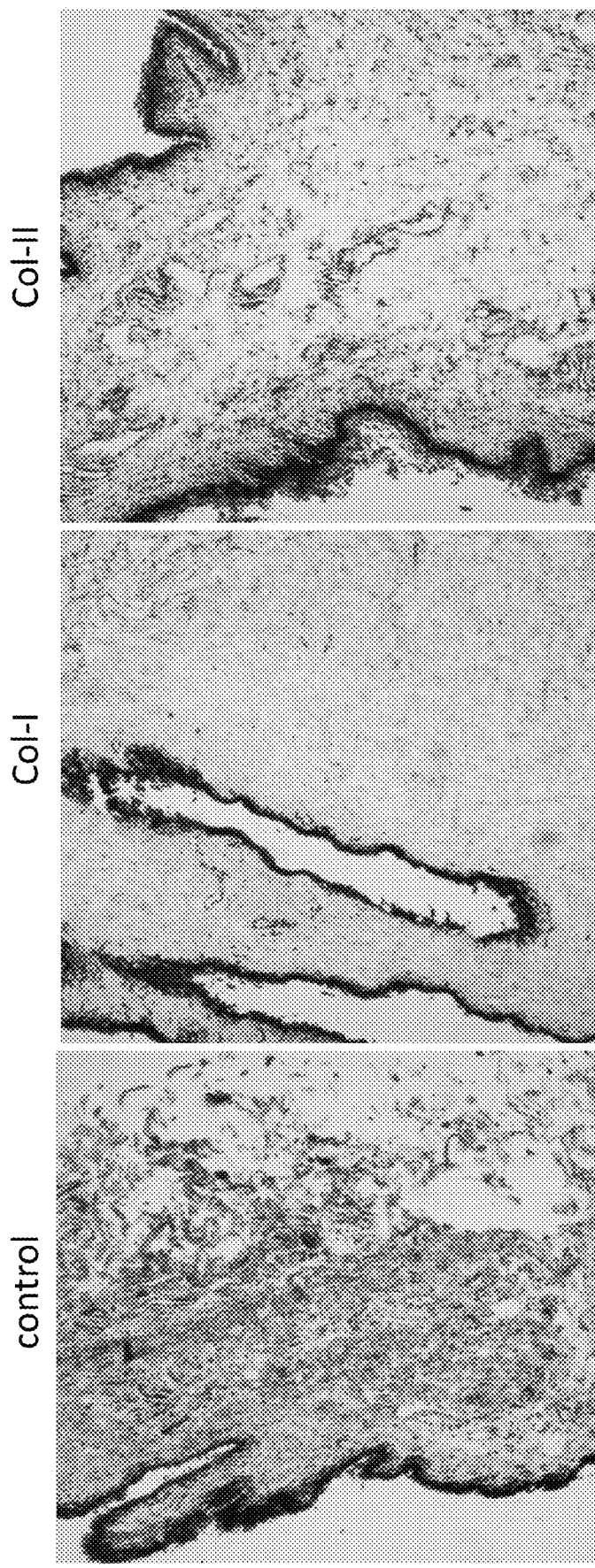

Targeted liposome delivery of collagenase just to the pterygium is one way to overcome the eye's sensitivity to the enzyme. An alternative would be to find a less destructive enzyme. In order to do that, conjunctiva from healthy humans were incubated in culture with 4 mg/ml of collagenase I or 4 mg/ml of collagenase II. Collagenase II was found to be far less destructive to the collagen of the conjunctiva, and thus might be an alternative enzyme to load into liposomes (FIG. 12F).

Figure 13:
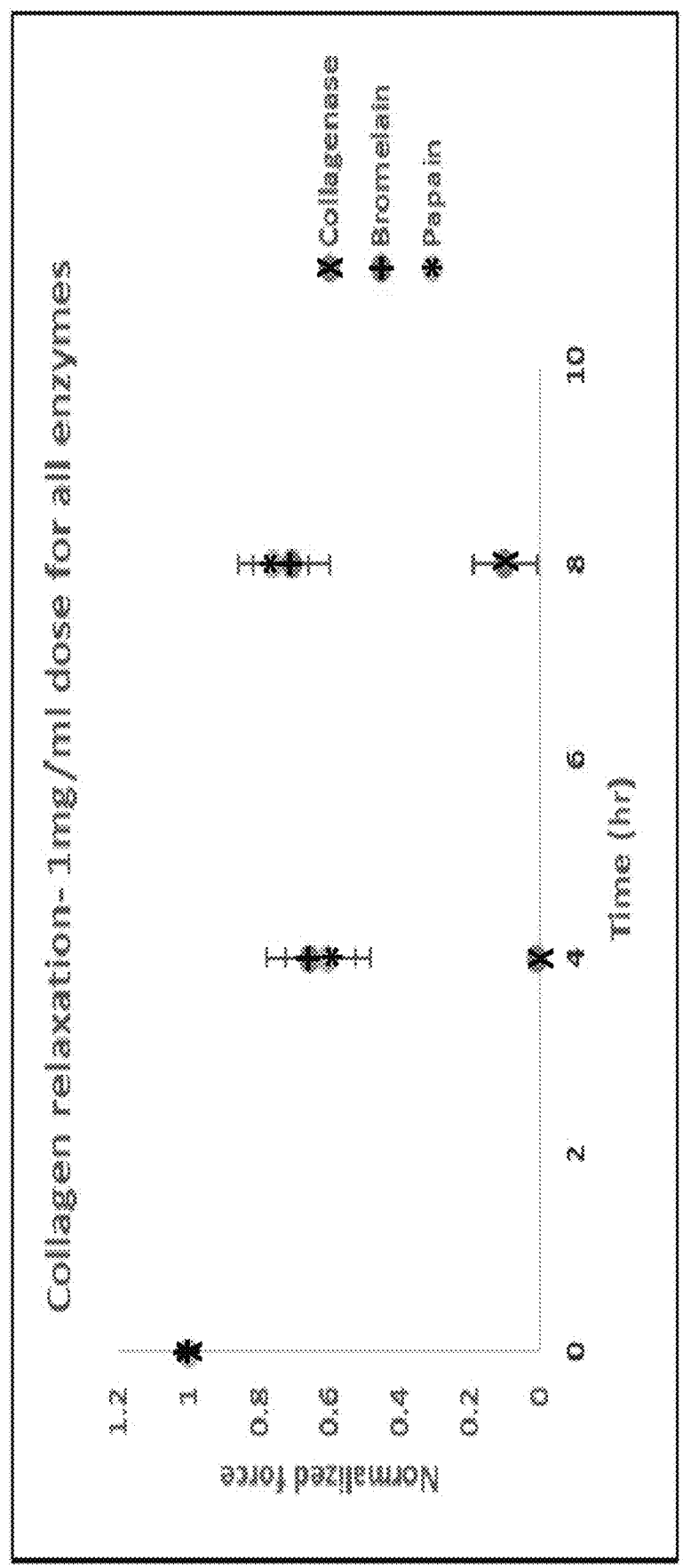
FIG. 13: Papain and bromelain activity test. Dot plot of the normalized force required to break collagen fiber bundles treated with collagenase I, papain or bromelain.

Two plant-based proteolytic enzymes were also tested for their ability to relax collagen: bromelain and papain. These plant-based enzymes are not specific to collagen but have been reported to act on collagen fibers. Collagens fiber strength was tested with a force machine in the presence of 1 mg/ml collagenase, bromelain or papain. The force required to break a bundle of fibers with no treatment was set to 1, and the force required to break the treated fiber bundles was standardized to this force. Collagenase I was capable of rupturing the fibers with almost no force after 4 hours of treatment (FIG. 13). At this same time point bromelain and papain reduced the strength of the collagen fibers such that less than 70% of the control force was needed to rupture the fibers. This suggests that the fiber integrity was reduced by as much as 30%. Fibers examined at 8 hours of incubation showed similar results. Thus, both papain and bromelain served as effective collagen relaxing enzymes, though much weaker ones than collagen I.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A pharmaceutical composition formulated for administration to a human comprising at least one lipid-based particle encapsulating at least one proteolytic enzyme in solution and a pharmaceutically acceptable carrier, wherein at least 75% of said proteolytic enzyme is proteolytically active and wherein said solution comprises a pH from 8 to 10.

2. The pharmaceutical composition of claim 1, wherein (i) said carrier is substantially devoid of ions that activate said proteolytic enzyme, (ii) said proteolytic enzyme is dissolved in an aqueous solution devoid of ions that activate said proteolytic enzyme or (iii) both (i) and (ii).

3. The pharmaceutical composition of claim 1, wherein said lipid- based particle (i) is a liposome, (ii) comprises a maximum cross-sectional area of less than 70 square microns or (iii) both (i) and (ii).

4. The pharmaceutical composition of claim 3, wherein said liposome comprises between 50 and 60% D1VIPC, 35 and 45% cholesterol and 3 and 7% 1,2-distearoyl-sn-glycero-3-phosphoethanolamine-N-methoxy-PEG (PEG-D SPE).

5. The pharmaceutical composition of claim 1, wherein said proteolytic enzyme (i) is active against collagen, (ii) is selected from collagenase, papain and bromelain, or (iii) both (i) and (ii).

6. The pharmaceutical composition of claim 5, wherein said proteolytic enzyme is collagenase.

7. The pharmaceutical composition of claim 6, wherein said collagenase is collagenase I, collagenase II or both.

8. A method of decreasing fibrosis in a subject in need thereof, the method comprising administering to said subject the pharmaceutical composition of claim 1, thereby decreasing fibrosis in said subject in need thereof.

9. A method of increasing penetrance of a drug into a tumor in a subject in need thereof, the method comprising:
   a. administering to the subject a pharmaceutical composition of claim 1; and
   b. administering said drug to said subject, thereby increasing the penetrance of said drug into said tumor.

10. The method of claim 9, wherein said administering said drug occurs at a time after administering said pharmaceutical composition sufficient for degradation of extra cellular matrix (ECM) around said tumor, wherein said administering said drug occurs at least 24 hours after administering said pharmaceutical composition, wherein administering said pharmaceutical composition comprises administering 2 doses at least 24 hours apart or wherein administering said pharmaceutical composition does not increase the number of circulating tumor cells in said subject.

11. The method of claim 8, wherein said fibrosis is selected from the group consisting of: pancreatic fibrosis, lung fibrosis, liver fibrosis and pterygium.

12. A method of producing a pharmaceutical composition comprising a liposome encapsulating at least one proteolytic enzyme, the method comprising:

a. providing a thin lipid film; and
b. rehydrating said thin lipid film with a solution comprising said proteolytic enzyme, wherein said rehydrating produces liposomes encapsulating said proteolytic enzyme wherein at least 75% of said proteolytic enzyme is proteolytically active and wherein said solution comprises a pH from 8 to 10;
thereby producing liposomes encapsulating at least one enzyme.

13. The method of claim 12, wherein at least one of:
a. said thin lipid film is produced by evaporating a lipid solution dissolved in an organic solvent and wherein said evaporating is performed at a temperature not higher than 37 degrees Celsius;
b. said enzyme is collagenase;
c. said solution comprising said enzyme is below the lowest transition temperature of a lipid in thin lipid film, at or below 15 degrees Celsius or both;
d. said rehydrating does not comprise vortexing, a temperature above 15 degrees Celsius or both;
e. at least 75% of said encapsulated enzyme is enzymatically active; and
f. said method is performed at a temperature of not more than 20 degrees Celsius.

14. The method of claim 12, further comprising at least one of: (i) downsizing said liposomes produced in (b) with an extruder, wherein said downsizing is performed at a temperature of not more than 20 degrees Celsius and at a maximal working pressure of not more than 10 bar; and (ii) testing the enzymatic activity of said encapsulated enzyme to ensure that at least 75% of said encapsulated enzyme is enzymatically active.

15. The pharmaceutical composition of claim 1, wherein a proteolytically active enzyme is an enzyme that is capable of cleaving its target.

16. The pharmaceutical composition of claim 1, wherein a proteolytically active enzyme is an enzyme that is active as determined by a collagen cleaving Protease Assay.

17. The pharmaceutical composition of claim 1, formulated for systemic administration.

18. The pharmaceutical composition of claim 1, formulated for intravenous administration.

19. The method of claim 12, wherein said solution:
i. is devoid of organic solvents;
ii. is devoid of ions that activate said enzyme;
iii. comprises a temperature below a transition temperature of a lipid in said thin lipid film; or
iv. is a combination thereof.

20. A pharmaceutical composition formulated for administration to a human comprising at least one lipid-based particle encapsulating collagenase in solution and a pharmaceutically acceptable carrier, wherein at least 75% of said collagenase is proteolytically active and wherein said solution comprises a pH from 8 to 10.

* * * * *